United States Patent
Sun et al.

(10) Patent No.: US 12,319,663 B2
(45) Date of Patent: Jun. 3, 2025

(54) ALKENE-CONTAINING AMIDE COMPOUND AND APPLICATION THEREOF

(71) Applicants: SHENYANG SINOCHEM AGROCHEMICALS R&D CO., LTD., Liaoning (CN); JIANGSU YANGNONG CHEMICAL CO., LTD., Jiangsu (CN)

(72) Inventors: Bing Sun, Liaoning (CN); Huibin Yang, Liaoning (CN); Hongjuan Ma, Liaoning (CN); Junwu Ying, Liaoning (CN); Dongliang Cui, Liaoning (CN); Bo Qin, Liaoning (CN); Shuang Liang, Liaoning (CN); Gang Wang, Liaoning (CN); Zhengmao Lu, Liaoning (CN); Fan Zhang, Liaoning (CN); Lin Chen, Liaoning (CN); Heying Pei, Liaoning (CN); Yan Cheng, Liaoning (CN); Mingxin Wang, Liaoning (CN); Bin Li, Liaoning (CN)

(73) Assignees: SHENYANG SINOCHEM AGROCHEMICALS R&D CO., LTD., Liaoning (CN); JIANGSU YANGNONG CHEMICAL CO., LTD., Jiangsu (CN)

( * ) Notice: Subject to any disclaimer, the term of this patent is extended or adjusted under 35 U.S.C. 154(b) by 536 days.

(21) Appl. No.: 17/754,669

(22) PCT Filed: Sep. 30, 2020

(86) PCT No.: PCT/CN2020/119134
§ 371 (c)(1),
(2) Date: Apr. 8, 2022

(87) PCT Pub. No.: WO2021/068816
PCT Pub. Date: Apr. 15, 2021

(65) Prior Publication Data
US 2023/0037883 A1    Feb. 9, 2023

(30) Foreign Application Priority Data

Oct. 8, 2019 (CN) .......................... 201910950934.4
Mar. 13, 2020 (CN) .......................... 202010174419.4

(51) Int. Cl.
| | | |
|---|---|---|
| C07D 257/06 | (2006.01) |
| A01N 43/713 | (2006.01) |
| A01N 43/80 | (2006.01) |
| A01N 43/82 | (2006.01) |
| A01P 13/00 | (2006.01) |
| C07D 249/14 | (2006.01) |
| C07D 271/04 | (2006.01) |
| C07D 271/113 | (2006.01) |
| C07D 285/135 | (2006.01) |
| C07D 401/12 | (2006.01) |
| C07D 401/14 | (2006.01) |
| C07D 403/12 | (2006.01) |
| C07D 405/12 | (2006.01) |
| C07D 413/12 | (2006.01) |
| C07D 413/14 | (2006.01) |
| C07D 417/12 | (2006.01) |

(52) U.S. Cl.
CPC ......... *C07D 257/06* (2013.01); *A01N 43/713* (2013.01); *A01N 43/80* (2013.01); *A01N 43/82* (2013.01); *A01P 13/00* (2021.08); *C07D 249/14* (2013.01); *C07D 271/04* (2013.01); *C07D 271/113* (2013.01); *C07D 285/135* (2013.01); *C07D 401/12* (2013.01); *C07D 401/14* (2013.01); *C07D 403/12* (2013.01); *C07D 405/12* (2013.01); *C07D 413/12* (2013.01); *C07D 413/14* (2013.01); *C07D 417/12* (2013.01)

(58) Field of Classification Search
CPC ................ C07D 257/06; C07D 249/14; C07D 271/04; C07D 271/113; C07D 285/135; C07D 401/12; C07D 401/14; C07D 403/12; C07D 405/12; C07D 413/12; C07D 413/14; C07D 417/12; A01N 43/713; A01N 43/80; A01N 43/82; A01N 43/653; A01P 13/00
See application file for complete search history.

(56) References Cited

U.S. PATENT DOCUMENTS

2018/0282290 A1* 10/2018 Koehn ................ C07D 257/06

FOREIGN PATENT DOCUMENTS

| CN | 108290846 A | 7/2018 |
| WO | 2009123714 A2 | 10/2009 |
| WO | 2018202535 A1 | 11/2018 |
| WO | 2020108518 A1 | 6/2020 |

* cited by examiner

*Primary Examiner* — Mina Haghighatian
*Assistant Examiner* — Nathan W Schlientz
(74) *Attorney, Agent, or Firm* — NKL Law; Allen Xue

(57) ABSTRACT

An alkene-containing amide compound of formula (I) and agriculturally acceptable salts thereof can be used as herbicides.

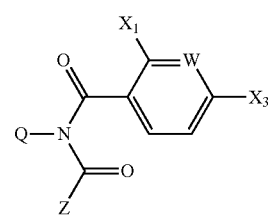

9 Claims, No Drawings

ALKENE-CONTAINING AMIDE COMPOUND AND APPLICATION THEREOF

TECHNICAL FIELD

The present invention belongs to the field of herbicides, and particularly relates to an alkene-containing amide compound and an application thereof as a herbicide.

BACKGROUND

Due to the succession and change of weed populations and the emergence and rapid development of resistance to chemical pesticides, people have continuously strengthened awareness on ecological environmental protection, and have paid more attention to the knowledge of chemical pesticide pollution and the influence of pesticides on non-target organisms and the end-result problem in the pesticide ecological environment. With the gradual decrease of the arable land area in the world, the continuous increase of the population and the increase of the demands for food, people are forced to rapidly develop agricultural production technologies, enhance and improve the farming system, and continuously invent novel and improved herbicidal compounds and compositions.

CN108290846A has reported that some benzamide compounds have herbicidal activity, such as compounds 13-30 (KC):

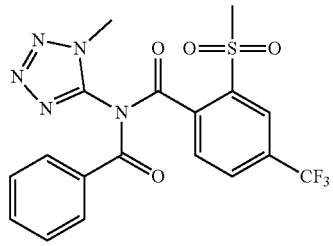

KC

The alkene-containing amide compound shown in the present invention is not disclosed.

SUMMARY

The purpose of the present invention is to provide an alkene-containing amide compound with novel structure and safety for crops and an application thereof as a herbicide.

To achieve the above purpose, the present invention adopts the following technical solution:

An alkene-containing amide compound is shown in formula I:

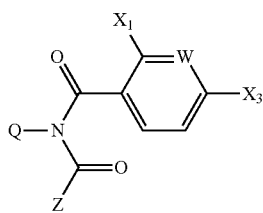

I

In the formula:

$X_1$ and $X_3$ are independently selected from hydrogen, cyano, nitro, halogen, $C_1$-$C_6$ alkylsulfonyl, $C_1$-$C_6$ haloalkylsulfonyl, $C_1$-$C_6$ alkylsulfinyl, $C_1$-$C_6$ haloalkylsulfinyl, $C_1$-$C_6$ alkylthio, $C_1$-$C_6$ haloalkylthio, $C_1$-$C_6$ alkyl, $C_1$-$C_6$ haloalkyl, $C_1$-$C_6$ alkoxy, $C_1$-$C_6$ haloalkoxy, $C_1$-$C_3$ alkyl, $C_1$-$C_6$ alkoxy $C_1$-$C_3$ alkoxy, $C_1$-$C_6$ alkoxy $C_1$-$C_3$ alkyl, $C_3$-$C_6$ cycloalkyl, $C_3$-$C_6$ cycloalkyl $C_1$-$C_3$ alkyl, $C_3$-$C_6$ cycloalkyl $C_1$-$C_3$ alkoxy, $C_3$-$C_6$ cycloalkyloxy, $C_2$-$C_6$ alkenyl, $C_2$-$C_6$ alkynyl, phenyl, $C_2$-$C_6$ alkenylsulfonyl, $C_2$-$C_6$ alkynylsulfonyl, phenylsulfonyl, $C_2$-$C_6$ alkenyloxy, $C_2$-$C_6$ alkynyloxy, phenyloxy, $C_2$-$C_6$ alkenylthio, $C_2$-$C_6$ alkynylthio, phenylthio, 5-7 membered aliphatic heterocycle containing 1-4 heteroatoms, 5-7 membered aromatic heterocycle containing 1-4 heteroatoms, 5-7 membered aliphatic heterocyclic $C_1$-$C_6$ alkyl containing 1-4 heteroatoms or 5-7 membered aromatic heterocyclic $C_1$-$C_6$ alkyl containing 1-4 heteroatoms; hydrogen on the phenyl, the aliphatic heterocycle and the aromatic heterocycle mentioned above may be substituted by one or more of the following substituents which are selected from nitro, halogen, $C_1$-$C_6$ alkyl, $C_1$-$C_6$ haloalkyl, $C_1$-$C_6$ alkoxy, $C_1$-$C_6$ haloalkoxy or $C_3$-$C_6$ cycloalkyl;

W is selected from N or $CX_2$;

$X_2$ is selected from hydrogen, cyano, nitro, halogen, $C_1$-$C_6$ alkyl, $C_1$-$C_6$ haloalkyl, $C_3$-$C_6$ cycloalkyl, $C_3$-$C_6$ cycloalkyl $C_1$-$C_6$ alkyl, $C_3$-$C_6$ halocycloalkyl $C_1$-$C_6$ alkyl, $Y_1$ oxy, $Y_1$ thio, $Y_1Y_2$ amino, $Y_1$ sulfinyl, $Y_1$ sulfonyl, $Y_1$ oxy $C_1$-$C_6$ alkyl, $Y_1$ thio $C_1$-$C_6$ alkyl, $Y_1Y_2$ amino $C_1$-$C_6$ alkyl, $Y_1$ sulfinyl $C_1$-$C_6$ alkyl, $Y_1$ sulfonyl $C_1$-$C_6$ alkyl, $C(O)Y_1$, $C(O)OY_1$, $OC(O)OY_1$, $N(Y_1)C(O)OY_2$, $C(O)N(Y_1)Y_2$, $N(Y_1)C(O)N(Y_1)Y_2$, $OC(O)N(Y_1)Y_2$, $C(O)N(Y_1)OY_2$, $N(Y_1)S(O)_2Y_2$, $N(Y_1)C(O)Y_2$, $OS(O)_2Y_1$, $CH=NOY_1$, $C_1$-$C_6$ alkyl-$CH=NOY_1$, $C_1$-$C_6$ alkyl-O—N$=C(Y_1)Y_2$, phenyl, 5-7 membered aliphatic heterocycle containing 1-4 heteroatoms, 5-7 membered aromatic heterocycle containing 1-4 heteroatoms, 5-7 membered aliphatic heterocyclic $C_1$-$C_6$ alkyl containing 1-4 heteroatoms or 5-7 membered aromatic heterocyclic $C_1$-$C_6$ alkyl containing 1-4 heteroatoms; the hydrogen on the phenyl, the aliphatic heterocycle and the aromatic heterocycle mentioned above may be substituted by one or more of the following substituents which are selected from nitro, halogen, $C_1$-$C_6$ alkyl, $C_1$-$C_6$ haloalkyl, $C_1$-$C_6$ alkoxy, $C_1$-$C_6$ haloalkoxy, $C_3$-$C_6$ cycloalkyl, $C_3$-$C_6$ cycloalkoxy, $C_2$-$C_6$ alkenyl, $C_2$-$C_6$ alkynyl, phenyl or halophenyl;

$Y_1$ and $Y_2$ are independently selected from $C_1$-$C_6$ alkyl, $C_1$-$C_6$ haloalkyl. $C_3$-$C_6$ cycloalkyl, $C_3$-$C_6$ cycloalkyl $C_1$-$C_6$ alkyl, $C_1$-$C_6$ alkoxy $C_1$-$C_6$ alkyl, phenyl, 5-7 membered aliphatic heterocycle containing 1-4 heteroatoms, 5-7 membered aromatic heterocycle containing 1-4 heteroatoms, 5-7 membered aliphatic heterocyclic $C_1$-$C_6$ alkyl containing 1-4 heteroatoms or 5-7 membered aromatic heterocyclic $C_1$-$C_6$ alkyl containing 1-4 heteroatoms; the hydrogen on the phenyl, the aliphatic heterocycle and the aromatic heterocycle mentioned above may be substituted by one or more of the following substituents which are selected from nitro, halogen. $C_1$-$C_6$ alkyl, $C_1$-$C_6$ haloalkyl, $C_1$-$C_6$ alkoxy, $C_1$-$C_6$ haloalkoxy, $C_3$-$C_6$ cycloalkyl, $C_3$-$C_6$ cycloalkoxy, $C_2$-$C_6$ alkenyl, $C_2$-$C_6$ alkynyl, phenyl or halophenyl;

Z is selected from $Z_1$ or $Z_2$ group;

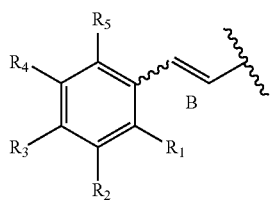

$Z_2$ is selected from $C_3$-$C_8$ ycloalkenyl; the hydrogen on the ring can be substituted by the following substituents; the following substituents are selected from nitro, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkenyl or $C_3$-$C_6$ cycloalkyl;

Q is selected from $Q_1$, $Q_2$, $Q_3$, $Q_4$, $Q_5$ or $Q_6$ group;

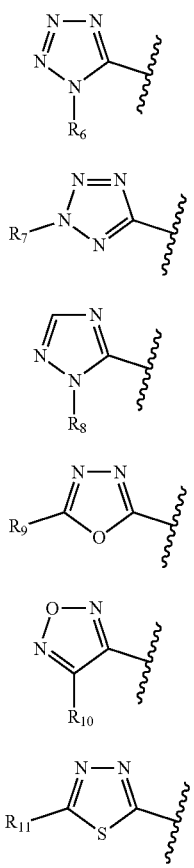

$R_1$ to $R_5$ are independently selected from hydrogen, hydroxyl, cyano, nitro, halogen, phenyl, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_1$-$C_6$ alkoxy, $C_1$-$C_6$ haloalkoxy, $C_1$-$C_6$ alkylthio or benzyloxy, wherein $R_1$ and $R_2$ form a benzene ring, a 5-7 membered aliphatic heterocycle containing 1-4 heteroatoms or a 5-7 membered aromatic heterocycle containing 1-4 heteroatoms together with the carbon atoms on the connected benzene ring;

$R_2$ and $R_3$ can form a benzene ring, a 5-7 membered aliphatic heterocycle containing 1-4 heteroatoms or a 5-7 membered aromatic heterocycle containing 1-4 heteroatoms together with the carbon atoms on the connected benzene ring;

$R_6$, $R_7$ and $R_8$ are independently selected from hydrogen, $C_1$-$C_6$ alkyl, $C_1$-$C_6$ haloalkyl, $C_3$-$C_6$ cycloalkyl, $C_3$-$C_6$ cycloalkyl $C_1$-$C_6$ alkyl, $C_2$-$C_6$ alkenyl, $C_2$-$C_6$ alkynyl or phenyl;

$R_9$, $R_{10}$ and $R_{11}$ are independently selected from hydrogen, halogen, cyano, nitro, $C_1$-$C_6$ alkylsulfonyl, $C_1$-$C_6$ haloalkylsulfonyl, $C_1$-$C_6$ alkylsulfinyl, $C_1$-$C_6$ haloalkylsulfinyl, $C_1$-$C_6$ alkylthio, $C_1$-$C_6$ haloalkylthio, $C_1$-$C_6$ alkyl, $C_1$-$C_6$ haloalkyl, $C_1$-$C_6$ alkoxy, $C_1$-$C_6$ haloalkoxy, $C_1$-$C_3$ alkoxy $C_1$-$C_3$ alkyl, $C_1$-$C_6$ alkoxy $C_1$-$C_3$ alkoxy, $C_1$-$C_6$ alkoxy $C_1$-$C_3$ alkoxy $C_1$-$C_3$ alkyl, $C_3$-$C_6$ cycloalkyl, $C_3$-$C_6$ cycloalkyl $C_1$-$C_3$ alkyl, $C_3$-$C_6$ cycloalkyl $C_1$-$C_3$ alkoxy or $C_3$-$C_6$ cycloalkyloxy;

a stereoisomer of the compound of the above formula I; or, the compound of the formula I and agriculturally acceptable salt of the isomer.

Preferably, in the compound, wherein in the formula I:

$X_1$ and $X_3$ are independently selected from hydrogen, cyano, nitro, halogen, $C_1$-$C_6$ alkylsulfonyl, $C_1$-$C_6$ alkylsulfinyl, $C_1$-$C_6$ alkylthio, $C_1$-$C_6$ haloalkylthio, $C_1$-$C_6$ alkyl, $C_1$-$C_6$ haloalkyl, $C_1$-$C_6$ alkoxy, $C_1$-$C_6$ alkoxy $C_1$-$C_3$ alkyl, $C_1$-$C_6$ alkoxy $C_1$-$C_3$ alkoxy, $C_1$-$C_6$ alkoxy $C_1$-$C_3$ alkoxy $C_1$-$C_3$ alkyl, $C_3$-$C_6$ cycloalkyl, $C_3$-$C_6$ cycloalkyl $C_1$-$C_3$ alkyl, $C_3$-$C_6$ cycloalkyl, $C_1$-$C_3$ alkoxy, $C_3$-$C_6$ cycloalkyloxy. $C_2$-$C_6$ alkenyloxy, $C_2$-$C_6$ alkenyl, $C_2$-$C_6$ alkynyl, phenyl, phenylsulfonyl, phenyloxy, a 5-7 membered aliphatic heterocycle containing 1-4 heteroatoms and a 5-7 membered aromatic heterocycle containing 1-4 heteroatoms; the hydrogen on the phenyl, the aliphatic heterocycle and the aromatic heterocycle mentioned above may be substituted by one or more of the following substituents which are selected from nitro, halogen, $C_1$-$C_6$ alkyl, $C_1$-$C_6$ haloalkyl, $C_1$-$C_6$ alkoxy, $C_1$-$C_6$ haloalkoxy or $C_3$-$C_6$ cycloalkyl;

W is selected from N or $CX_2$;

$X_2$ is selected from hydrogen, cyano, nitro, halogen, $C_1$-$C_6$ alkyl, $C_1$-$C_6$ haloalkyl, $C_3$-$C_6$ cycloalkyl, $C_3$-$C_6$ cycloalkyl $C_1$-$C_6$ alkyl, $C_3$-$C_6$ halocycloalkyl $C_1$-$C_6$ alkyl, $Y_1$ oxy, $Y_1$ thio, $Y_1Y_2$ amino, $Y_1$ sulfinyl, $Y_1$ sulfonyl, $Y_1$ oxy $C_1$-$C_6$ alkyl, $Y_1$ thio $C_1$-$C_6$ alkyl, $Y_1Y_2$ amino $C_1$-$C_6$ alkyl, $Y_1$ sulfinyl $C_1$-$C_6$ alkyl, $Y_1$ sulfonyl $C_1$-$C_6$ alkyl, C(O)$Y_1$, C(O)O$Y_1$, OC(O)O$Y_1$, N($Y_1$)C(O)O$Y_2$, C(O)N($Y_1$)$Y_2$, N($Y_1$)C(O)N($Y_1$)$Y_2$, OC(O)N($Y_1$)$Y_2$, C(O)N($Y_1$)O$Y_2$, N($Y_1$)S(O)$_2Y_2$, N($Y_1$)C(O)$Y_2$, OS(O)$_2Y_1$, CH=NO$Y_1$, $C_1$-$C_6$ alkyl-CH=NO$Y_1$, $C_1$-$C_6$ alkyl-O—N=C($Y_1$)$Y_2$, phenyl, 5-7 membered aliphatic heterocycle containing 1-4 heteroatoms, 5-7 membered aromatic heterocycle containing 1-4 heteroatoms, 5-7 membered aliphatic heterocyclic $C_1$-$C_6$ alkyl containing 1-4 heteroatoms or 5-7 membered aromatic heterocyclic $C_1$-$C_6$ alkyl containing 1-4 heteroatoms; the hydrogen on the phenyl, the aliphatic heterocycle and the aromatic heterocycle mentioned above may be substituted by one or more of the following substituents which are selected from nitro, halogen, $C_1$-$C_6$ alkyl, $C_1$-$C_6$ haloalkyl, $C_1$-$C_6$ alkoxy, $C_1$-$C_6$ haloalkoxy, $C_3$-$C_6$ cycloalkyl or $C_3$-$C_6$ cycloalkoxy;

$Y_1$ and $Y_2$ are independently selected from $C_1$-$C_6$ alkyl, $C_1$-$C_6$ haloalkyl, $C_3$-$C_6$ cycloalkyl, $C_3$-$C_6$ cycloalkyl $C_1$-$C_6$ alkyl, $C_1$-$C_6$ alkoxy $C_1$-$C_6$ alkyl, phenyl, a 5-7 membered aliphatic heterocycle containing 1-4 heteroatoms, a 5-7 membered aromatic heterocycle containing 1-4 heteroatoms, a 5-7 membered aliphatic heterocyclic $C_1$-$C_6$ alkyl containing 1-4 heteroatoms or a 5-7 membered aromatic heterocyclic $C_1$-$C_6$ alkyl containing 1-4 heteroatoms; the hydrogen on the phenyl, the aliphatic heterocycle and the aromatic heterocycle mentioned above may be substituted by one or more of the following substituents which are selected from nitro, halogen, $C_1$-$C_6$ alkyl, $C_1$-$C_6$ haloalkyl, $C_1$-$C_6$ alkoxy, $C_1$-$C_6$ haloalkoxy, $C_3$-$C_6$ cycloalkyl or $C_3$-$C_6$ cycloalkoxy;

Z is selected from $Z_1$ or $X_2$ group;

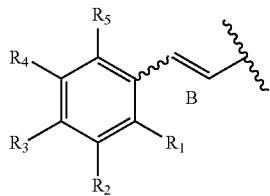

$Z_2$ is selected from $C_3$-$C_8$ cycloalkenyl; the hydrogen on the ring can be substituted by the following substituents; the following substituents are selected from nitro, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkenyl or $C_3$-$C_6$ cycloalkyl;

Q is selected from $Q_1$, $Q_2$, $Q_3$, $Q_4$ or $Q_5$ group;

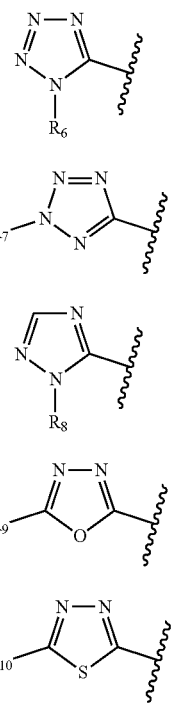

$R_1$ to $R_5$ are independently selected from hydrogen, hydroxyl, cyano, nitro, halogen, phenyl, $C_1$-$C_6$ alkyl, $C_2$-$C_6$ alkenyl, $C_2$-$C_6$, alkynyl, $C_1$-$C_6$ alkoxy, $C_1$-$C_6$ alkylthio or benzyloxy, wherein $R_1$ and $R_2$ form a benzene ring, a 5-7 membered aliphatic heterocycle containing 1-4 heteroatoms or a 5-7 membered aromatic heterocycle containing 1-3 heteroatoms together with the carbon atoms on the connected benzene ring;

$R_2$ and $R_3$ can form a benzene ring, a 5-7 membered aliphatic heterocycle containing 1-4 heteroatoms or a 5-7 membered aromatic heterocycle containing 1-3 heteroatoms together with the carbon atoms on the connected benzene ring;

$R_6$, $R_7$ and $R_8$ are independently selected from hydrogen, $C_1$-$C_6$ alkyl, $C_3$-$C_6$ cycloalkyl, $C_2$-$C_6$ alkenyl, $C_2$-$C_6$ alkynyl or phenyl;

$R_9$ and $R_{10}$ are independently selected from hydrogen, halogen, $C_1$-$C_6$ alkylthio, $C_1$-$C_6$ alkyl, $C_1$-$C_6$ alkoxy, $C_1$-$C_3$ alkoxy $C_1$-$C_3$ alkyl, $C_1$-$C_6$ alkoxy $C_1$-$C_3$ alkoxy, $C_1$-$C_6$ alkoxy $C_1$-$C_3$ alkoxy $C_1$-$C_3$ alkyl or $C_3$-$C_6$ cycloalkyl;

the Z of the above formula I is selected from the stereoisomer of the compound shown by $Z_1$.

Further preferably, in the compound, wherein in the formula $X_1$ and $X_3$ are independently selected from hydrogen, cyano, nitro, halogen, $C_1$-$C_3$ alkylsulfonyl, $C_1$-$C_3$ alkylsulfinyl, $C_1$-$C_3$ alkylthio, $C_1$-$C_3$ haloalkylthio, $C_1$-$C_3$ alkyl, $C_1$-$C_3$ haloalkyl, $C_1$-$C_3$ alkoxy, $C_1$-$C_3$ alkoxy $C_1$-$C_3$ alkyl, $C_1$-$C_3$ alkoxy $C_1$-$C_3$ alkoxy, $C_1$-$C_3$ alkoxy $C_1$-$C_3$ alkoxy $C_1$-$C_3$ alkyl, $C_3$-$C_6$ cycloalkyl or $C_3$-$C_6$ cycloalkyloxy;

W is selected from N or $CX_2$;

$X_2$ is selected from hydrogen, cyano, nitro, halogen, $C_1$-$C_3$ alkyl, $C_1$-$C_3$ haloalkyl, $C_3$-$C_6$ cycloalkyl, $C_3$-$C_6$ cycloalkyl $C_1$-$C_3$ alkyl, $C_3$-$C_6$ halocycloalkyl $C_1$-$C_3$ alkyl, $Y_1$ oxy, $Y_1$ thio, $Y_1Y_2$ amino, $Y_1$ sulfinyl, $Y_1$ sulfonyl, $Y_1$ oxy $C_1$-$C_3$ alkyl, $Y_1$ thio $C_1$-$C_3$ alkyl, $Y_1Y_2$ amino $C_1$-$C_3$ alkyl, $Y_1$ sulfinyl $C_1$-$C_3$ alkyl, $Y_1$ sulfonyl $C_1$-$C_3$ alkyl, $C(O)Y_1$, $C(O)OY_1$, $OC(O)OY_1$, $N(Y_1)C(O)OY_2$, $C(O)N(Y_1)Y_2$, $N(Y_1)C(O)N(Y_1)Y_2$, $OC(O)N(Y_1)Y_2$, $C(O)N(Y_1)OY_2$, $N(Y_1)S(O)_2Y_2$, $N(Y_1)C(O)Y_2$, $OS(O)_2Y_1$, $CH=NOY_1$, $C_1$-$C_6$ alkyl-$CH=NOY_1$, $C_1$-$C_6$ alkyl-O—$N=C(Y_1)Y_2$, phenyl, 5-7 membered aliphatic heterocycle containing 1-4 heteroatoms, 5-7 membered aromatic heterocycle containing 1-4 heteroatoms, 5-7 membered aliphatic heterocyclic $C_1$-$C_3$ alkyl containing 1-4 heteroatoms or 5-7 membered aromatic heterocyclic $C_1$-$C_3$ alkyl containing 1-4 heteroatoms; the hydrogen on the phenyl, the aliphatic heterocycle and the aromatic heterocycle mentioned above may be substituted by one or more of the following substituents which are selected from nitro, halogen, $C_1$-$C_3$ alkyl, $C_1$-$C_3$ haloalkyl, $C_1$-$C_3$ alkoxy, $C_3$-$C_6$ cycloalkyl or $C_3$-$C_6$ cycloalkoxy;

$Y_1$ and $Y_2$ are independently selected from $C_1$-$C_6$ alkyl, $C_1$-$C_6$ haloalkyl, $C_3$-$C_6$ cycloalkyl, $C_3$-$C_6$ cycloalkyl $C_1$-$C_6$ alkyl, $C_1$-$C_6$ alkoxy $C_1$-$C_6$ alkyl, phenyl, a 5-7 membered aliphatic heterocycle containing 1-4 heteroatoms, a 5-7 membered aromatic heterocycle containing 1-4 heteroatoms, a 5-7 membered aliphatic heterocyclic $C_1$-$C_6$ alkyl containing 1-4 heteroatoms or a 5-7 membered aromatic heterocyclic $C_1$-$C_6$ alkyl containing 1-4 heteroatoms; the hydrogen on the phenyl, the aliphatic heterocycle, and the aromatic heterocycle may be substituted by one or more of the following substituents which are selected from nitro, halogen, $C_1$-$C_6$ alkyl, $C_1$-$C_6$ haloalkyl, $C_1$-$C_6$ alkoxy, $C_1$-$C_6$ haloalkoxy, $C_3$-$C_6$ cycloalkyl or $C_3$-$C_6$ cycloalkoxy;

Z is selected from $Z_1$ or $Z_2$ group;

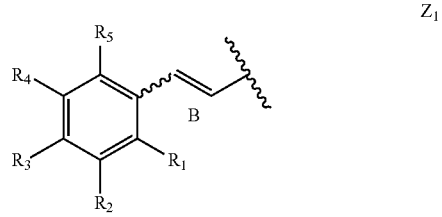

$Z_2$ is selected from $C_5$-$C_6$ cycloalkenyl; the hydrogen on the ring may be substituted by the following substituents which are selected from $C_1$-$C_6$ alkyl, $C_1$-$C_6$ alkoxy or $C_1$-$C_6$ alkenyl;

Q is selected from $Q_3$, $Q_2$, $Q_3$ or $Q_4$ group;

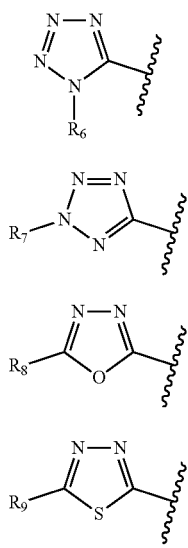

$R_1$ to $R_5$ are independently selected from hydrogen, hydroxyl, cyano, nitro, halogen, phenyl, $C_1$-$C_6$ alkyl, $C_2$-$C_6$ alkenyl, $C_2$-$C_6$ alkynyl, $C_1$-$C_6$ alkoxy or benzyloxy, wherein $R_1$ and $R_2$ form a benzene ring or a 5-7 membered aliphatic heterocycle containing 1-4 heteroatoms together with the carbon atoms on the connected benzene ring;

$R_2$ and $R_3$ can form a benzene ring or a 5-7 membered aliphatic heterocycle containing 1-4 heteroatoms together with the carbon atoms on the connected benzene ring;

$R_6$ and $R_7$ are independently selected from hydrogen, $C_1$-$C_6$ alkyl, $C_2$-$C_6$ alkenyl or phenyl;

$R_8$ and $R_9$ are independently selected from hydrogen, halogen, $C_1$-$C_6$ alkyl, $C_1$-$C_6$ alkoxy, $C_1$-$C_3$ alkoxy $C_1$-$C_3$ alkyl, $C_1$-$C_6$ alkoxy $C_1$-$C_3$ alkoxy or $C_3$-$C_6$ cycloalkyl;

the Z of the above formula I is selected from the stereoisomer of the compound shown by $Z_1$.

More further preferably, in the compound, wherein in the formula I:

$X_1$ and $X_3$ are independently selected from hydrogen, cyano, nitro, halogen, $C_1$-$C_3$ alkylsulfonyl, $C_1$-$C_3$ alkyl and $C_1$-$C_3$ haloalkyl;

W is selected from N or $CX_2$;

$X_2$ is selected from hydrogen, halogen, $C_1$-$C_3$ alkyl, $C_1$-$C_3$ haloalkyl, $C_3$-$C_6$ cycloalkyl, $C_3$-$C_6$ cycloalkyl $C_1$-$C_3$ alkyl, $C_3$-$C_6$ halocycloalkyl $C_1$-$C_3$ alkyl, $Y_1$ oxy, $Y_1$ thio, $Y_1Y_2$ amino, $Y_1$ sulfonyl, $Y_1$ oxy $C_1$-$C_3$ alkyl, $Y_1$ thio $C_1$-$C_3$ alkyl, $Y_1Y_2$ amino $C_1$-$C_3$ alkyl, $Y_1$ sulfonyl $C_1$-$C_3$ alkyl, $C(O)Y_1$, $C(O)OY_1$, $OC(O)OY_1$, $N(Y_1)C(O)OY_2$, $C(O)N(Y_1)Y_2$, $N(Y_1)C(O)N(Y_1)Y_2$, $OC(O)N(Y_1)Y_2$, $C(O)N(Y_1)OY_2$, $N(Y_1)S(O)_2Y_2$, $N(Y_1)C(O)Y_2$, $OS(O)_2Y_1$, $CH=NOY_1$, $C_1$-$C_6$ alkyl-$CH=NOY_1$, $C_1$-$C_6$ alkyl-O—N=C($Y_1$)$Y_2$, phenyl, 5-7 membered aliphatic heterocycle containing 1-4 heteroatoms, 5-7 membered aromatic heterocycle containing 1-4 heteroatoms, 5-7 membered aliphatic heterocyclic $C_1$-$C_3$ alkyl containing 1-4 heteroatoms or 5-7 membered aromatic heterocyclic $C_1$-$C_3$ alkyl containing 1-4 heteroatoms; the hydrogen on the phenyl, the aliphatic heterocycle and the aromatic heterocycle mentioned above may be substituted by one or more of the following substituents which are selected from nitro, halogen, $C_1$-$C_3$ alkyl, $C_1$-$C_3$ haloalkyl, $C_1$-$C_3$ alkoxy, $C_3$-$C_6$ cycloalkyl or $C_3$-$C_6$ cycloalkoxy;

$Y_1$ and $Y_2$ are independently selected from $C_1$-$C_6$ alkyl, $C_1$-$C_6$ haloalkyl, $C_3$-$C_6$ cycloalkyl, $C_3$-$C_6$ cycloalkyl $C_1$-$C_6$ alkyl, $C_1$-$C_6$ alkoxy $C_1$-$C_6$ alkyl, phenyl, a 5-7 membered aliphatic heterocycle containing 1-4 heteroatoms, a 5-7 membered aromatic heterocycle containing 1-4 heteroatoms, a 5-7 membered aliphatic heterocyclic $C_1$-$C_6$ alkyl containing 1-4 heteroatoms or a 5-.7 membered aromatic heterocyclic $C_1$-$C_6$ alkyl containing 1-4 heteroatoms; the hydrogen on the phenyl, the aliphatic heterocycle and the aromatic heterocycle mentioned above may be substituted by one or more of the following substituents which are selected from nitro, halogen, $C_1$-$C_6$ alkyl, $C_1$-$C_6$ haloalkyl, $C_1$-$C_6$ alkoxy, $C_1$-$C_6$ haloalkoxy, $C_3$-$C_6$ cycloalkyl or $C_3$-$C_6$ cycloalkoxy;

Z is selected from $Z_1$ or $Z_2$ group;

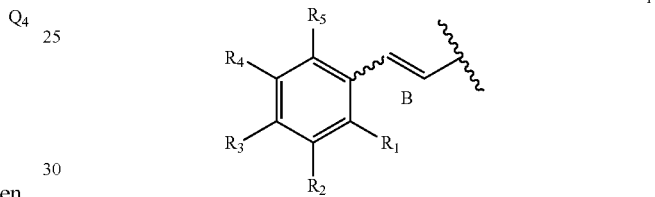

$Z_2$ is selected from $G_1$, $G_2$, $G_3$, $G_4$, $G_5$ or $G_6$ group;

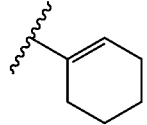

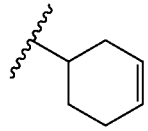

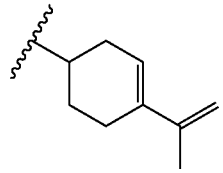

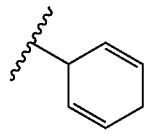

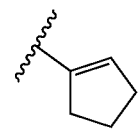

-continued

G₆

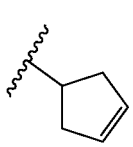

Q is selected from Q₁, Q₂, Q₃ or Q₄ group;

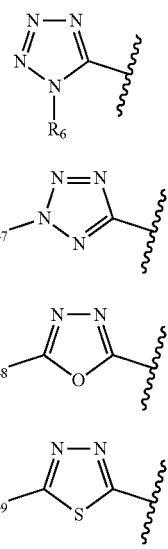

R₁ to R₅ are independently selected from hydrogen, hydroxyl, cyano, nitro, halogen, phenyl, methyl, ethyl, propyl, vinyl, propenyl, ethynyl, propynyl, methoxy, ethoxyl, benzyloxy, trifluoromethyl or trifluoromethoxy;

R₁ and R₂ can form a benzene ring together with the carbon atoms on the connected benzene ring;

R₂ and R₃ can form a benzene ring, 1,3-dioxane ring or 1,4-dioxane ring together with the carbon atoms on the connected benzene ring;

R₆ and R₇ are independently selected from hydrogen, methyl or ethyl;

R₈ and R₉ are independently selected from hydrogen, chlorine or methyl;

the Z of the above formula I is selected from a trans-stereoisomer of the compound shown by Z₁.

In the definitions of the compounds of the formula I provided above, the terms used in the collection are defined as follows:

Alkyl refers to linear or branched groups such as methyl, ethyl, n-propyl, isopropyl, n-butyl, isobutyl, sec-butyl, tert-butyl, n-pentyl, isopentyl, n-hexyl and so on. Cycloalkyl refers to groups in the form of cyclic chain, such as cyclopropyl, methylcyclopropyl, cyclopropylcyclopropyl, cyclobutyl, cyclopentyl and cyclohexyl and so on, Alkenyl refers to linear or branched alkenyl, such as vinyl, 1-propenyl, 2-propenyl, butenyl, pentenyl and hexenyl and so on. Alkynyl refers to linear or branched chain alkynyl, such as 1-propynyl, 2-propynyl, butynyl, pentynyl and hexynyl and so on. Alkoxy refers to a group having an oxygen atom at the end of the alkyl, such as methoxy, ethoxy, n-propoxy, isopropoxy and tert-butoxy and so on. The 5-7-membered heterocycle containing 1-4 heteroatoms refers to a 5-7-membered heterocyclic compound containing 1-4 heteroatoms without aromatic characteristics, such as ethylene oxide, tetrahydrofuran, imidazolinone, caprolactam, 1,3-dioxane ring and 1,4-dioxane ring and so on. The 5-7-membered aromatic heterocycle containing 1-4 heteroatoms refers to a 5-7-membered heterocyclic compound containing 1-4 heteroatoms having aromatic characteristics, such as furan, thiophene, pyrazole and pyridine and so on. Stereoisomers mean that hydrogen atoms on the carbon-carbon double bond B in the formula I are on the same side (cis) or on both sides (trans) of the bond B.

The compound I of the formula in the present invention can be prepared by the following method:

Method I:

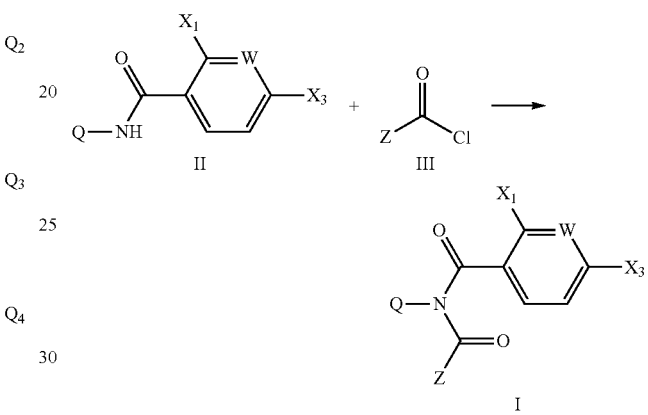

The compound of the formula II and the compound of the formula III react in a suitable solvent at temperature of −10° C. to a boiling point of the suitable solvent for 0.5-48 hours to obtain a target compound I.

The suitable solvent is selected from dichloromethane, 1,2-dichloroethane, chloroform, carbon tetrachloride, hexane, benzene, toluene, ethyl acetate, acetonitrile, acetic acid, tetrahydrofuran, dioxane, N,N-dimethylformamide or dimethylsulfoxide and so on.

Addition of a suitable alkali substance in the reaction system can be beneficial to the reaction. The suitable alkali is selected from organic alkali such as triethylamine, N,N-dimethylaniline or pyridine and so on, or inorganic alkali such as sodium hydroxide, potassium hydroxide, sodium carbonate, sodium bicarbonate, potassium carbonate, sodium methoxide, sodium tert-butoxide or potassium tert-butoxide and so on.

The compound of the formula III can be prepared from the corresponding acid (commercially available) by reference to WO2009123714.

Method II:

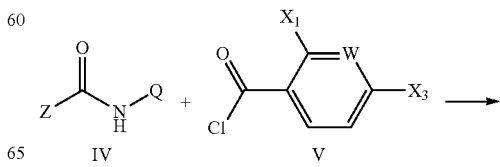

-continued

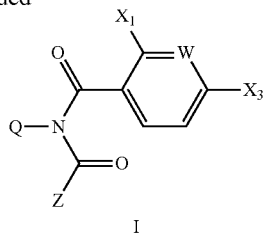

I

The compound of the formula IV and the compound of the formula V react in a suitable solvent at temperature of −10° C. to a boiling point of the suitable solvent for 0.5-48 hours to obtain a target compound I.

The suitable solvent is selected from dichloromethane, 1,2-dichloroethane, chloroform, carbon tetrachloride, hexane, benzene, toluene, ethyl acetate, acetonitrile, acetic acid, tetrahydrofuran, dioxane, N,N-dimethylformamide or dimethylsulfoxide and so on.

Addition of a suitable alkali substance in the reaction system can be beneficial to the reaction. The suitable alkali is selected from organic alkali such as triethylamine, N,N-dimethylaniline or pyridine and so on, or inorganic alkali such as sodium hydroxide, potassium hydroxide, sodium carbonate, sodium bicarbonate, potassium carbonate, sodium methoxide, sodium tert-butoxide or potassium tert-butoxide and so on.

The compound of the formula V can be prepared from the corresponding acid (commercially available) by reference to WO2009123714.

The preparation method of the compound of the formula II is as follows:

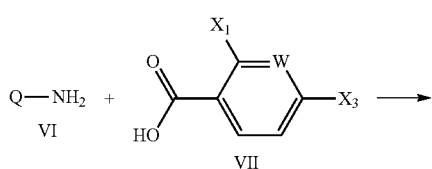

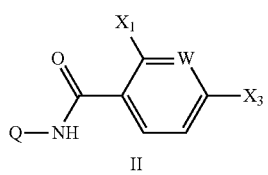

II

The compound of the formula VI (commercially available) and the compound of the formula VII (commercially available) react with a suitable activator in suitable alkali and solvent at temperature of -10° C. to a boiling point of the suitable solvent for 0.5-48 hours to obtain the compound of the formula II. The suitable solvent is selected from petroleum ether, hexane, benzene, toluene, chlorobenzene, ethyl acetate, acetonitrile, tetrahydrofuran, N, N-dimethylformamide, dimethylsulfoxide, pyridine, 2-methylpyridine, 3-methylpyridine or 4-methylpyridine and so on. The suitable activator is selected from phosgene, triphosgene, CDI, DCC, dichlorosulfoxide, oxalyl chloride, phosphorus oxychloride, or phosphorus pentachloride and so on. The suitable alkali is selected from N-methylimidazole or DMAP and so on.

The preparation method of the compound of the formula IV can be referred to the preparation method of the compound of the formula The compound of the formula I of the present invention and the stereoisomer thereof or the compound of the formula I and the agriculturally acceptable salt of the isomer have herbicidal activity and can be used for agriculturally controlling various weeds. Compared with the compound disclosed in the prior art, the alkene-containing amide compound of the present invention not only has excellent herbicidal activity, but also is safe for crops.

The present invention also comprises a herbicidal composition using the compound of the formula I and the stereoisomer thereof or the compound of the formula I and the agriculturally acceptable salt of the isomer as active ingredients. The weight percentage of the active ingredient in the herbicidal composition is 1-99%. The herbicidal composition also comprises an agriculturally acceptable carrier.

The herbicidal composition of the present invention can be applied in the forms of various formulations. The compound of the present invention is generally dissolved or dispersed in the carrier and prepared into the formulation for easier dispersion when used as a herbicide. For example, the chemical formulations can be prepared into wettable powder or missible oil. Therefore, in the compositions, at least one liquid or solid carrier is added, and generally a suitable surfactant needs to be added.

The present invention also provides an implementing method for controlling weeds. The method comprises applying an effective dose of the herbicidal composition of the present invention to the weed or a weed growing place or a surface of a growth medium thereof. A suitable effective dose is 1 to 1000 grams per hectare, and a preferred dfective dose is 10 to 500 grams per hectare. For some applications, one or more other herbicides can be added to the herbicidal composition of the present invention, thereby generating additional advantages and effects.

The compound of the present invention can be used alone or in combination with other known pesticides, bactericides, plant growth regulators or fertilizers.

It should be clear that various changes and modifications can be made within the scope defined by the claims of the present invention.

The present invention has the following advantages:

Compared with the known benzamide compound, the compound of the formula in the present invention comprises a benzoyl and an alkene-containing acyl substitution, and has a novel structure. The alkene-containing amide compound in the present invention has unexpectedly high herbicidal activity, also has high herbicidal activity at a lower dosage, not only has high efficiency, but also reduces the use amount of pesticides, reduces the cost and reduces environmental pollution.

DETAILED DESCRIPTION

The following examples and biometric test results can be used to further illustrate the present invention, but are not intended to limit the present invention.

SYNTHESIS EXAMPLE

Embodiment 1 Synthesis of Compound 1-1

(1) Synthesis of N-(1-methyl-tetrazole-5yl)-2-methanesulfonyl-4-trifluoromethylbenzamide

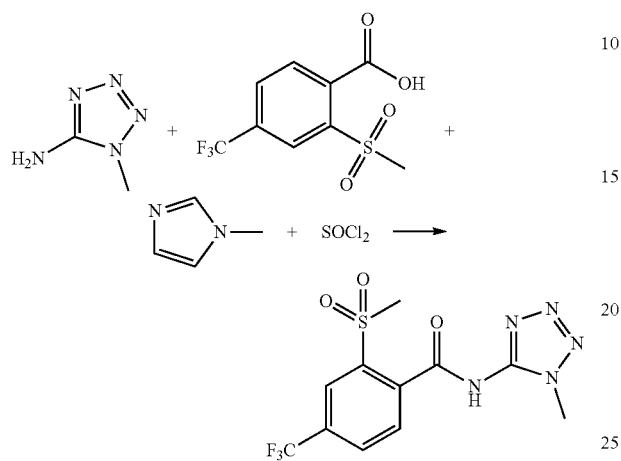

2-methanesulfonyl-4-trifluoromethylbenzoic acid (19.1 g, 71.2 mmol), 1-methyl-5-aminotetrazole (8.5 g, 85.4 mmol), 3-methylpyridine (100 ml) and N-methylimidazole (11.7 g, 142 mmol) were added to a reaction flask, stirred at room temperature for half an hour, and cooled to be below 10° C. in an ice-water bath; dichlorosuifoxide (13.6 g, 114.0 mmol) was slowly dripped; the mixture was stirred at room temperature for 2 hours, heated to 50° C. to preserve heat and react for 2 hours, and cooled to be below 10° C. in the ice-water bath; cold water was slowly dripped; solid precipitated out and was filtered; a filter cake was washed twice with 100 ml of water and dried to obtain 17.5 g of white solid, with a yield of 70%.

(2) Synthesis of Cinnamyl Chloride

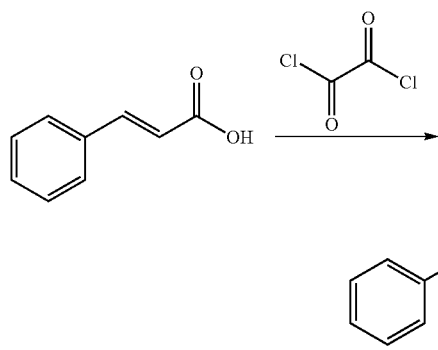

Cinnamic acid (10.0 g, 67.5 mmol), dichloromethane (300 ml) and DMF (3 drops) were added into the reaction flask; oxalyl chloride (42.8 g, 337.5 mmol) was slowly added; the mixture was stirred at room temperature for 2 hours; the solvent was evaporated under reduced pressure; toluene (150 ml) was added to the residue and stirred for 3 minutes; and then the solvent was evaporated under reduced pressure to obtain 11.3 g of yellow solid which was used directly in the next step.

(3) Synthesis of Compound 1-1

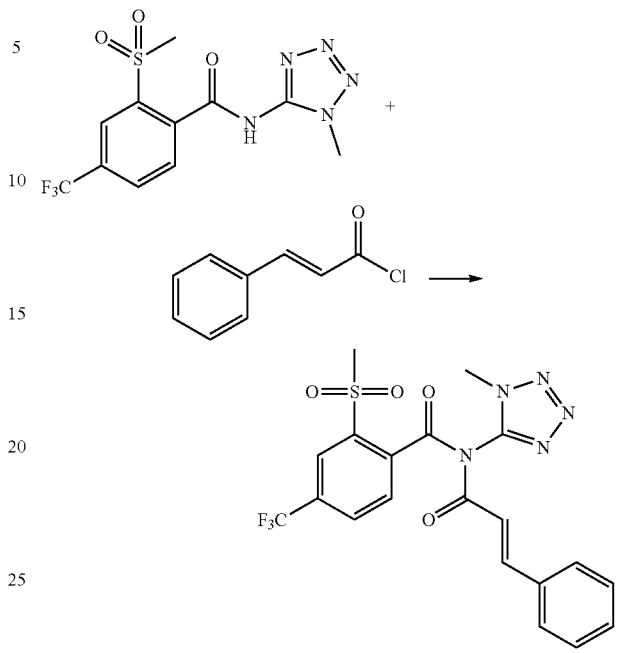

N-(1-methyl-tetrazole-5-yl) -2-methanesulfonyl-4-trifluoromethylbenzamide (1.2 g, 3.4 mmol), dichloromethane (20 ml) and triethylamine (0.7 g, 6.8 mmol) were added to the reaction flask, and the prepared dichloromethane solution of the cinnamyl chloride was dropwise added (the cinnamyl chloride (1.1 g, 6.8 mmol) was dissolved in 15 ml of dichloromethane). The mixture was stirred at room temperature for 40 minutes; the solvent was evaporated under reduced pressure; ethyl acetate (50 ml) was added to the residue; water (50 ml) was used for separation and extraction; the organic phase was washed with saturated salt water (50 ml) and dried with anhydrous magnesium sulfate; the solvent was evaporated under reduced pressure; and the residue was separated by column chromatography to obtain 1.3 g of pale yellow solid, with a purity of 94% and a yield of 82%.

Embodiment 2 Synthesis of Compound 2-265

(1) Synthesis of 1-cyclohexenoyl Chloride

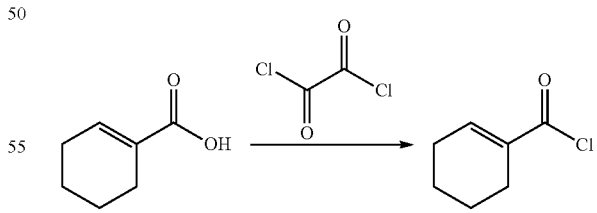

1-cyclohexenoic acid (0.36 g, 2.9 mmol), dichloromethane (30 ml) and DMF (1 drop) were added into the reaction flask; oxalyl chloride (1.82 g, 14.3 mmol) was slowly added; the mixture was stirred at room temperature for 1 hour; the solvent was evaporated under reduced pressure; toluene (15 ml) was added to the residue and stirred for 3 minutes; and then the solvent was evaporated under reduced pressure to obtain 0.42 g of pale yellow solid which was used directly in the next step.

(2) Synthesis of Compound 2-265

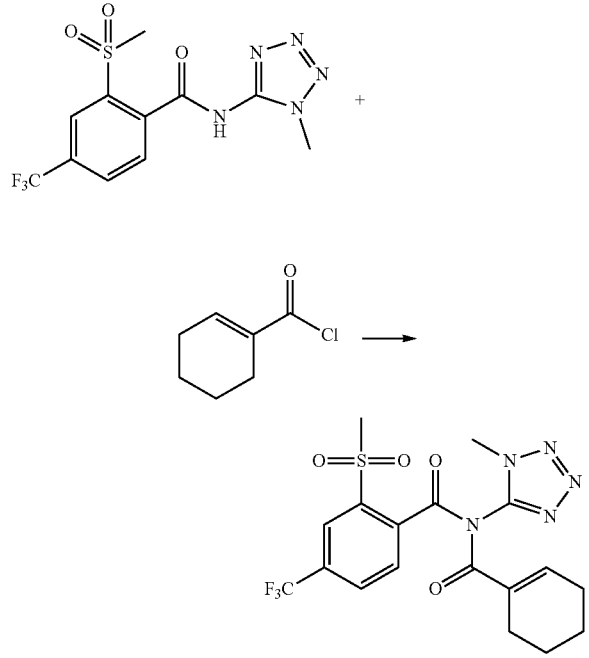

N-(1-methyl-tetrazole-5-yl) -2-methariesulfonyl-4-trifluoromethylbenzamide (0.5 g, 1.4 mmol, see step 3 of embodiment 1 for the preparation), dichloromethane (20 ml) and triethylamine (0.29 g, 2.9 mmol) were added to the reaction flask, and the dichloromethane solution (15 ml) of 1-cyclohexenoyl chloride in the above step was added dropwise. The mixture was stirred at room temperature for 1 hour; the solvent is evaporated under reduced pressure; ethyl acetate (100 ml) was added to the residue; water (50 ml) was used for separation and extraction; the organic phase was sequentially washed with saturated salt water (50 ml) and dried with anhydrous magnesium sulfate; the solvent was evaporated under reduced pressure; and the residue was separated by column chromatography to obtain 0.55 g of off-white solid compound 2-265, with a purity of 97.6% and a yield of 82%.

Embodiment 3 Synthesis of Compound 1-24

(1) Synthesis of N-(1-methyl-tetrazole-5-yl)-2-chloro-3-methoxymethyl-4-methanesulfonyl benzamide

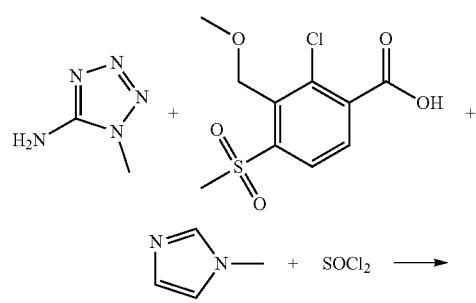

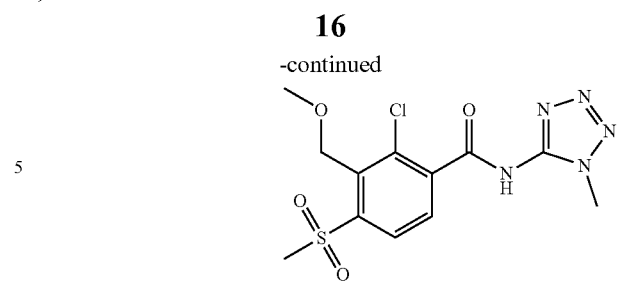

2-chloro-3-methoxymethyl-4-methanesulfonyl benzoic acid (5.0 g, 17.9 mmol), 1-methyl-5-aminotetra.zole (2.1 g, 21.5 mmol), 3-methylpyridine (30 ml) and N-methylitnidazole (3.0 g, 35.9 mmol) were added to the reaction flask, stirred at room temperature for half an hour, and cooled to be below 10° C. in an ice-water bath; dichlorosulfoxide (3.4 g, 28.7 mmol) was slowly dripped; the mixture was stirred at room temperature for 2 hours, heated to 50° C. to preserve heat and react for 2 hours, and cooled to be below 10° C. in the ice-water bath; cold water was slowly dripped; solid precipitated out and was filtered; a filter cake was washed twice with 30 ml of water and dried to obtain 3.29 g of off-white solid, with a yield of 51%.

(2) Synthesis of Compound 1-24

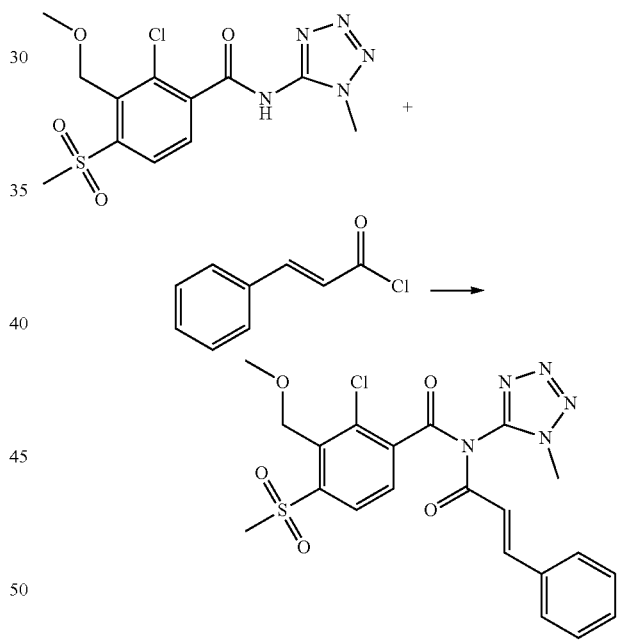

N-(1-methyl-tetrazole-5-yl)-2-chloro-3-methoxymethyl-4-methanesulfonyl benzamide (0.5 g, 1.4 mmol), dichloromethane (20 ml) and triethylamine (0.3 g, 2.8 mmol) were added to the reaction flask, and the prepared dichloromethane solution of the cinnamyl chloride was dropwise added (0.5 g of cinnamyl chloride was dissolved in 15 ml of dichloromethane). The mixture was stirred at room temperature for 40 minutes; the solvent was evaporated under reduced pressure; ethyl acetate (50 ml) was added to the residue; water (50 ml) was used for separation and extraction; the organic phase was washed with saturated salt water (50 ml) and dried with anhydrous magnesium sulfate; the solvent was evaporated under reduced pressure; and the residue was separated by column chromatography to obtain 0.4 g of pale yellow solid, with a purity of 95% and a yield of 56%.

Embodiment 4 Synthesis of Compound 1-41

(1) Synthesis of N-(1-methyl-tetrazole-5yl) Cinnamamide

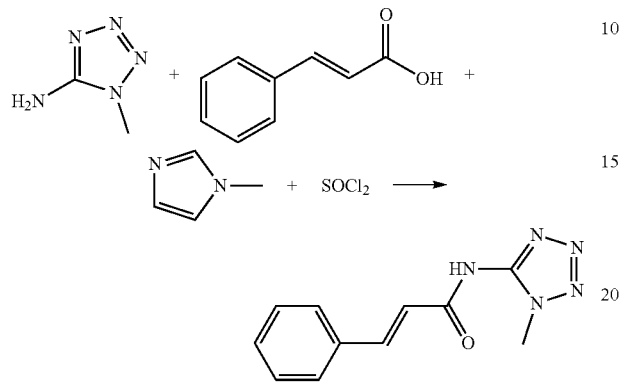

Cinnamic acid (5.0 g, 33.7 mmol), 1-methyl-5-aminotetrazole (3.7 g, 37.1 mmol), 3-methylpyridine (50 ml) and N-methylimidazole (5.5 g, 67.5 mmol) were added to the reaction flask, stirred at room temperature for half an hour, and cooled to be below 10° C. in an ice-water bath; dichlorosuifoxide (6.4 g, 54.0 mmol) was slowly dripped; the mixture was stirred at room temperature for 2. hours, heated to 50° C. to preserve heat and react for 2 hours, and cooled to be below 10° C. in the ice-water bath; cold water was slowly dripped; solid precipitated out and was filtered; a filter cake was washed twice with 50 ml of water and dried to obtain 3.3 g of yellow solid, with a yield of 42%.

(2) Synthesis of 2-chloro-3-{[(tetrahydrofuran-2-yl)methoxy]methyl}-4-methanesulfonyl Benzoyl Chloride

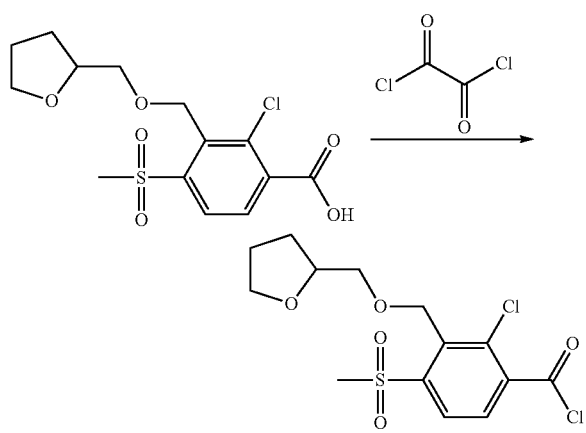

2-chloro-3-{[(tetrahydrofuran-2-yl)methoxy]methyl}-4-methanesulfonyl benzoic, acid (1.3 g, 3.8 mmol), dichloromethane (20 ml) and DMF (1 drop) were added into the reaction flask; oxalyl chloride (2.4 g, 19.0 mmol) was slowly added; the mixture was stirred at room temperature for 2 hours; the solvent was evaporated under reduced pressure; toluene (10 ml) was added to the residue and stirred for 3 minutes; and then the solvent was evaporated under reduced pressure to obtain 1.3 g of yellow solid which was used directly in the next step.

(3) Synthesis of Compound 1-41

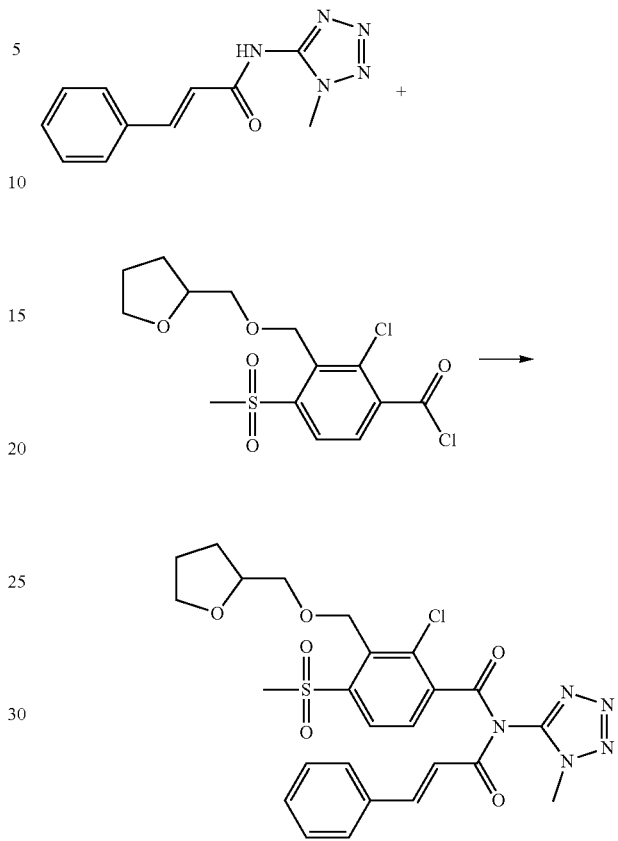

N-(1-methyl-tetrazole-5yl) cinnamamide (0.4 g, 1.9 mmol), dichloromethane (20 ml) and triethylamine (0.4 g, 3.8 mmol) were added to the reaction flask, and the dichloromethane solution of the prepared 2-chloro-3{[(tetrahydrofuran-2-yl)methoxy]methyl}-4-methanesulfon benzoyl chloride was dropwise added (1.3 g of 2-chloro-3-{[(tetrahydrofuran-2-yl)methoxy]methyl}-4-methanesulfonyl benzoyl chloride was dissolved in 15 ml of dichloromethane). The mixture was stirred at room temperature for 40 minutes; the solvent was evaporated under reduced pressure; ethyl acetate (50 ml) was added to the residue; water (50 ml) was used for separation and extraction; the organic phase was washed with saturated salt water (50 ml) and dried with anhydrous magnesium sulfate; the solvent was evaporated under reduced pressure; and the residue was separated by column chromatography to obtain 0.3 g of yellow solid, with a purity of 88% and a yield of 25%.

The initial substances are replaced according to the above recorded method to obtain other compounds shown by the formula IF. Part of the compounds of the formula I can be found in Table 1, Table 2, Table 3 and Table 4, wherein in Table 1 and Table 2, W is selected from $CX_2$ and the stereo configuration in Table 1 is trans; in Table 3 and Table 4, W is selected from N and the stereo configuration in Table 3 is trans.

In the compound of the formula I, W is $CX_2$ and the stereo configuration is trans.

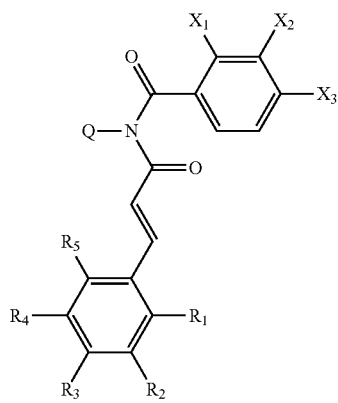

TABLE 1

Structures and Physical Properties of Part of Compounds of Formula I

| Compound | $X_1$ | $X_2$ | $X_3$ | Q | $R_1$ | $R_2$ | $R_3$ | $R_4$ | $R_5$ | Appearance (Melting Point ° C.) |
|---|---|---|---|---|---|---|---|---|---|---|
| 1-1 | $SO_2CH_3$ | H | $CF_3$ | N-methyltetrazol-5-yl | H | H | H | H | H | pale yellow solid (145-146) |
| 1-2 | $SO_2CH_3$ | H | $CF_3$ | N-methyltetrazol-5-yl | Cl | H | Cl | H | H | |
| 1-3 | $SO_2CH_3$ | H | $CF_3$ | N-methyltetrazol-5-yl | H | H | $OCH_3$ | H | H | |
| 1-4 | $SO_2CH_3$ | H | $CF_3$ | N-methyltetrazol-5-yl | H | H | $NO_2$ | H | H | |
| 1-5 | $SO_2CH_3$ | H | $CF_3$ | N-methyltetrazol-5-yl | H | H | $CF_3$ | H | H | |
| 1-6 | $SO_2CH_3$ | H | $CF_3$ | N-methyltetrazol-5-yl | H | $OCF_3$ | H | H | H | |
| 1-7 | $SO_2CH_3$ | H | $CF_3$ | N-methyltetrazol-5-yl | H | H | phenyl | H | H | |

TABLE 1-continued

Structures and Physical Properties of Part of Compounds of Formula I

| Compound | X₁ | X₂ | X₃ | Q | R₁ | R₂ | R₃ | R₄ | R₅ | Appearance (Melting Point ° C.) |
|---|---|---|---|---|---|---|---|---|---|---|
| 1-8 | SO₂CH₃ | H | CF₃ | tetrazole | H | | 1,3-dioxolan-2-yl | H | H | yellow solid (121-123) |
| 1-9 | SO₂CH₃ | H | CF₃ | tetrazole | H | | 1,3-dioxan-2-yl | H | H | |
| 1-10 | SO₂CH₃ | H | CF₃ | tetrazole | H | | cyclohexa-1,3-dien-1-yl | H | H | |
| 1-11 | SO₂CH₃ | H | CF₃ | tetrazole | H | phenyl | H | H | H | |
| 1-12 | NO₂ | H | SO₂CH₃ | tetrazole | H | H | H | H | H | pale yellow solid (189-191) |
| 1-13 | NO₂ | H | SO₂CH₃ | tetrazole | H | | 1,3-dioxolan-2-yl | H | H | yellow solid (185-187) |
| 1-14 | NO₂ | H | Cl | tetrazole | H | H | H | H | H | while solid (157-159) |
| 1-15 | Cl | H | Cl | tetrazole | H | H | H | H | H | yellow solid (148-150) |
| 1-16 | Cl | H | Cl | tetrazole | H | | 1,3-dioxolan-2-yl | H | H | yellow solid (160-162) |
| 1-17 | Cl | H | SO₂CH₃ | tetrazole | H | H | H | H | H | white solid (190-192) |

TABLE 1-continued

Structures and Physical Properties of Part of Compounds of Formula I

| Compound | $X_1$ | $X_2$ | $X_3$ | Q | $R_1$ | $R_2$ | $R_3$ | $R_4$ | $R_5$ | Appearance (Melting Point ° C.) |
|---|---|---|---|---|---|---|---|---|---|---|
| 1-18 | Cl | H | $SO_2CH_3$ | 1-methyltetrazol-5-yl | H | | -OCH₂O- (methylenedioxy) | H | H | pale yellow solid (195-197) |
| 1-19 | Cl | $CH_3$ | $SO_2CH_3$ | 1-methyltetrazol-5-yl | H | H | H | H | H | white solid (185-186) |
| 1-20 | Cl | $CH_3$ | $SO_2CH_3$ | 1-methyltetrazol-5-yl | H | | -OCH₂O- (methylenedioxy) | H | H | pale yellow solid (192-194) |
| 1-21 | Cl | $CH_3$ | $SO_2CH_3$ | 1-methyltetrazol-5-yl | H | H | OCH3 | H | H | pale yellow solid (200-202) |
| 1-22 | Cl | $CH_3$ | $SO_2CH_3$ | 1-methyltetrazol-5-yl | H | H | phenyl | H | H | pale yellow solid (175-177) |
| 1-23 | Cl | $CH_2Br$ | $SO_2CH_3$ | 1-methyltetrazol-5-yl | H | H | H | H | H | |
| 1-24 | Cl | $CH_2OCH_3$ | $SO_2CH_3$ | 1-methyltetrazol-5-yl | H | H | H | H | H | pale yellow solid (180-182) |
| 1-25 | Cl | $CH_2OCH_3$ | $SO_2CH_3$ | 1-methyltetrazol-5-yl | Cl | H | Cl | H | H | |
| 1-26 | Cl | $CH_2OCH_3$ | $SO_2CH_3$ | 1-methyltetrazol-5-yl | H | H | $OCH_3$ | H | H | yellow solid (160-162) |
| 1-27 | Cl | $CH_2OCH_3$ | $SO_2CH_3$ | 1-methyltetrazol-5-yl | H | H | $NO_2$ | H | H | |

TABLE 1-continued

Structures and Physical Properties of Part of Compounds of Formula I

| Compound | $X_1$ | $X_2$ | $X_3$ | Q | $R_1$ | $R_2$ | $R_3$ | $R_4$ | $R_5$ | Appearance (Melting Point ° C.) |
|---|---|---|---|---|---|---|---|---|---|---|
| 1-28 | Cl | CH$_2$OCH$_3$ | SO$_2$CH$_3$ | 1-methyltetrazol-5-yl | H | H | CF$_3$ | H | H | white solid (164-165) |
| 1-29 | Cl | CH$_2$OCH$_3$ | SO$_2$CH$_3$ | 1-methyltetrazol-5-yl | H | OCF$_3$ | H | H | H | |
| 1-30 | Cl | CH$_2$OCH$_3$ | SO$_2$CH$_3$ | 1-methyltetrazol-5-yl | H | H | phenyl | H | H | pale yellow solid (120-123) |
| 1-31 | Cl | CH$_2$OCH$_3$ | SO$_2$CH$_3$ | 1-methyltetrazol-5-yl | H | –O–CH$_2$–O– (R$_2$+R$_3$, 1,3-dioxole) | | H | H | pale yellow solid (115-117) |
| 1-32 | Cl | CH$_2$OCH$_3$ | SO$_2$CH$_3$ | 1-methyltetrazol-5-yl | H | –O–CH$_2$CH$_2$–O– (R$_2$+R$_3$, 1,3-dioxolane) | | H | H | |
| 1-33 | Cl | CH$_2$OCH$_3$ | SO$_2$CH$_3$ | 1-methyltetrazol-5-yl | H | –CH=CH–CH=CH– (R$_2$+R$_3$, fused benzo) | | H | H | yellow solid (120-122) |
| 1-34 | Cl | CH$_2$OCH$_3$ | SO$_2$CH$_3$ | 1-methyltetrazol-5-yl | –CH=CH–CH=CH– (R$_1$+R$_2$, fused benzo) | | H | H | H | |
| 1-35 | Cl | CH$_2$OCH$_2$CH$_3$ | SO$_2$CH$_3$ | 1-methyltetrazol-5-yl | H | H | H | H | H | |
| 1-36 | Cl | CH$_2$OCH$_2$CH=CH$_2$ | SO$_2$CH$_3$ | 1-methyltetrazol-5-yl | H | H | H | H | H | |
| 1-37 | Cl | CH$_2$OCH$_2$C≡CH | SO$_2$CH$_3$ | 1-methyltetrazol-5-yl | H | H | H | H | H | |

TABLE 1-continued

Structures and Physical Properties of Part of Compounds of Formula I

| Compound | X₁ | X₂ | X₃ | Q | R₁ | R₂ | R₃ | R₄ | R₅ | Appearance (Melting Point ° C.) |
|---|---|---|---|---|---|---|---|---|---|---|
| 1-38 | Cl | –CH₂–O–CH(CH₃)CH₂CH₃ | SO₂CH₃ | 1-methyltetrazol-5-yl | H | H | H | H | H | |
| 1-39 | Cl | –CH₂–N(CH₃)₂ | SO₂CH₃ | 1-methyltetrazol-5-yl | H | H | H | H | H | |
| 1-40 | Cl | –CH₂–O–CH₂CF₃ | SO₂CH₃ | 1-methyltetrazol-5-yl | H | H | H | H | H | |
| 1-41 | Cl | –CH₂–O–CH₂-(tetrahydrofuran-2-yl) | SO₂CH₃ | 1-methyltetrazol-5-yl | H | H | H | H | H | yellow solid (98-100) |
| 1-42 | Cl | –CH₂–O–CH₂-(tetrahydrofuran-2-yl) | SO₂CH₃ | 1-methyltetrazol-5-yl | Cl | H | Cl | H | H | |
| 1-43 | Cl | –CH₂–O–CH₂-(tetrahydrofuran-2-yl) | SO₂CH₃ | 1-methyltetrazol-5-yl | H | H | OCH₃ | H | H | |
| 1-44 | Cl | –CH₂–O–CH₂-(tetrahydrofuran-2-yl) | SO₂CH₃ | 1-methyltetrazol-5-yl | H | H | NO₂ | H | H | |
| 1-45 | Cl | –CH₂–O–CH₂-(tetrahydrofuran-2-yl) | SO₂CH₃ | 1-methyltetrazol-5-yl | H | H | CF₃ | H | H | |
| 1-46 | Cl | –CH₂–O–CH₂-(tetrahydrofuran-2-yl) | SO₂CH₃ | 1-methyltetrazol-5-yl | H | OCF₃ | H | H | H | |
| 1-47 | Cl | –CH₂–O–CH₂-(tetrahydrofuran-2-yl) | SO₂CH₃ | 1-methyltetrazol-5-yl | H | H | phenyl | H | H | |

TABLE 1-continued

Structures and Physical Properties of Part of Compounds of Formula I

| Compound | X₁ | X₂ | X₃ | Q | R₁ | R₂ | R₃ | R₄ | R₅ | Appearance (Melting Point ° C.) |
|---|---|---|---|---|---|---|---|---|---|---|
| 1-48 | Cl | ~CH₂-O-CH₂-(tetrahydrofuran-2-yl) | SO₂CH₃ | 1-methyl-tetrazol-5-yl | H | | 1,3-dioxolan-2-yl | H | H | |
| 1-49 | Cl | ~CH₂-O-CH₂-(tetrahydrofuran-2-yl) | SO₂CH₃ | 1-methyl-tetrazol-5-yl | H | 1,3-dioxan-2-yl | | H | H | |
| 1-50 | Cl | ~CH₂-O-CH₂-(tetrahydrofuran-2-yl) | SO₂CH₃ | 1-methyl-tetrazol-5-yl | H | cyclohexa-1,3-dien-yl | | H | H | |
| 1-51 | Cl | ~CH₂-O-CH₂-(tetrahydrofuran-2-yl) | SO₂CH₃ | 1-methyl-tetrazol-5-yl | phenyl | | H | H | H | |
| 1-52 | Cl | ~CH₂-O-CH(1,3-dioxolan-2-yl) | SO₂CH₃ | 1-methyl-tetrazol-5-yl | H | H | H | H | H | |
| 1-53 | Cl | ~CH₂-O-CH₂CH₂-O-CH₃ | SO₂CH₃ | 1-methyl-tetrazol-5-yl | H | H | H | H | H | pale yellow solid (85-87) |
| 1-54 | Cl | cyclohexyl | SO₂CH₃ | 1-methyl-tetrazol-5-yl | H | H | H | H | H | |
| 1-55 | Cl | cyclohexylmethyl | SO₂CH₃ | 1-methyl-tetrazol-5-yl | H | H | H | H | H | |
| 1-56 | Cl | ~CH(OCH₃) | SO₂CH₃ | 1-methyl-tetrazol-5-yl | H | H | H | H | H | white oil |
| 1-57 | Cl | ~CH(OCH₂CH₃) | SO₂CH₃ | 1-methyl-tetrazol-5-yl | H | H | H | H | H | white solid (200-201) |

TABLE 1-continued

Structures and Physical Properties of Part of Compounds of Formula I

| Compound | $X_1$ | $X_2$ | $X_3$ | Q | $R_1$ | $R_2$ | $R_3$ | $R_4$ | $R_5$ | Appearance (Melting Point ° C.) |
|---|---|---|---|---|---|---|---|---|---|---|
| 1-58 | Cl | -S-CH₃ | $SO_2CH_3$ | tetrazole | H | H | H | H | H | |
| 1-59 | Cl | -S-CH₂CH₃ | $SO_2CH_3$ | tetrazole | H | H | H | H | H | |
| 1-60 | Cl | -N(CH₃)₂ | $SO_2CH_3$ | tetrazole | H | H | H | H | H | |
| 1-61 | Cl | $SO_2CH_3$ | $SO_2CH_3$ | tetrazole | H | H | H | H | H | |
| 1-62 | Cl | -S(O)CH₃ | $SO_2CH_3$ | tetrazole | H | H | H | H | H | |
| 1-63 | Cl | -CH₂-S-CH₃ | $SO_2CH_3$ | tetrazole | H | H | H | H | H | |
| 1-64 | Cl | -SO₂CH₃ | $SO_2CH_3$ | tetrazole | H | H | H | H | H | |
| 1-65 | Cl | -CH₂-N(CH₃)₂ | $SO_2CH_3$ | tetrazole | H | H | H | H | H | |
| 1-66 | Cl | -CH₂-SO₂CH₃ | $SO_2CH_3$ | tetrazole | H | H | H | H | H | |
| 1-67 | Cl | -CH₂-S(O)CH₃ | $SO_2CH_3$ | tetrazole | H | H | H | H | H | |
| 1-68 | Cl | -CH₂-C(O)CH₃ | $SO_2CH_3$ | tetrazole | H | H | H | H | H | |

TABLE 1-continued

Structures and Physical Properties of Part of Compounds of Formula I

| Compound | $X_1$ | $X_2$ | $X_3$ | Q | $R_1$ | $R_2$ | $R_3$ | $R_4$ | $R_5$ | Appearance (Melting Point ° C.) |
|---|---|---|---|---|---|---|---|---|---|---|
| 1-69 | Cl | —C(O)OCH₃ | SO₂CH₃ | tetrazolyl | H | H | H | H | H | |
| 1-70 | Cl | —OC(O)OCH₃ | SO₂CH₃ | tetrazolyl | H | H | H | H | H | |
| 1-71 | Cl | —N(CH₃)C(O)OCH₃ | SO₂CH₃ | tetrazolyl | H | H | H | H | H | |
| 1-72 | Cl | —C(O)N(CH₃)₂ | SO₂CH₃ | tetrazolyl | H | H | H | H | H | |
| 1-73 | Cl | —N(CH₃)C(O)N(CH₃)₂ | SO₂CH₃ | tetrazolyl | H | H | H | H | H | |
| 1-74 | Cl | —OC(O)N(CH₃)₂ | SO₂CH₃ | tetrazolyl | H | H | H | H | H | |
| 1-75 | Cl | —N(CH₃)S(O)₂CH₃ | SO₂CH₃ | tetrazolyl | H | H | H | H | H | |
| 1-76 | Cl | —N(CH₃)C(O)CH₃ | SO₂CH₃ | tetrazolyl | H | H | H | H | H | |
| 1-77 | Cl | —OS(O)₂CH₃ | SO₂CH₃ | tetrazolyl | H | H | H | H | H | |
| 1-78 | Cl | —CH=N-OCH₃ | SO₂CH₃ | tetrazolyl | H | H | H | H | H | |

TABLE 1-continued
Structures and Physical Properties of Part of Compounds of Formula I
| Compound | X₁ | X₂ | X₃ | Q | R₁ | R₂ | R₃ | R₄ | R₅ | Appearance (Melting Point ° C.) |
|---|---|---|---|---|---|---|---|---|---|---|
| 1-79 | Cl | 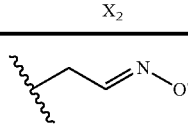 | SO₂CH₃ | 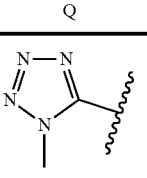 | H | H | H | H | H | |
| 1-80 | Cl | 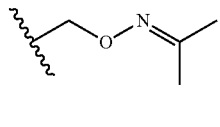 [SMILES: *CON=C(C)C] | SO₂CH₃ | 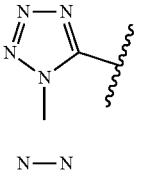 | H | H | H | H | H | |
| 1-81 | Cl | 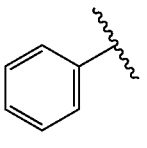 [SMILES: *c1ccccc1] | SO₂CH₃ | 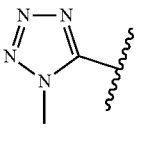 | H | H | H | H | H | |
| 1-82 | Cl | CN | SO₂CH₃ | 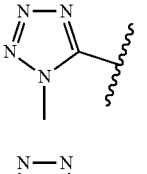 | H | H | H | H | H | |
| 1-83 | Cl | NO₂ | SO₂CH₃ | 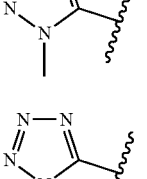 | H | H | H | H | H | |
| 1-84 | Cl | 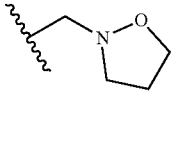 [SMILES: *CN1CCCO1] | SO₂CH₃ | 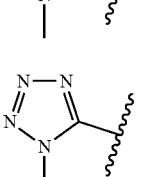 | H | H | H | H | H | |
| 1-85 | Cl | 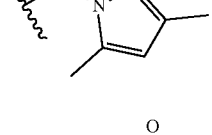 | SO₂CH₃ | 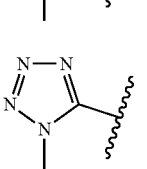 | H | H | H | H | H | |
| 1-86 | Cl | 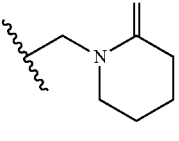 | SO₂CH₃ | 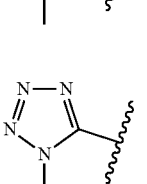 | H | H | H | H | H | |
| 1-87 | Cl | 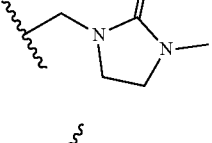 | SO₂CH₃ | 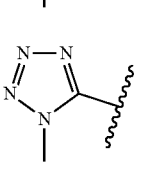 | H | H | H | H | H | |
| 1-88 | Cl | 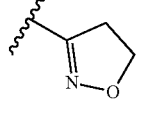 | SO₂CH₃ | 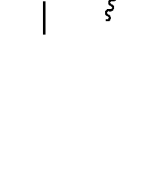 | H | H | H | H | H | |

TABLE 1-continued

Structures and Physical Properties of Part of Compounds of Formula I

| Compound | X₁ | X₂ | X₃ | Q | R₁ | R₂ | R₃ | R₄ | R₅ | Appearance (Melting Point ° C.) |
|---|---|---|---|---|---|---|---|---|---|---|
| 1-89 | Cl | 3,5-dimethylpyrazol-1-yl | SO₂CH₃ | N-methyltetrazol-5-yl | H | H | H | H | H | |
| 1-90 | Cl | Cl | SO₂CH₃ | N-methyltetrazol-5-yl | H | H | H | H | H | yellow solid (198-200) |
| 1-91 | CH₃ | CH₃ | SO₂CH₃ | N-methyltetrazol-5-yl | H | H | H | H | H | while solid (202-204) |
| 1-92 | CH₃ | CH₂Br | SO₂CH₃ | N-methyltetrazol-5-yl | H | H | H | H | H | |
| 1-93 | CH₃ | F | SO₂CH₃ | N-methyltetrazol-5-yl | H | H | H | H | H | |
| 1-94 | CH₃ | Br | SO₂CH₃ | N-methyltetrazol-5-yl | H | H | H | H | H | |
| 1-95 | CH₃ | -OCH₃ | SO₂CH₃ | N-methyltetrazol-5-yl | H | H | H | H | H | white solid (206-208) |
| 1-96 | CH₃ | -OCH₂CH₃ | SO₂CH₃ | N-methyltetrazol-5-yl | H | H | H | H | H | off-white solid (205-207) |
| 1-97 | CH₃ | -OCH₂CH₂OCH₃ | SO₂CH₃ | N-methyltetrazol-5-yl | H | H | H | H | H | white solid (171-173) |
| 1-98 | CH₃ | -CH₂CH₂OCH₃ | SO₂CH₃ | N-methyltetrazol-5-yl | H | H | H | H | H | white solid (202-204) |
| 1-99 | CH₃ | isoxazolidin-2-ylmethyl | SO₂CH₃ | N-methyltetrazol-5-yl | H | H | H | H | H | |

TABLE 1-continued
Structures and Physical Properties of Part of Compounds of Formula I
| Compound | $X_1$ | $X_2$ | $X_3$ | Q | $R_1$ | $R_2$ | $R_3$ | $R_4$ | $R_5$ | Appearance (Melting Point ° C.) |
|---|---|---|---|---|---|---|---|---|---|---|
| 1-100 | $CH_3$ | 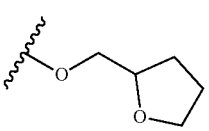 [SMILES: *OCC1CCCO1] | $SO_2CH_3$ | 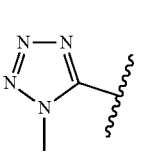 [SMILES: *c1nnnn1C] | H | H | H | H | H | white solid (185-187) |
| 1-101 | $CH_3$ | 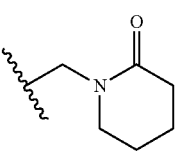 [SMILES: *CN1CCCCC1=O] | $SO_2CH_3$ | 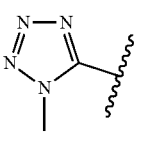 | H | H | H | H | H |  |
| 1-102 | $CH_3$ | 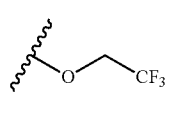 | $SO_2CH_3$ | 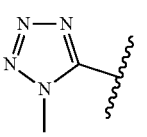 | H | H | H | H | H | yellow solid (216-218) |
| 1-103 | $CH_3$ | 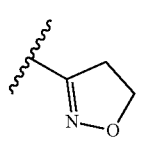 [SMILES: *C1=NOCC1] | $SO_2CH_3$ | 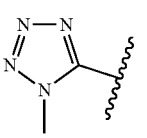 | H | H | H | H | H |  |
| 1-104 | CN | 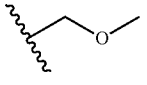 [SMILES: *COC] | $SO_2CH_3$ | 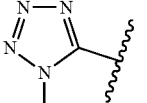 | H | H | H | H | H |  |
| 1-105 | $CF_3$ | 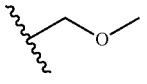 [SMILES: *COC] | $SO_2CH_3$ | 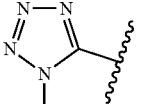 | H | H | H | H | H |  |
| 1-106 | 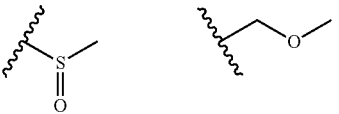 | 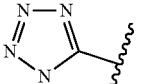 | $SO_2CH_3$ |  | H | H | H | H | H |  |
| 1-107 | 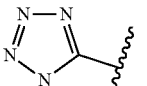 | 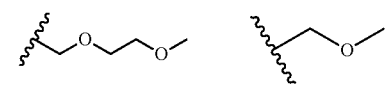 | $SO_2CH_3$ | 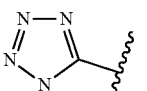 | H | H | H | H | H |  |
| 1-108 | 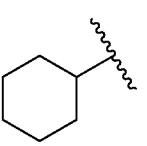 [SMILES: *C1CCCCC1] | 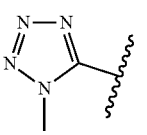 | $SO_2CH_3$ |  | H | H | H | H | H |  |
| 1-109 |  |  | $SO_2CH_3$ |  | H | H | H | H | H |  |

TABLE 1-continued

Structures and Physical Properties of Part of Compounds of Formula I

| Compound | $X_1$ | $X_2$ | $X_3$ | Q | $R_1$ | $R_2$ | $R_3$ | $R_4$ | $R_5$ | Appearance (Melting Point °C.) |
|---|---|---|---|---|---|---|---|---|---|---|
| 1-110 | cyclohexylmethyl | CH₂CH₂OCH₃ | SO₂CH₃ | N-methyltetrazolyl | H | H | H | H | H | |
| 1-111 | allyl | CH₂CH₂OCH₃ | SO₂CH₃ | N-methyltetrazolyl | H | H | H | H | H | |
| 1-112 | propargyl | CH₂CH₂OCH₃ | SO₂CH₃ | N-methyltetrazolyl | H | H | H | H | H | |
| 1-113 | SO₂CH=CH₂ | CH₂CH₂OCH₃ | SO₂CH₃ | N-methyltetrazolyl | H | H | H | H | H | |
| 1-114 | SO₂C≡CH | CH₂CH₂OCH₃ | SO₂CH₃ | N-methyltetrazolyl | H | H | H | H | H | |
| 1-115 | benzyl | CH₂CH₂OCH₃ | SO₂CH₃ | N-methyltetrazolyl | H | H | H | H | H | |
| 1-116 | SO₂Ph | CH₂CH₂OCH₃ | SO₂CH₃ | N-methyltetrazolyl | H | H | H | H | H | |
| 1-117 | 4,5-dihydroisoxazol-3-yl | CH₂CH₂OCH₃ | SO₂CH₃ | N-methyltetrazolyl | H | H | H | H | H | |
| 1-118 | 3,5-dimethylpyrazol-1-yl | CH₂CH₂OCH₃ | SO₂CH₃ | N-methyltetrazolyl | H | H | H | H | H | |
| 1-119 | isoxazolidin-2-ylmethyl | CH₂CH₂OCH₃ | SO₂CH₃ | N-methyltetrazolyl | H | H | H | H | H | |
| 1-120 | (3,5-dimethylpyrazol-1-yl)methyl | CH₂CH₂OCH₃ | SO₂CH₃ | N-methyltetrazolyl | H | H | H | H | H | |

TABLE 1-continued

Structures and Physical Properties of Part of Compounds of Formula I

| Compound | X₁ | X₂ | X₃ | Q | R₁ | R₂ | R₃ | R₄ | R₅ | Appearance (Melting Point ° C.) |
|---|---|---|---|---|---|---|---|---|---|---|
| 1-121 | SO₂CH₃ | H | CF₃ | 5-methyl-1,3,4-oxadiazol-2-yl | H | H | H | H | H | |
| 1-122 | NO₂ | H | SO₂CH₃ | 5-methyl-1,3,4-oxadiazol-2-yl | H | H | H | H | H | |
| 1-123 | Cl | H | Cl | 5-methyl-1,3,4-oxadiazol-2-yl | H | H | H | H | H | |
| 1-124 | Cl | H | SO₂CH₃ | 5-methyl-1,3,4-oxadiazol-2-yl | H | H | H | H | H | |
| 1-125 | Cl | CH | SO₂CH₃ | 5-methyl-1,3,4-oxadiazol-2-yl | H | H | H | H | H | |
| 1-126 | Cl | -CH₂-O-CH₃ | SO₂CH₃ | 5-methyl-1,3,4-oxadiazol-2-yl | H | H | H | H | H | |
| 1-127 | Cl | -CH₂-O-CH₂CH₃ | SO₂CH₃ | 5-methyl-1,3,4-oxadiazol-2-yl | H | H | H | H | H | |
| 1-128 | Cl | -CH₂-O-CH₂CH=CH₂ | SO₂CH₃ | 5-methyl-1,3,4-oxadiazol-2-yl | H | H | H | H | H | |
| 1-129 | Cl | -CH₂-O-CH₂C≡CH | SO₂CH₃ | 5-methyl-1,3,4-oxadiazol-2-yl | H | H | H | H | H | |
| 1-130 | Cl | -CH₂-O-CH(CH₃)₂ | SO₂CH₃ | 5-methyl-1,3,4-oxadiazol-2-yl | H | H | H | H | H | |
| 1-131 | Cl | -CH₂-N(CH₃)₂ | SO₂CH₃ | 5-methyl-1,3,4-oxadiazol-2-yl | H | H | H | H | H | |
| 1-132 | Cl | -CH₂-O-CH₂CH₃ | SO₂CH₃ | 5-methyl-1,3,4-oxadiazol-2-yl | H | H | H | H | H | |

TABLE 1-continued

Structures and Physical Properties of Part of Compounds of Formula I

| Compound | $X_1$ | $X_2$ | $X_3$ | Q | $R_1$ | $R_2$ | $R_3$ | $R_4$ | $R_5$ | Appearance (Melting Point ° C.) |
|---|---|---|---|---|---|---|---|---|---|---|
| 1-133 | Cl | ⁓CH₂SCH₃ | SO₂CH₃ | 5-methyl-1,3,4-oxadiazol-2-yl | H | H | H | H | H | |
| 1-134 | Cl | ⁓CH₂S(O)₂CH₃ | SO₂CH₃ | 5-methyl-1,3,4-oxadiazol-2-yl | H | H | H | H | H | |
| 1-135 | Cl | ⁓CH₂OCH₂CF₃ | SO₂CH₃ | 5-methyl-1,3,4-oxadiazol-2-yl | H | H | H | H | H | |
| 1-136 | Cl | ⁓CH₂O-(tetrahydrofuran-2-yl) | SO₂CH₃ | 5-methyl-1,3,4-oxadiazol-2-yl | H | H | H | H | H | |
| 1-137 | Cl | ⁓OCH₂CH₂-(1,3-dioxolan-2-yl) | SO₂CH₃ | 5-methyl-1,3,4-oxadiazol-2-yl | H | H | H | H | H | |
| 1-138 | Cl | ⁓CH₂OCH₂CH₂OCH₃ | SO₂CH₃ | 5-methyl-1,3,4-oxadiazol-2-yl | H | H | H | H | H | |
| 1-139 | Cl | ⁓CH₂-(isoxazolidin-2-yl) | SO₂CH₃ | 5-methyl-1,3,4-oxadiazol-2-yl | H | H | H | H | H | |
| 1-140 | Cl | ⁓CH₂-(3,5-dimethyl-1H-pyrazol-1-yl) | SO₂CH₃ | 5-methyl-1,3,4-oxadiazol-2-yl | H | H | H | H | H | |
| 1-141 | Cl | ⁓CH₂-(2-oxopiperidin-1-yl) | SO₂CH₃ | 5-methyl-1,3,4-oxadiazol-2-yl | H | H | H | H | H | |
| 1-142 | Cl | ⁓CH₂-(3-methyl-2-oxoimidazolidin-1-yl) | SO₂CH₃ | 5-methyl-1,3,4-oxadiazol-2-yl | H | H | H | H | H | |
| 1-143 | Cl | Cl | SO₂CH₃ | 5-methyl-1,3,4-oxadiazol-2-yl | H | H | H | H | H | |

TABLE 1-continued
Structures and Physical Properties of Part of Compounds of Formula I
| Compound | X₁ | X₂ | X₃ | Q | R₁ | R₂ | R₃ | R₄ | R₅ | Appearance (Melting Point ° C.) |
|---|---|---|---|---|---|---|---|---|---|---|
| 1-144 | CH₃ | F | SO₂CH₃ | 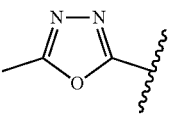 [SMILES: *c1nnc(C)o1] | H | H | H | H | H | |
| 1-145 | CH₃ | Br | SO₂CH₃ | 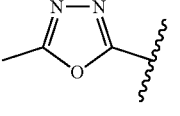 [SMILES: *c1nnc(C)o1] | H | H | H | H | H | |
| 1-146 | CH₃ | 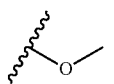 | SO₂CH₃ | 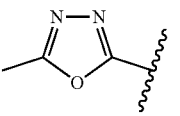 [SMILES: *c1nnc(C)o1] | H | H | H | H | H | — |
| 1-147 | CH₃ | 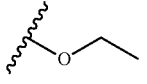 [SMILES: *OCC] | SO₂CH₃ | 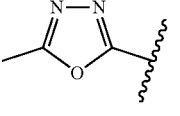 | H | H | H | H | H | |
| 1-148 | CH₃ | 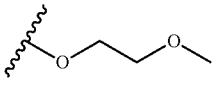 | SO₂CH₃ | 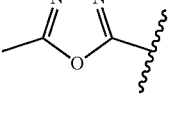 | H | H | H | H | H | |
| 1-149 | CH₃ | 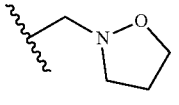 [SMILES: *CN1CCCO1] | SO₂CH₃ | 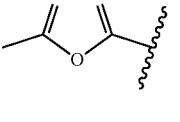 | H | H | H | H | H | |
| 1-150 | CH₃ | 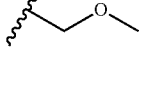 | SO₂CH₃ | 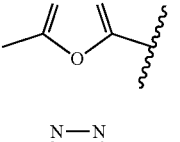 | H | H | H | H | H | |
| 1-151 | CH₃ | 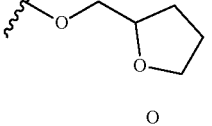 | SO₂CH₃ | 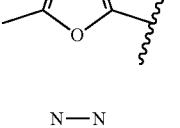 | H | H | H | H | H | |
| 1-152 | CH₃ | 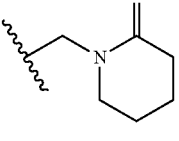 | SO₂CH₃ | 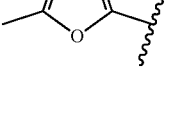 | H | H | H | H | H | |
| 1-153 | CH₃ | 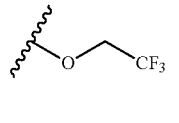 | SO₂CH₃ | 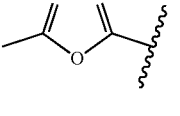 | H | H | H | H | H | |
| 1-154 | SO₂CH₃ | H | CF₃ | 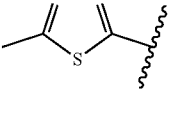 | H | H | H | H | H | yellow solid (180-182) |

TABLE 1-continued

Structures and Physical Properties of Part of Compounds of Formula I

| Compound | X₁ | X₂ | X₃ | Q | R₁ | R₂ | R₃ | R₄ | R₅ | Appearance (Melting Point ° C.) |
|---|---|---|---|---|---|---|---|---|---|---|
| 1-155 | NO₂ | H | SO₂CH₃ | 5-methyl-1,3,4-thiadiazol-2-yl | H | H | H | H | H | |
| 1-156 | Cl | H | Cl | 5-methyl-1,3,4-thiadiazol-2-yl | H | H | H | H | H | |
| 1-157 | Cl | H | SO₂CH₃ | 5-methyl-1,3,4-thiadiazol-2-yl | H | H | H | H | H | |
| 1-158 | Cl | CH₃ | SO₂CH₃ | 5-methyl-1,3,4-thiadiazol-2-yl | H | H | H | H | H | |
| 1-159 | Cl | CH₂OCH₃ | SO₂CH₃ | 5-methyl-1,3,4-thiadiazol-2-yl | H | H | H | H | H | |
| 1-160 | Cl | CH₂OCH₂CH₃ | SO₂CH₃ | 5-methyl-1,3,4-thiadiazol-2-yl | H | H | H | H | H | |
| 1-161 | Cl | CH₂OCH₂CH=CH₂ | SO₂CH₃ | 5-methyl-1,3,4-thiadiazol-2-yl | H | H | H | H | H | |
| 1-162 | Cl | CH₂OCH₂C≡CH | SO₂CH₃ | 5-methyl-1,3,4-thiadiazol-2-yl | H | H | H | H | H | |
| 1-163 | Cl | CH₂OCH(CH₃)₂ | SO₂CH₃ | 5-methyl-1,3,4-thiadiazol-2-yl | H | H | H | H | H | |
| 1-164 | Cl | CH₂N(CH₃)₂ | SO₂CH₃ | 5-methyl-1,3,4-thiadiazol-2-yl | H | H | H | H | H | |
| 1-165 | Cl | OCH₂CH₃ | SO₂CH₃ | 5-methyl-1,3,4-thiadiazol-2-yl | H | H | H | H | H | |
| 1-166 | Cl | CH₂SCH₃ | SO₂CH₃ | 5-methyl-1,3,4-thiadiazol-2-yl | H | H | H | H | H | |

TABLE 1-continued
Structures and Physical Properties of Part of Compounds of Formula I
| Compound | $X_1$ | $X_2$ | $X_3$ | Q | $R_1$ | $R_2$ | $R_3$ | $R_4$ | $R_5$ | Appearance (Melting Point ° C.) |
|---|---|---|---|---|---|---|---|---|---|---|
| 1-167 | Cl | 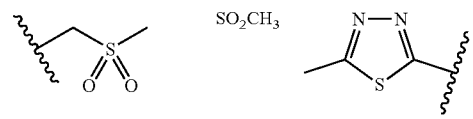 | $SO_2CH_3$ | 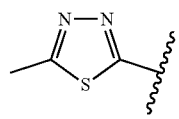 | H | H | H | H | H | |
| 1-168 | Cl | 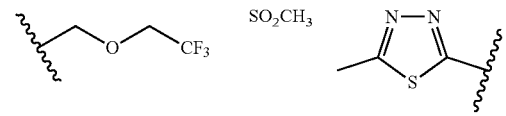 | $SO_2CH_3$ | 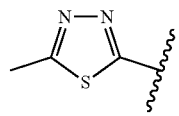 [SMILES: *c1nnc(C)s1] | H | H | H | H | H | |
| 1-169 | Cl | 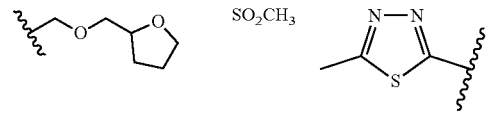 | $SO_2CH_3$ | 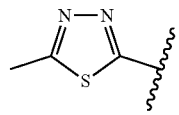 [SMILES: *c1nnc(C)s1] | H | H | H | H | H | |
| 1-170 | Cl | 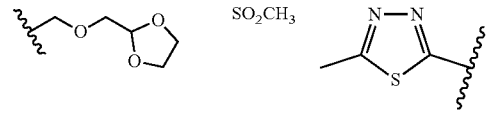 | $SO_2CH_3$ | 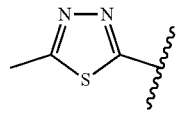 | H | H | H | H | H | |
| 1-171 | Cl | 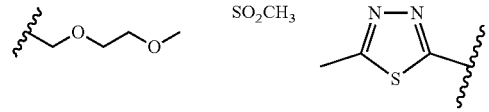 | $SO_2CH_3$ | 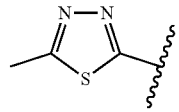 [SMILES: *c1nnc(C)s1] | H | H | H | H | H | |
| 1-172 | Cl | 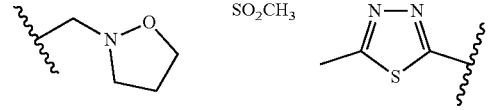 | $SO_2CH_3$ | 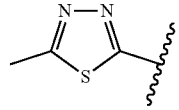 [SMILES: *c1nnc(C)s1] | H | H | H | H | H | |
| 1-173 | Cl | 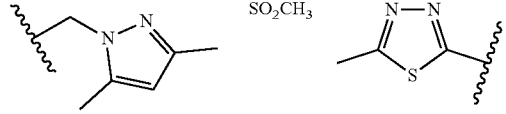 | $SO_2CH_3$ | 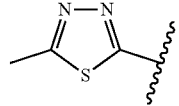 | H | H | H | H | H | |
| 1-174 | Cl | 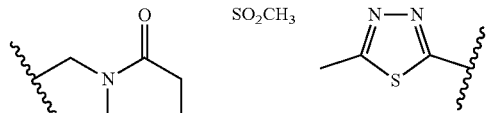 | $SO_2CH_3$ | 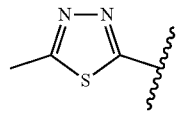 [SMILES: *c1nnc(C)s1] | H | H | H | H | H | |
| 1-175 | Cl |  | $SO_2CH_3$ | 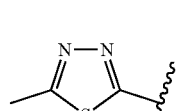 | H | H | H | H | H | |
| 1-176 | Cl | Cl | $SO_2CH_3$ | 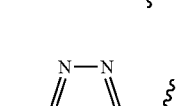 | H | H | H | H | H | |
| 1-177 | $CH_3$ | F | $SO_2CH_3$ | 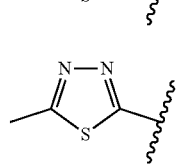 | H | H | H | H | H | |

TABLE 1-continued

Structures and Physical Properties of Part of Compounds of Formula I

| Compound | X₁ | X₂ | X₃ | Q | R₁ | R₂ | R₃ | R₄ | R₅ | Appearance (Melting Point ° C.) |
|---|---|---|---|---|---|---|---|---|---|---|
| 1-178 | CH₃ | Br | SO₂CH₃ | 5-methyl-1,3,4-thiadiazol-2-yl | H | H | H | H | H | |
| 1-179 | CH₃ | OCH₃ | SO₂CH₃ | 5-methyl-1,3,4-thiadiazol-2-yl | H | H | H | H | H | |
| 1-180 | CH₃ | OCH₂CH₃ | SO₂CH₃ | 5-methyl-1,3,4-thiadiazol-2-yl | H | H | H | H | H | |
| 1-181 | CH₃ | OCH₂CH₂OCH₃ | SO₂CH₃ | 5-methyl-1,3,4-thiadiazol-2-yl | H | H | H | H | H | |
| 1-182 | CH₃ | CH₂-(isoxazolidin-2-yl) | SO₂CH₃ | 5-methyl-1,3,4-thiadiazol-2-yl | H | H | H | H | H | |
| 1-183 | CH₃ | CH₂OCH₃ | SO₂CH₃ | 5-methyl-1,3,4-thiadiazol-2-yl | H | H | H | H | H | |
| 1-184 | CH₃ | OCH₂-(tetrahydrofuran-2-yl) | SO₂CH₃ | 5-methyl-1,3,4-thiadiazol-2-yl | H | H | H | H | H | |
| 1-185 | CH₃ | CH₂-(2-oxopiperidin-1-yl) | SO₂CH₃ | 5-methyl-1,3,4-thiadiazol-2-yl | H | H | H | H | H | |
| 1-186 | CH₃ | OCH₂CF₃ | SO₂CH₃ | 5-methyl-1,3,4-thiadiazol-2-yl | H | H | H | H | H | |
| 1-187 | SO₂CH₃ | H | CF₃ | 1-methyl-1H-1,2,3-triazol-4-yl | H | H | H | H | H | off-white solid (100-102) |
| 1-188 | NO₂ | H | SO₂CH₃ | 1-methyl-1H-1,2,3-triazol-4-yl | H | H | H | H | H | |

TABLE 1-continued
Structures and Physical Properties of Part of Compounds of Formula I
| Compound | $X_1$ | $X_2$ | $X_3$ | Q | $R_1$ | $R_2$ | $R_3$ | $R_4$ | $R_5$ | Appearance (Melting Point ° C.) |
|---|---|---|---|---|---|---|---|---|---|---|
| 1-189 | Cl | H | Cl | 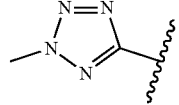 [SMILES: *c1nnn(C)n1] | H | H | H | H | H | |
| 1-190 | Cl | H | $SO_2CH_3$ | 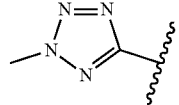 [SMILES: *c1nnn(C)n1] | H | H | H | H | H | |
| 1-191 | Cl | $CH_3$ | $SO_2CH_3$ | 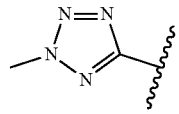 [SMILES: *c1nnn(C)n1] | H | H | H | H | H | |
| 1-192 | Cl | 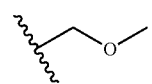 [SMILES: *COC] | $SO_2CH_3$ | 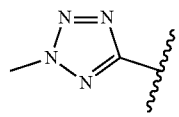 [SMILES: *c1nnn(C)n1] | H | H | H | H | H | |
| 1-193 | Cl | 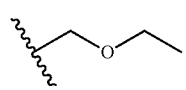 [SMILES: *COCC] | $SO_2CH_3$ | 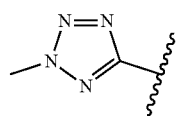 [SMILES: *c1nnn(C)n1] | H | H | H | H | H | |
| 1-194 | Cl | 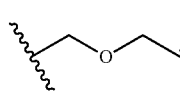 | $SO_2CH_3$ | 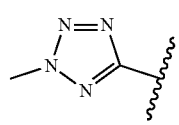 [SMILES: *c1nnn(C)n1] | H | H | H | H | H | |
| 1-195 | Cl | 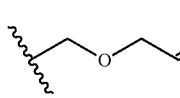 | $SO_2CH_3$ | 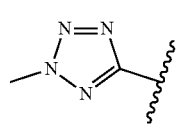 [SMILES: *c1nnn(C)n1] | H | H | H | H | H | |
| 1-196 | Cl | 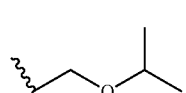 | $SO_2CH_3$ | 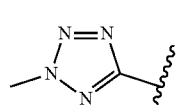 | H | H | H | H | H | |
| 1-197 | Cl | 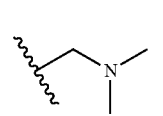 | $SO_2CH_3$ | 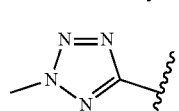 | H | H | H | H | H | |
| 1-198 | Cl |  | $SO_2CH_3$ | 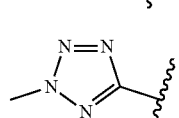 | H | H | H | H | H | |
| 1-199 | Cl | 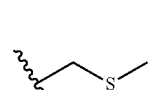 | $SO_2CH_3$ | 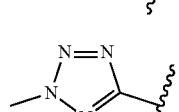 | H | H | H | H | H | |
| 1-200 | Cl | 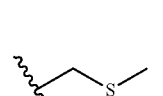 | $SO_2CH_3$ | 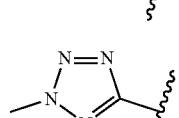 | H | H | H | H | H | |

TABLE 1-continued

Structures and Physical Properties of Part of Compounds of Formula I

| Compound | $X_1$ | $X_2$ | $X_3$ | Q | $R_1$ | $R_2$ | $R_3$ | $R_4$ | $R_5$ | Appearance (Melting Point ° C.) |
|---|---|---|---|---|---|---|---|---|---|---|
| 1-201 | Cl | —CH$_2$—O—CH$_2$CF$_3$ | SO$_2$CH$_3$ | 2-methyl-tetrazol-5-yl | H | H | H | H | H | |
| 1-202 | Cl | —CH$_2$—O—CH$_2$-(tetrahydrofuran-2-yl) | SO$_2$CH$_3$ | 2-methyl-tetrazol-5-yl | H | H | H | H | H | |
| 1-203 | Cl | —CH$_2$—O—CH$_2$-(1,3-dioxolan-2-yl) | SO$_2$CH$_3$ | 2-methyl-tetrazol-5-yl | H | H | H | H | H | |
| 1-204 | Cl | —CH$_2$—O—CH$_2$CH$_2$—O—CH$_3$ | SO$_2$CH$_3$ | 2-methyl-tetrazol-5-yl | H | H | H | H | H | |
| 1-205 | Cl | —CH$_2$-(isoxazolidin-2-yl) | SO$_2$CH$_3$ | 2-methyl-tetrazol-5-yl | H | H | H | H | H | |
| 1-206 | Cl | —CH$_2$-(3,5-dimethylpyrazol-1-yl) | SO$_2$CH$_3$ | 2-methyl-tetrazol-5-yl | H | H | H | H | H | |
| 1-207 | Cl | —CH$_2$-(2-oxopiperidin-1-yl) | SO$_2$CH$_3$ | 2-methyl-tetrazol-5-yl | H | H | H | H | H | |
| 1-208 | Cl | —CH$_2$-(3-methyl-2-oxoimidazolidin-1-yl) | SO$_2$CH$_3$ | 2-methyl-tetrazol-5-yl | H | H | H | H | H | |
| 1-209 | Cl | Cl | SO$_2$CH$_3$ | 2-methyl-tetrazol-5-yl | H | H | H | H | H | |
| 1-210 | CH$_3$ | F | SO$_2$CH$_3$ | 2-methyl-tetrazol-5-yl | H | H | H | H | H | |
| 1-211 | CH$_3$ | Br | SO$_2$CH$_3$ | 2-methyl-tetrazol-5-yl | H | H | H | H | H | |

TABLE 1-continued

Structures and Physical Properties of Part of Compounds of Formula I

| Compound | X₁ | X₂ | X₃ | Q | R₁ | R₂ | R₃ | R₄ | R₅ | Appearance (Melting Point °C.) |
|---|---|---|---|---|---|---|---|---|---|---|
| 1-212 | CH₃ | –OCH₃ | SO₂CH₃ | 2-methyltetrazol-5-yl | H | H | H | H | H | |
| 1-213 | CH₃ | –OC₂H₅ | SO₂CH₃ | 2-methyltetrazol-5-yl | H | H | H | H | H | |
| 1-214 | CH₃ | –OCH₂CH₂OCH₃ | SO₂CH₃ | 2-methyltetrazol-5-yl | H | H | H | H | H | |
| 1-215 | CH₃ | isoxazolidin-2-ylmethyl | SO₂CH₃ | 2-methyltetrazol-5-yl | H | H | H | H | H | |
| 1-216 | CH₃ | –CH₂OCH₃ | SO₂CH₃ | 2-methyltetrazol-5-yl | H | H | H | H | H | |
| 1-217 | CH₃ | –O-CH₂-(tetrahydrofuran-2-yl) | SO₂CH₃ | 2-methyltetrazol-5-yl | H | H | H | H | H | |
| 1-218 | CH₃ | (2-oxopiperidin-1-yl)methyl | SO₂CH₃ | 2-methyltetrazol-5-yl | H | H | H | H | H | |
| 1-219 | CH₃ | –OCH₂CF₃ | SO₂CH₃ | 2-methyltetrazol-5-yl | H | H | H | H | H | |
| 1-220 | SO₂CH₃ | H | CF₃ | 1-methyl-1,2,4-triazol-5-yl | H | H | H | H | H | |
| 1-221 | NO₂ | H | SO₂CH₃ | 1-methyl-1,2,4-triazol-5-yl | H | H | H | H | H | |
| 1-222 | Cl | H | Cl | 1-methyl-1,2,4-triazol-5-yl | H | H | H | H | H | |

TABLE 1-continued

Structures and Physical Properties of Part of Compounds of Formula I

| Compound | X₁ | X₂ | X₃ | Q | R₁ | R₂ | R₃ | R₄ | R₅ | Appearance (Melting Point ° C.) |
|---|---|---|---|---|---|---|---|---|---|---|
| 1-223 | Cl | H | SO₂CH₃ | 1-methyl-1,2,4-triazol-5-yl | H | H | H | H | H | |
| 1-224 | Cl | CH₃ | SO₂CH₃ | 1-methyl-1,2,4-triazol-5-yl | H | H | H | H | H | |
| 1-225 | Cl | -CH₂OCH₃ | SO₂CH₃ | 1-methyl-1,2,4-triazol-5-yl | H | H | H | H | H | |
| 1-226 | Cl | -CH₂OCH₂CH₃ | SO₂CH₃ | 1-methyl-1,2,4-triazol-5-yl | H | H | H | H | H | |
| 1-227 | Cl | -CH₂OCH₂CH=CH₂ | SO₂CH₃ | 1-methyl-1,2,4-triazol-5-yl | H | H | H | H | H | |
| 1-228 | Cl | -CH₂OCH₂C≡CH | SO₂CH₃ | 1-methyl-1,2,4-triazol-5-yl | H | H | H | H | H | |
| 1-229 | Cl | -CH₂OCH(CH₃)₂ | SO₂CH₃ | 1-methyl-1,2,4-triazol-5-yl | H | H | H | H | H | |
| 1-230 | Cl | -CH₂N(CH₃)₂ | SO₂CH₃ | 1-methyl-1,2,4-triazol-5-yl | H | H | H | H | H | |
| 1-231 | Cl | -OCH₂CH₃ | SO₂CH₃ | 1-methyl-1,2,4-triazol-5-yl | H | H | H | H | H | |
| 1-232 | Cl | -CH₂SCH₃ | SO₂CH₃ | 1-methyl-1,2,4-triazol-5-yl | H | H | H | H | H | |
| 1-233 | Cl | -CH₂S(O)₂CH₃ | SO₂CH₃ | 1-methyl-1,2,4-triazol-5-yl | H | H | H | H | H | |

TABLE 1-continued

Structures and Physical Properties of Part of Compounds of Formula I

| Compound | $X_1$ | $X_2$ | $X_3$ | Q | $R_1$ | $R_2$ | $R_3$ | $R_4$ | $R_5$ | Appearance (Melting Point ° C.) |
|---|---|---|---|---|---|---|---|---|---|---|
| 1-234 | Cl | -CH₂-O-CH₂-CF₃ | SO₂CH₃ | 1-methyl-1,2,4-triazol-5-yl | H | H | H | H | H | |
| 1-235 | Cl | -CH₂-O-CH₂-(tetrahydrofuran-2-yl) | SO₂CH₃ | 1-methyl-1,2,4-triazol-5-yl | H | H | H | H | H | |
| 1-236 | Cl | -CH₂-O-CH₂-CH₂-(1,3-dioxolan-2-yl) | SO₂CH₃ | 1-methyl-1,2,4-triazol-5-yl | H | H | H | H | H | |
| 1-237 | Cl | -CH₂-O-CH₂-CH₂-O-CH₃ | SO₂CH₃ | 1-methyl-1,2,4-triazol-5-yl | H | H | H | H | H | |
| 1-238 | Cl | -CH₂-(isoxazolidin-2-yl) | SO₂CH₃ | 1-methyl-1,2,4-triazol-5-yl | H | H | H | H | H | |
| 1-239 | Cl | -CH₂-(3,5-dimethylpyrazol-1-yl) | SO₂CH₃ | 1-methyl-1,2,4-triazol-5-yl | H | H | H | H | H | |
| 1-240 | Cl | -CH₂-(2-oxopiperidin-1-yl) | SO₂CH₃ | 1-methyl-1,2,4-triazol-5-yl | H | H | H | H | H | |
| 1-241 | Cl | -CH₂-(3-methyl-2-oxoimidazolidin-1-yl) | SO₂CH₃ | 1-methyl-1,2,4-triazol-5-yl | H | H | H | H | H | |
| 1-242 | Cl | Cl | SO₂CH₃ | 1-methyl-1,2,4-triazol-5-yl | H | H | H | H | H | |
| 1-243 | CH₃ | F | SO₂CH₃ | 1-methyl-1,2,4-triazol-5-yl | H | H | H | H | H | |

TABLE 1-continued

Structures and Physical Properties of Part of Compounds of Formula I

| Compound | X₁ | X₂ | X₃ | Q | R₁ | R₂ | R₃ | R₄ | R₅ | Appearance (Melting Point ° C.) |
|---|---|---|---|---|---|---|---|---|---|---|
| 1-244 | CH₃ | Br | SSO₂CH₃ | 1,2,4-triazol-5-yl (N-Me) | H | H | H | H | H | |
| 1-245 | CH₃ | -OCH₃ | SO₂CH₃ | 1,2,4-triazol-5-yl (N-Me) | H | H | H | H | H | |
| 1-246 | CH₃ | -OC₂H₅ | SO₂CH₃ | 1,2,4-triazol-5-yl (N-Me) | H | H | H | H | H | |
| 1-247 | CH₃ | -OCH₂CH₂OCH₃ | SO₂CH₃ | 1,2,4-triazol-5-yl (N-Me) | H | H | H | H | H | |
| 1-248 | CH₃ | -CH₂-isoxazolidinyl | SO₂CH₃ | 1,2,4-triazol-5-yl (N-Me) | H | H | H | H | H | |
| 1-249 | CH₃ | -CH₂CH₂OCH₃ | SO₂CH₃ | 1,2,4-triazol-5-yl (N-Me) | H | H | H | H | H | |
| 1-250 | CH₃ | -OCH₂-(tetrahydrofuran-2-yl) | SO₂CH₃ | 1,2,4-triazol-5-yl (N-Me) | H | H | H | H | H | |
| 1-251 | CH₃ | -CH₂-(2-oxopiperidin-1-yl) | SO₂CH₃ | 1,2,4-triazol-5-yl (N-Me) | H | H | H | H | H | |
| 1-252 | CH₃ | -OCH₂CF₃ | SO₂CH₃ | 1,2,4-triazol-5-yl (N-Me) | H | H | H | H | H | |
| 1-253 | SO₂CH₃ | H | CF₃ | 1,2,3-oxadiazol (N-Me) | H | H | H | H | H | |

TABLE 1-continued
Structures and Physical Properties of Part of Compounds of Formula I
| Compound | X₁ | X₂ | X₃ | Q | R₁ | R₂ | R₃ | R₄ | R₅ | Appearance (Melting Point ° C.) |
|---|---|---|---|---|---|---|---|---|---|---|
| 1-254 | NO₂ | H | SO₂CH₃ | 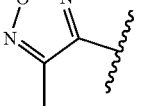 | H | H | H | H | H | |
| 1-255 | Cl | H | Cl | 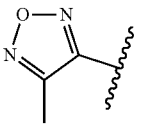 | H | H | H | H | H | |
| 1-256 | Cl | H | SO₂CH₃ | 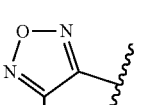 | H | H | H | H | H | |
| 1-257 | Cl | CH₃ | SO₂CH₃ | 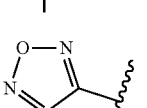 | H | H | H | H | H | |
| 1-258 | Cl | 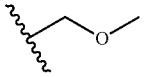 | SO₂CH₃ | 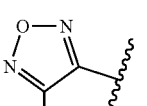 | H | H | H | H | H | |
| 1-259 | Cl | 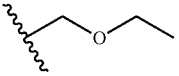 [SMILES: *COCC] | SO₂CH₃ | 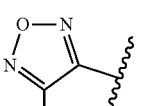 | H | H | H | H | H | |
| 1-260 | Cl | 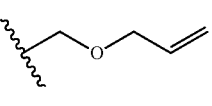 [SMILES: *COCC=C] | SO₂CH₃ | 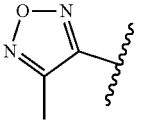 | H | H | H | H | H | |
| 1-261 | Cl | 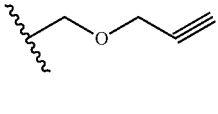 [SMILES: *COCC#C] | SO₂CH₃ | 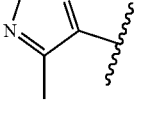 | H | H | H | H | H | |
| 1-262 | Cl | 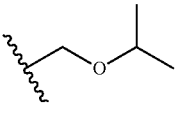 [SMILES: *COC(C)C] | SO₂CH₃ | 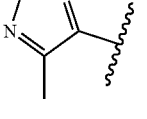 | H | H | H | H | H | |
| 1-263 | Cl | 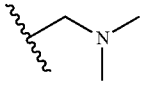 [SMILES: *CN(C)C] | SO₂CH₃ | 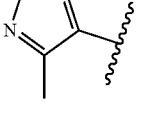 | H | H | H | H | H | |
| 1-264 | Cl | 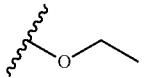 [SMILES: *OCC] | SO₂CH₃ | 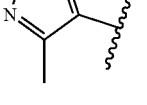 | H | H | H | H | H | |

TABLE 1-continued

Structures and Physical Properties of Part of Compounds of Formula I

| Compound | $X_1$ | $X_2$ | $X_3$ | Q | $R_1$ | $R_2$ | $R_3$ | $R_4$ | $R_5$ | Appearance (Melting Point °C.) |
|---|---|---|---|---|---|---|---|---|---|---|
| 1-265 | Cl | -CH2-S-CH3 | $SO_2CH_3$ | oxadiazole | H | H | H | H | H | |
| 1-266 | Cl | -CH2-S(O)2-CH3 | $SO_2CH_3$ | oxadiazole | H | H | H | H | H | |
| 1-267 | Cl | -CH2-O-CH2-CF3 | $SO_2CH_3$ | oxadiazole | H | H | H | H | H | |
| 1-268 | Cl | -CH2-O-CH2-(tetrahydrofuran) | $SO_2CH_3$ | oxadiazole | H | H | H | H | H | |
| 1-269 | Cl | -CH2-O-CH2-(1,3-dioxolane) | $SO_2CH_3$ | oxadiazole | H | H | H | H | H | |
| 1-270 | Cl | -CH2-O-CH2CH2-O-CH3 | $SO_2CH_3$ | oxadiazole | H | H | H | H | H | |
| 1-271 | Cl | -CH2-(isoxazolidine) | $SO_2CH_3$ | oxadiazole | H | H | H | H | H | |
| 1-272 | Cl | -CH2-(3,5-dimethylpyrazol-1-yl) | $SO_2CH_3$ | oxadiazole | H | H | H | H | H | |
| 1-273 | Cl | -CH2-(2-oxopiperidin-1-yl) | $SO_2CH_3$ | oxadiazole | H | H | H | H | H | |
| 1-274 | Cl | -CH2-(3-methyl-2-oxoimidazolidin-1-yl) | $SO_2CH_3$ | oxadiazole | H | H | H | H | H | |

TABLE 1-continued

Structures and Physical Properties of Part of Compounds of Formula I

| Compound | X₁ | X₂ | X₃ | Q | R₁ | R₂ | R₃ | R₄ | R₅ | Appearance (Melting Point ° C.) |
|---|---|---|---|---|---|---|---|---|---|---|
| 1-275 | Cl | Cl | SO₂CH₃ | 3-methyl-furazan-4-yl | H | H | H | H | H | |
| 1-276 | CH₃ | F | SO₂CH₃ | 3-methyl-furazan-4-yl | H | H | H | H | H | |
| 1-277 | CH₃ | Br | SO₂CH₃ | 3-methyl-furazan-4-yl | H | H | H | H | H | |
| 1-278 | CH₃ | –OCH₃ | SO₂CH₃ | 3-methyl-furazan-4-yl | H | H | | | | |
| 1-279 | CH₃ | –OCH₂CH₃ | SO₂CH₃ | 3-methyl-furazan-4-yl | H | H | H | H | H | |
| 1-280 | CH₃ | –OCH₂CH₂OCH₃ | SO₂CH₃ | 3-methyl-furazan-4-yl | H | H | H | H | H | |
| 1-281 | CH₃ | –CH₂-isoxazolidin-2-yl | SO₂CH₃ | 3-methyl-furazan-4-yl | H | H | H | H | H | |
| 1-282 | CH₃ | –CH₂CH₂OCH₃ | SO₂CH₃ | 3-methyl-furazan-4-yl | H | H | H | H | H | |
| 1-283 | CH₃ | –OCH₂-(tetrahydrofuran-2-yl) | SO₂CH₃ | 3-methyl-furazan-4-yl | H | H | H | H | H | |
| 1-284 | CH₃ | –CH₂-(2-oxopiperidin-1-yl) | SO₂CH₃ | 3-methyl-furazan-4-yl | H | H | H | H | H | |

TABLE 1-continued

Structures and Physical Properties of Part of Compounds of Formula I

| Compound | X₁ | X₂ | X₃ | Q | R₁ | R₂ | R₃ | R₄ | R₅ | Appearance (Melting Point ° C.) |
|---|---|---|---|---|---|---|---|---|---|---|
| 1-285 | CH₃ | -OCH₂CF₃ | SO₂CH₃ | oxadiazole | H | H | H | H | H | |
| 1-286 | Cl | -O-(tetrahydrofuran-2-yl) | SO₂CH₃ | tetrazole (N-CH₃) | H | H | H | H | H | |
| 1-287 | Cl | -O-cyclopentyl | SO₂CH₃ | tetrazole (N-CH₃) | H | H | H | H | H | |
| 1-288 | Cl | N-(2-oxopiperidinyl) | SO₂CH₃ | tetrazole (N-CH₃) | H | H | H | H | H | |
| 1-289 | Cl | SO₂CH₃ | CF₃ | tetrazole (N-CH₃) | H | H | H | H | H | |
| 1-290 | Cl | 3,5-dimethylpyrazol-1-yl | SO₂CH₃ | tetrazole (N-CH₃) | H | H | H | H | H | |
| 1-291 | CH₃ | -O-(tetrahydrofuran-2-yl) | SO₂CH₃ | tetrazole (N-CH₃) | H | H | H | H | H | |
| 1-292 | CH₃ | -O-cyclopentyl | SO₂CH₃ | tetrazole (N-CH₃) | H | H | H | H | H | |
| 1-293 | CH₃ | N-(2-oxopiperidinyl) | SO₂CH₃ | tetrazole (N-CH₃) | H | H | H | H | H | |
| 1-294 | CH₃ | SO₂CH₃ | CF₃ | tetrazole (N-CH₃) | H | H | H | H | H | |

TABLE 1-continued

Structures and Physical Properties of Part of Compounds of Formula I

| Compound | X₁ | X₂ | X₃ | Q | R₁ | R₂ | R₃ | R₄ | R₅ | Appearance (Melting Point ° C.) |
|---|---|---|---|---|---|---|---|---|---|---|
| 1-295 | CH₃ | 1,3-dimethylpyrazol-1-yl | SO₂CH₃ | 1-methyltetrazol-5-yl | H | H | H | H | H | |
| 1-296 | CH₃ | -OCH₂CH₂CH₃ | SO₂CH₃ | 1-methyltetrazol-5-yl | H | H | H | H | H | orange solid (172-174) |
| 1-297 | CH₃ | -OCH(CH₃)₂ | SO₂CH₃ | 1-methyltetrazol-5-yl | H | H | H | H | H | yellow solid (190-192) |
| 1-298 | Cl | -CH₂OCH₃ | SO₂CH₃ | 1-methyltetrazol-5-yl | H | H | CH₃ | H | H | off-white solid (191-193) |
| 1-299 | Cl | -CH₂OCH₃ | SO₂CH₃ | 1-methyltetrazol-5-yl | H | H | F | H | H | off-white solid (188-190) |
| 1-300 | Cl | -CH₂OCH₃ | SO₂CH₃ | 1-methyltetrazol-5-yl | CH₃ | H | H | H | H | off-white solid (150-152) |
| 1-301 | Cl | -CH₂OCH₃ | SO₂CH₃ | 1-methyltetrazol-5-yl | OCH₃ | H | H | H | H | yellow solid (80-82) |
| 1-302 | CH₃ | -OCH₂CH₂OCH₂CH₃ | SO₂CH₃ | 1-methyltetrazol-5-yl | H | H | H | H | H | pale yellow solid (115-117) |
| 1-303 | Cl | -CH₂OCH₃ | SO₂CH₃ | 1-methyltetrazol-5-yl | F | H | H | H | H | of-white solid (157-161) |
| 1-304 | Cl | -CH₂OCH₃ | SO₂CH₃ | 1-methyltetrazol-5-yl | CF₃ | H | H | H | H | off-white solid (178-182) |
| 1-305 | Cl | -CH₂OCH₃ | SO₂CH₃ | 1-methyltetrazol-5-yl | Cl | H | H | H | H | off-white solid (165-169) |

TABLE 1-continued

Structures and Physical Properties of Part of Compounds of Formula I

| Compound | $X_1$ | $X_2$ | $X_3$ | Q | $R_1$ | $R_2$ | $R_3$ | $R_4$ | $R_5$ | Appearance (Melting Point ° C.) |
|---|---|---|---|---|---|---|---|---|---|---|
| 1-306 | Cl | —CH₂CH₂OCH₃ | SO₂CH₃ | tetrazole | Br | H | H | H | H | off-white solid (144-148) |
| 1-307 | Cl | —CH₂CH₂OCH₃ | SO₂CH₃ | tetrazole | H | CH₃ | H | H | H | off-white solid (96-100) |
| 1-308 | Cl | —CH₂CH₂OCH₃ | SO₂CH₃ | tetrazole | H | Br | H | H | H | off-white solid (164-168) |
| 1-309 | Cl | —CH₂CH₂OCH₃ | SO₂CH₃ | tetrazole | H | Cl | H | H | H | off-white solid (186-190) |
| 1-310 | Cl | —CH₂CH₂OCH₃ | SO₂CH₃ | tetrazole | H | CF₃ | H | H | H | off-white solid (179-182) |
| 1-311 | Cl | —CH₂CH₂OCH₃ | SO₂CH₃ | tetrazole | H | F | H | H | H | off-white solid (207-212) |
| 1-312 | CH₃ | —OCH₂CH₂OCH₃ | SO₂CH₃ | tetrazole | H | H | H | H | H | white solid (169-170) |
| 1-313 | CH₃ | —OCH₂CH₂CH₂OCH₃ | SO₂CH₃ | tetrazole | H | H | H | H | H | white solid (176-177) |
| 1-314 | Cl | —OCH₂CH₂OCH₂CH₃ | SO₂CH₃ | tetrazole | H | H | H | H | H | yellow oil |
| 1-315 | Cl | —OCH₂CH₂OCH₃ | SO₂CH₃ | tetrazole | H | H | H | H | H | white solid (210-212) |

TABLE 1-continued

Structures and Physical Properties of Part of Compounds of Formula I

| Compound | X₁ | X₂ | X₃ | Q | R₁ | R₂ | R₃ | R₄ | R₅ | Appearance (Melting Point ° C.) |
|---|---|---|---|---|---|---|---|---|---|---|
| 1-316 | Cl | ~O~O~ | SO₂CH₃ | N-methyl tetrazole | H | H | H | H | H | yellow oil |
| 1-317 | Cl | ~O~O~ | SO₂CH₃ | N-methyl tetrazole | H | H | H | H | H | yellow oil |
| 1-318 | Cl | ~O~ | SO₂CH₃ | N-methyl tetrazole | H | H | H | H | H | pale yellow oil |
| 1-319 | Cl | ~O~cyclopropyl | SO₂CH₃ | N-methyl tetrazole | H | H | H | H | H | pale yellow oil |

In the compound of the formula I, W is $CX_2$.

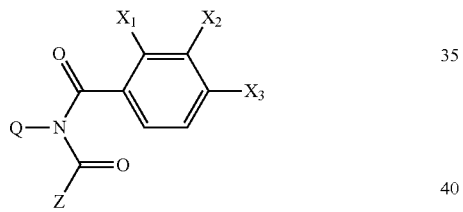

TABLE 2

Structures and Physical Properties of Part of Compounds of Formula I

| Compound | X₁ | X₂ | X₃ | Q | Z | Appearance (Melting Point ° C.) |
|---|---|---|---|---|---|---|
| 2-1 | CH₃ | ~OCH₃ | SO₂CH₃ | N-methyl tetrazole | cyclohexenyl | |
| 2-2 | CH₃ | ~OCH₃ | SO₂CH₃ | N-methyl tetrazole | cyclohexenyl | |
| 2-3 | CH₃ | ~OCH₃ | SO₂CH₃ | N-methyl tetrazole | cyclopentenyl | |

TABLE 2-continued

Structures and Physical Properties of Part of Compounds of Formula I

| Compound | $X_1$ | $X_2$ | $X_3$ | Q | Z | Appearance (Melting Point ° C.) |
|---|---|---|---|---|---|---|
| 2-4 | $CH_3$ | —O—CH₃ | $SO_2CH_3$ | N-methyltetrazol-5-yl | cyclopent-3-enyl | |
| 2-5 | $CH_3$ | —O—CH₃ | $SO_2CH_3$ | N-methyltetrazol-5-yl | 4-(prop-1-en-2-yl)cyclohex-1-enyl | |
| 2-6 | $CH_3$ | cyclopent-2-enyl | $SO_2CH_3$ | N-methyltetrazol-5-yl | cyclohexa-2,5-dien-1-yl | |
| 2-7 | $CH_3$ | —O—Et | $SO_2CH_3$ | N-methyltetrazol-5-yl | cyclohex-1-enyl | orange solid (147-148) |
| 2-8 | $CH_3$ | —O—Et | $SO_2CH_3$ | N-methyltetrazol-5-yl | cyclohexyl | |
| 2-9 | $CH_3$ | —O—Et | $SO_2CH_3$ | N-methyltetrazol-5-yl | cyclopent-1-enyl | white solid (177-178) |
| 2-10 | $CH_3$ | —O—Et | $SO_2CH_3$ | N-methyltetrazol-5-yl | cyclopent-3-enyl | |
| 2-11 | $CH_3$ | —O—Et | $SO_2CH_3$ | N-methyltetrazol-5-yl | 4-(prop-1-en-2-yl)cyclohex-1-enyl | |
| 2-12 | $CH_3$ | —O—Et | $SO_2CH_3$ | N-methyltetrazol-5-yl | cyclohexa-2,5-dien-1-yl | |
| 2-13 | $CH_3$ | —O—CH₂CF₃ | $SO_2CH_3$ | N-methyltetrazol-5-yl | cyclohex-1-enyl | white solid (142-143) |

TABLE 2-continued
Structures and Physical Properties of Part of Compounds of Formula I
| Compound | X₁ | X₂ | X₃ | Q | Z | Appearance (Melting Point ° C.) |
|---|---|---|---|---|---|---|
| 2-14 | CH₃ | 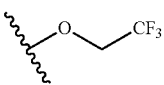 | SO₂CH₃ | 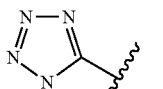 | 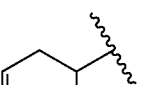 | |
| 2-15 | CH₃ | 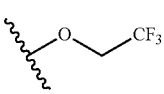 | SO₂CH₃ | 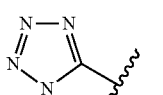 | 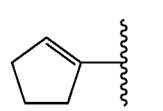 [SMILES: *C1=CCCC1] | pale yellow solid (130-131) |
| 2-16 | CH₃ | 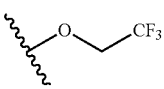 | SO₂CH₃ | 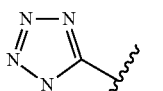 | 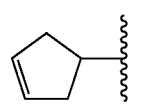 [SMILES: *C1CC=CC1] | |
| 2-17 | CH₃ | 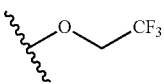 | SO₂CH₃ | 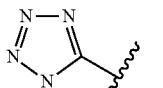 | 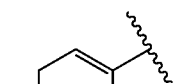 | |
| 2-18 | CH₃ | 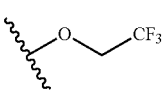 | SO₂CH₃ | 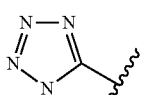 | 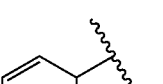 | |
| 2-19 | CH₃ | 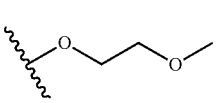 [SMILES: *OCCOC] | SO₂CH₃ | 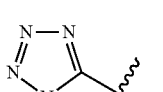 | 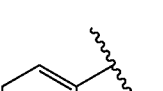 | yellow solid (60-62) |
| 2-20 | CH₃ | 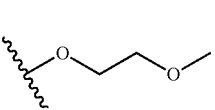 [SMILES: *OCCOC] | SO₂CH₃ | 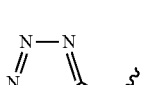 |  | |
| 2-21 | CH₃ | 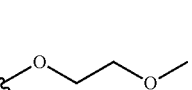 | SO₂CH₃ | 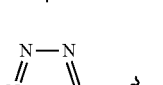 | 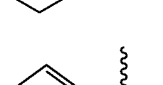 | yellow oil |
| 2-22 | CH₃ | 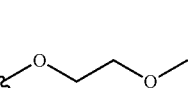 | SO₂CH₃ | 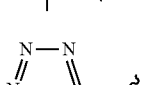 | 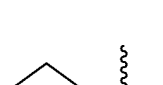 | |
| 2-23 | CH₃ | 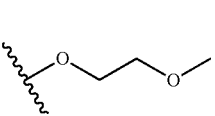 [SMILES: *OCCOC] | SO₂CH₃ | 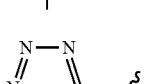 |  | |

TABLE 2-continued

Structures and Physical Properties of Part of Compounds of Formula I

| Compound | X₁ | X₂ | X₃ | Q | Z | Appearance (Melting Point ° C.) |
|---|---|---|---|---|---|---|
| 2-24 | CH₃ | -O-CH₂CH₂-OCH₃ | SO₂CH₃ | 1-methyl-tetrazol-5-yl | cyclohexa-1,3-dien-1-yl | |
| 2-25 | CH₃ | -O-CH₂-(tetrahydrofuran-2-yl) | SO₂CH₃ | 1-methyl-tetrazol-5-yl | cyclohex-1-en-1-yl | |
| 2-26 | CH₃ | -O-CH₂-(tetrahydrofuran-2-yl) | SO₂CH₃ | 1-methyl-tetrazol-5-yl | cyclohex-3-en-1-yl | |
| 2-27 | CH₃ | -O-CH₂-(tetrahydrofuran-2-yl) | SO₂CH₃ | 1-methyl-tetrazol-5-yl | cyclopent-1-en-1-yl | |
| 2-28 | CH₃ | -O-CH₂-(tetrahydrofuran-2-yl) | SO₂CH₃ | 1-methyl-tetrazol-5-yl | cyclopent-3-en-1-yl | |
| 2-29 | CH₃ | -O-CH₂-(tetrahydrofuran-2-yl) | SO₂CH₃ | 1-methyl-tetrazol-5-yl | 4-(prop-1-en-2-yl)cyclohex-1-en-1-yl | |
| 2-30 | CH₃ | -O-CH₂-(tetrahydrofuran-2-yl) | SO₂CH₃ | 1-methyl-tetrazol-5-yl | cyclohexa-1,3-dien-1-yl | |
| 2-31 | CH₃ | -O-CH₂CH₂-(1,3-dioxolan-2-yl) | SO₂CH₃ | 1-methyl-tetrazol-5-yl | cyclohex-1-en-1-yl | |
| 2-32 | CH₃ | -O-CH₂CH₂-(1,3-dioxolan-2-yl) | SO₂CH₃ | 1-methyl-tetrazol-5-yl | cyclohex-3-en-1-yl | |
| 2-33 | CH₃ | -O-CH₂CH₂-(1,3-dioxolan-2-yl) | SO₂CH₃ | 1-methyl-tetrazol-5-yl | cyclopent-1-en-1-yl | |

TABLE 2-continued

Structures and Physical Properties of Part of Compounds of Formula I

| Compound | X₁ | X₂ | X₃ | Q | Z | Appearance (Melting Point ° C.) |
|---|---|---|---|---|---|---|
| 2-34 | CH₃ | (2-(1,3-dioxolan-2-yl)ethoxy) | SO₂CH₃ | 1-methyltetrazol-5-yl | cyclopent-3-en-1-yl | |
| 2-35 | CH₃ | (2-(1,3-dioxolan-2-yl)ethoxy) | SO₂CH₃ | 1-methyltetrazol-5-yl | 4-(prop-1-en-2-yl)cyclohex-1-en-1-yl | |
| 2-36 | CH₃ | (2-(1,3-dioxolan-2-yl)ethoxy) | SO₂CH₃ | 1-methyltetrazol-5-yl | cyclohexa-2,5-dien-1-yl | |
| 2-37 | CH₃ | 4,5-dihydroisoxazol-3-yl | SO₂CH₃ | 1-methyltetrazol-5-yl | cyclohex-1-en-1-yl | yellow oil |
| 2-38 | CH₃ | 4,5-dihydroisoxazol-3-yl | SO₂CH₃ | 1-methyltetrazol-5-yl | cyclohex-3-en-1-yl | |
| 2-39 | CH₃ | 4,5-dihydroisoxazol-3-yl | SO₂CH₃ | 1-methyltetrazol-5-yl | cyclopent-1-en-1-yl | |
| 2-40 | CH₃ | 4,5-dihydroisoxazol-3-yl | SO₂CH₃ | 1-methyltetrazol-5-yl | cyclopent-3-en-1-yl | |
| 2-41 | CH₃ | 4,5-dihydroisoxazol-3-yl | SO₂CH₃ | 1-methyltetrazol-5-yl | 4-(prop-1-en-2-yl)cyclohex-1-en-1-yl | |
| 2-42 | CH₃ | 4,5-dihydroisoxazol-3-yl | SO₂CH₃ | 1-methyltetrazol-5-yl | cyclohexa-2,5-dien-1-yl | |
| 2-43 | CH₃ | CH₃ | SO₂CH₃ | 1-methyltetrazol-5-yl | cyclohex-1-en-1-yl | white solid (91-93) |

TABLE 2-continued

Structures and Physical Properties of Part of Compounds of Formula I

| Compound | X₁ | X₂ | X₃ | Q | Z | Appearance (Melting Point ° C.) |
|---|---|---|---|---|---|---|
| 2-44 | CH₃ | CH₃ | SO₂CH₃ | 1-methyltetrazol-5-yl | cyclohex-3-en-1-yl | |
| 2-45 | CH₃ | CH₃ | SO₂CH₃ | 1-methyltetrazol-5-yl | cyclopent-1-en-1-yl | |
| 2-46 | CH₃ | CH₃ | SO₂CH₃ | 1-methyltetrazol-5-yl | cyclopent-3-en-1-yl | |
| 2-47 | CH₃ | CH₃ | SO₂CH₃ | 1-methyltetrazol-5-yl | 4-(prop-1-en-2-yl)cyclohex-1-en-1-yl | |
| 2-48 | CH₃ | CH₃ | SO₂CH₃ | 1-methyltetrazol-5-yl | cyclohexa-2,4-dien-1-yl | |
| 2-49 | CH₃ | CH₂OCH₃ | SO₂CH₃ | 1-methyltetrazol-5-yl | cyclohex-1-en-1-yl | |
| 2-50 | CH₃ | CH₂OCH₃ | SO₂CH₃ | 1-methyltetrazol-5-yl | cyclohex-3-en-1-yl | |
| 2-51 | CH₃ | CH₂OCH₃ | SO₂CH₃ | 1-methyltetrazol-5-yl | cyclopent-1-en-1-yl | |
| 2-52 | CH₃ | CH₂OCH₃ | SO₂CH₃ | 1-methyltetrazol-5-yl | cyclopent-3-en-1-yl | |
| 2-53 | CH₃ | CH₂OCH₃ | SO₂CH₃ | 1-methyltetrazol-5-yl | 4-(prop-1-en-2-yl)cyclohex-1-en-1-yl | |

TABLE 2-continued

Structures and Physical Properties of Part of Compounds of Formula I

| Compound | $X_1$ | $X_2$ | $X_3$ | Q | Z | Appearance (Melting Point ° C.) |
|---|---|---|---|---|---|---|
| 2-54 | $CH_3$ | -CH2-O-CH3 | $SO_2CH_3$ | N-methyl tetrazole | cyclohexadienyl | |
| 2-55 | Cl | -CH2-O-CH3 | $SO_2CH_3$ | N-methyl tetrazole | cyclohexenyl | pale yellow oil |
| 2-56 | Cl | -CH2-O-CH3 | $SO_2CH_3$ | N-methyl tetrazole | cyclohexenyl | |
| 2-57 | Cl | -CH2-O-CH3 | $SO_2CH_3$ | N-methyl tetrazole | cyclopentenyl | |
| 2-58 | Cl | -CH2-O-CH3 | $SO_2CH_3$ | N-methyl tetrazole | cyclopentenyl | |
| 2-59 | Cl | -CH2-O-CH3 | $SO_2CH_3$ | N-methyl tetrazole | 4-isopropenylcyclohexenyl | |
| 2-60 | Cl | -CH2-O-CH3 | $SO_2CH_3$ | N-methyl tetrazole | cyclohexadienyl | |
| 2-61 | Cl | -CH2-O-CH2CH3 | $SO_2CH_3$ | N-methyl tetrazole | cyclohexenyl | pale yellow oil |
| 2-62 | Cl | -CH2-O-CH2CH3 | $SO_2CH_3$ | N-methyl tetrazole | cyclohexenyl | |
| 2-63 | Cl | -CH2-O-CH2CH3 | $SO_2CH_3$ | N-methyl tetrazole | cyclopentenyl | |

TABLE 2-continued

Structures and Physical Properties of Part of Compounds of Formula I

| Compound | $X_1$ | $X_2$ | $X_3$ | Q | Z | Appearance (Melting Point ° C.) |
|---|---|---|---|---|---|---|
| 2-64 | Cl | —O—ethyl | $SO_2CH_3$ | N-methyl tetrazol-5-yl | cyclopentenyl | |
| 2-65 | Cl | —O—ethyl | $SO_2CH_3$ | N-methyl tetrazol-5-yl | 4-isopropenylcyclohex-1-enyl | |
| 2-66 | Cl | —O—ethyl | $SO_2CH_3$ | N-methyl tetrazol-5-yl | cyclohexa-2,5-dien-1-yl | |
| 2-67 | Cl | —O—CH$_2$CF$_3$ | $SO_2CH_3$ | N-methyl tetrazol-5-yl | cyclohex-1-enyl | |
| 2-68 | Cl | —O—CH$_2$CF$_3$ | $SO_2CH_3$ | N-methyl tetrazol-5-yl | cyclohex-3-enyl | |
| 2-69 | Cl | —O—CH$_2$CF$_3$ | $SO_2CH_3$ | N-methyl tetrazol-5-yl | cyclopent-1-enyl | |
| 2-70 | Cl | —O—CH$_2$CF$_3$ | $SO_2CH_3$ | N-methyl tetrazol-5-yl | cyclopentenyl | |
| 2-71 | Cl | —O—CH$_2$CF$_3$ | $SO_2CH_3$ | N-methyl tetrazol-5-yl | 4-isopropenylcyclohex-1-enyl | |
| 2-72 | Cl | —O—CH$_2$CF$_3$ | $SO_2CH_3$ | N-methyl tetrazol-5-yl | cyclohexa-2,5-dien-1-yl | |
| 2-73 | Cl | —O—CH$_2$CH$_2$—O—CH$_3$ | $SO_2CH_3$ | N-methyl tetrazol-5-yl | cyclohex-1-enyl | |

TABLE 2-continued

Structures and Physical Properties of Part of Compounds of Formula I

| Compound | $X_1$ | $X_2$ | $X_3$ | Q | Z | Appearance (Melting Point ° C.) |
|---|---|---|---|---|---|---|
| 2-74 | Cl | -O-CH2CH2-O-CH3 | SO2CH3 | N-methyl-tetrazol-5-yl | cyclohex-3-en-1-yl | |
| 2-75 | Cl | -O-CH2CH2-O-CH3 | SO2CH3 | N-methyl-tetrazol-5-yl | cyclopent-1-en-1-yl | |
| 2-76 | Cl | -O-CH2CH2-O-CH3 | SO2CH3 | N-methyl-tetrazol-5-yl | cyclopent-3-en-1-yl | |
| 2-77 | Cl | -O-CH2CH2-O-CH3 | SO2CH3 | N-methyl-tetrazol-5-yl | 4-(prop-1-en-2-yl)cyclohex-1-en-1-yl | |
| 2-78 | Cl | -O-CH2CH2-O-CH3 | SO2CH3 | N-methyl-tetrazol-5-yl | cyclohexa-2,4-dien-1-yl | |
| 2-79 | Cl | -O-CH2-(tetrahydrofuran-2-yl) | SO2CH3 | N-methyl-tetrazol-5-yl | cyclohex-1-en-1-yl | |
| 2-80 | Cl | -O-CH2-(tetrahydrofuran-2-yl) | SO2CH3 | N-methyl-tetrazol-5-yl | cyclohex-3-en-1-yl | |
| 2-81 | Cl | -O-CH2-(tetrahydrofuran-2-yl) | SO2CH3 | N-methyl-tetrazol-5-yl | cyclopent-1-en-1-yl | |
| 2-82 | Cl | -O-CH2-(tetrahydrofuran-2-yl) | SO2CH3 | N-methyl-tetrazol-5-yl | cyclopent-3-en-1-yl | |
| 2-83 | Cl | -O-CH2-(tetrahydrofuran-2-yl) | SO2CH3 | N-methyl-tetrazol-5-yl | 4-(prop-1-en-2-yl)cyclohex-1-en-1-yl | |

TABLE 2-continued

Structures and Physical Properties of Part of Compounds of Formula I

| Compound | X₁ | X₂ | X₃ | Q | Z | Appearance (Melting Point ° C.) |
|---|---|---|---|---|---|---|
| 2-84 | Cl | | SO₂CH₃ | | | |
| 2-85 | Cl | | SO₂CH₃ | | | |
| 2-86 | Cl | | SO₂CH₃ | | | |
| 2-87 | Cl | | SO₂CH₃ | | | |
| 2-88 | Cl | | SO₂CH₃ | | | |
| 2-89 | Cl | | SO₂CH₃ | | | |
| 2-90 | Cl | | SO₂CH₃ | | | |
| 2-91 | Cl | | SO₂CH₃ | | | |
| 2-92 | Cl | | SO₂CH₃ | | | |
| 2-93 | Cl | | SO₂CH₃ | | | |

TABLE 2-continued

Structures and Physical Properties of Part of Compounds of Formula I

| Compound | X₁ | X₂ | X₃ | Q | Z | Appearance (Melting Point ° C.) |
|---|---|---|---|---|---|---|
| 2-94 | Cl | 4,5-dihydroisoxazol-3-yl | SO₂CH₃ | 1-methyl-1H-tetrazol-5-yl | cyclopent-3-en-1-yl | |
| 2-95 | Cl | 4,5-dihydroisoxazol-3-yl | SO₂CH₃ | 1-methyl-1H-tetrazol-5-yl | 4-(prop-1-en-2-yl)cyclohex-1-en-1-yl | |
| 2-96 | Cl | 4,5-dihydroisoxazol-3-yl | SO₂CH₃ | 1-methyl-1H-tetrazol-5-yl | cyclohexa-2,4-dien-1-yl | |
| 2-97 | Cl | CH₃ | SO₂CH₃ | 1-methyl-1H-tetrazol-5-yl | cyclohex-1-en-1-yl | pale yellow solid (90-92) |
| 2-98 | Cl | CH₃ | SO₂CH₃ | 1-methyl-1H-tetrazol-5-yl | cyclohex-3-en-1-yl | |
| 2-99 | Cl | CH₃ | SO₂CH₃ | 1-methyl-1H-tetrazol-5-yl | cyclopent-1-en-1-yl | |
| 2-100 | Cl | CH₃ | SO₂CH₃ | 1-methyl-1H-tetrazol-5-yl | cyclopent-3-en-1-yl | |
| 2-101 | Cl | CH₃ | SO₂CH₃ | 1-methyl-1H-tetrazol-5-yl | 4-(prop-1-en-2-yl)cyclohex-1-en-1-yl | |
| 2-102 | Cl | CH₃ | SO₂CH₃ | 1-methyl-1H-tetrazol-5-yl | cyclohexa-2,4-dien-1-yl | |
| 2-103 | Cl | CH₃OCH₂– | SO₂CH₃ | 1-methyl-1H-tetrazol-5-yl | cyclohex-1-en-1-yl | pale yellow solid (155-157) |

TABLE 2-continued

Structures and Physical Properties of Part of Compounds of Formula I

| Compound | X₁ | X₂ | X₃ | Q | Z | Appearance (Melting Point ° C.) |
|---|---|---|---|---|---|---|
| 2-104 | Cl | -CH₂-O-CH₃ | SO₂CH₃ | 1-methyltetrazol-5-yl | cyclohex-3-en-1-yl | off-white solid (125-127) |
| 2-105 | Cl | -CH₂-O-CH₃ | SO₂CH₃ | 1-methyltetrazol-5-yl | cyclopent-1-en-1-yl | pale yellow oil |
| 2-106 | Cl | -CH₂-O-CH₃ | SO₂CH₃ | 1-methyltetrazol-5-yl | cyclopent-3-en-1-yl | brown solid (135-137) |
| 2-107 | Cl | -CH₂-O-CH₃ | SO₂CH₃ | 1-methyltetrazol-5-yl | 4-(prop-1-en-2-yl)cyclohex-1-en-1-yl | |
| 2-108 | Cl | -CH₂-O-CH₃ | SO₂CH₃ | 1-methyltetrazol-5-yl | cyclohexa-2,5-dien-1-yl | |
| 2-109 | Cl | -CH₂-O-CH₂-CF₃ | SO₂CH₃ | 1-methyltetrazol-5-yl | cyclohex-1-en-1-yl | |
| 2-110 | Cl | -CH₂-O-CH₂-CF₃ | SO₂CH₃ | 1-methyltetrazol-5-yl | cyclohex-3-en-1-yl | |
| 2-111 | Cl | -CH₂-O-CH₂-CF₃ | SO₂CH₃ | 1-methyltetrazol-5-yl | cyclopent-1-en-1-yl | |
| 2-112 | Cl | -CH₂-O-CH₂-CF₃ | SO₂CH₃ | 1-methyltetrazol-5-yl | cyclopent-3-en-1-yl | |
| 2-113 | Cl | -CH₂-O-CH₂-CF₃ | SO₂CH₃ | 1-methyltetrazol-5-yl | 4-(prop-1-en-2-yl)cyclohex-1-en-1-yl | |

TABLE 2-continued

Structures and Physical Properties of Part of Compounds of Formula I

| Compound | $X_1$ | $X_2$ | $X_3$ | Q | Z | Appearance (Melting Point ° C.) |
|---|---|---|---|---|---|---|
| 2-114 | Cl | -CH2-O-CH2-CF3 | SO2CH3 | N-methyltetrazolyl | cyclohexa-1,3-dienyl | |
| 2-115 | SO2CH3 | H | Cl | N-methyltetrazolyl | cyclohexenyl | |
| 2-116 | SO2CH3 | H | Cl | N-methyltetrazolyl | cyclohexenyl | |
| 2-117 | SO2CH3 | H | Cl | N-methyltetrazolyl | cyclopentenyl | |
| 2-118 | SO2CH3 | H | Cl | N-methyltetrazolyl | cyclopentenyl | |
| 2-119 | SO2CH3 | H | Cl | N-methyltetrazolyl | 4-isopropenylcyclohexenyl | |
| 2-120 | SO2CH3 | H | Cl | N-methyltetrazolyl | cyclohexa-1,3-dienyl | |
| 2-121 | Cl | Cl | SO2CH3 | N-methyltetrazolyl | cyclohexenyl | |
| 2-122 | Cl | Cl | SO2CH3 | N-methyltetrazolyl | cyclohexenyl | |
| 2-123 | Cl | Cl | SO2CH3 | N-methyltetrazolyl | cyclopentenyl | |

TABLE 2-continued

Structures and Physical Properties of Part of Compounds of Formula I

| Compound | X₁ | X₂ | X₃ | Q | Z | Appearance (Melting Point ° C.) |
|---|---|---|---|---|---|---|
| 2-124 | Cl | Cl | SO₂CH₃ | N-methyltetrazol-5-yl | cyclopent-3-en-1-yl | |
| 2-125 | Cl | Cl | SO₂CH₃ | N-methyltetrazol-5-yl | 4-(prop-1-en-2-yl)cyclohex-1-en-1-yl | |
| 2-126 | Cl | Cl | SO₂CH₃ | N-methyltetrazol-5-yl | cyclohexa-2,4-dien-1-yl | |
| 2-127 | Cl | CH=N-OEt | SO₂CH₃ | N-methyltetrazol-5-yl | cyclohex-1-en-1-yl | |
| 2-128 | Cl | CH=N-OEt | SO₂CH₃ | N-methyltetrazol-5-yl | cyclohex-3-en-1-yl | |
| 2-129 | Cl | CH=N-OEt | SO₂CH₃ | N-methyltetrazol-5-yl | cyclopent-1-en-1-yl | |
| 2-130 | Cl | CH=N-OEt | SO₂CH₃ | N-methyltetrazol-5-yl | cyclopent-3-en-1-yl | |
| 2-131 | Cl | CH=N-OEt | SO₂CH₃ | N-methyltetrazol-5-yl | 4-(prop-1-en-2-yl)cyclohex-1-en-1-yl | |
| 2-132 | Cl | CH=N-OEt | SO₂CH₃ | N-methyltetrazol-5-yl | cyclohexa-2,4-dien-1-yl | |
| 2-133 | CH₃ | CH₂OCH₃ | SO₂CH₃ | N-methyltetrazol-5-yl | cyclohex-1-en-1-yl | |

TABLE 2-continued

Structures and Physical Properties of Part of Compounds of Formula I

| Compound | $X_1$ | $X_2$ | $X_3$ | Q | Z | Appearance (Melting Point ° C.) |
|---|---|---|---|---|---|---|
| 2-134 | $CH_3$ | -OCH$_3$ | $SO_2CH_3$ | N-methyltetrazolyl | cyclohexenyl | |
| 2-135 | $CH_3$ | -OCH$_3$ | $SO_2CH_3$ | N-methyltetrazolyl | cyclopentenyl | |
| 2-136 | CH | -OCH$_3$ | $SO_2CH_3$ | N-methyltetrazolyl | cyclopentenyl | |
| 2-137 | $CH_3$ | -OCH$_3$ | $SO_2CH_3$ | N-methyltetrazolyl | isopropenyl-cyclohexenyl | |
| 2-138 | $CH_3$ | -OCH$_3$ | $SO_2CH_3$ | N-methyltetrazolyl | cyclohexadienyl | |
| 2-139 | $CH_3$ | -OCH$_2$CH$_3$ | $SO_2CH_3$ | N-methyltetrazolyl | cyclohexenyl | |
| 2-140 | $CH_3$ | -OCH$_2$CH$_3$ | $SO_2CH_3$ | N-methyltetrazolyl | cyclohexenyl | |
| 2-141 | $CH_3$ | -OCH$_2$CH$_3$ | $SO_2CH_3$ | N-methyltetrazolyl | cyclopentenyl | |
| 2-142 | CH | -OCH$_2$CH$_3$ | $SO_2CH_3$ | N-methyltetrazolyl | cyclopentenyl | |
| 2-143 | CH | -OCH$_2$CH$_3$ | $SO_2CH_3$ | N-methyltetrazolyl | isopropenyl-cyclohexenyl | |

TABLE 2-continued
Structures and Physical Properties of Part of Compounds of Formula I
| Compound | X$_1$ | X$_2$ | X$_3$ | Q | Z | Appearance (Melting Point ° C.) |
|---|---|---|---|---|---|---|
| 2-144 | CH$_3$ | 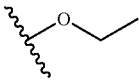 | SO$_2$CH$_3$ | 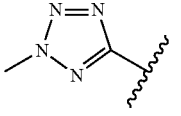 [SMILES: *c1nnn(C)n1] | 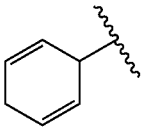 | |
| 2-145 | CH$_3$ | 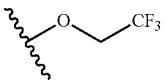 | SO$_2$CH$_3$ | 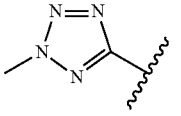 [SMILES: *c1nnn(C)n1] | 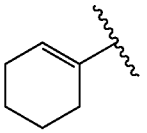 [SMILES: *C1=CCCCC1] | |
| 2-146 | CH$_3$ | 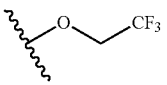 | SO$_2$CH$_3$ | 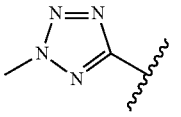 [SMILES: *c1nnn(C)n1] | 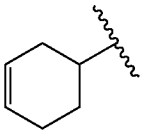 [SMILES: *C1CC=CCC1] | |
| 2-147 | CH$_3$ | 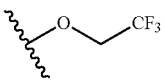 [SMILES: *OCC(F)(F)F] | SO$_2$CH$_3$ | 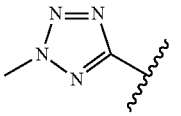 [SMILES: *c1nnn(C)n1] | 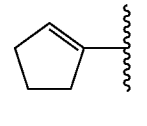 [SMILES: *C1=CCCC1] | |
| 2-148 | CH$_3$ | 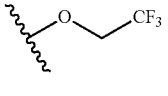 | SO$_2$CH$_3$ | 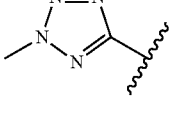 | 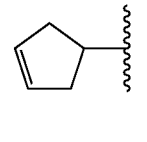 | |
| 2-149 | CH$_3$ | 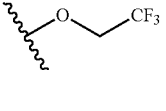 [SMILES: *OCC(F)(F)F] | SO$_2$CH$_3$ | 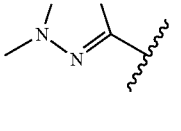 | 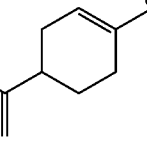 | |
| 2-150 | CH$_3$ | 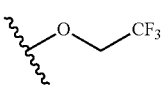 | SO$_2$CH$_3$ | 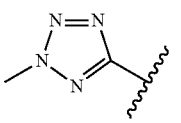 | 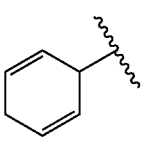 [SMILES: *C1C=CCC=C1] | |
| 2-151 | CH$_3$ | 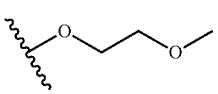 [SMILES: *OCCOC] | SO$_2$CH$_3$ | 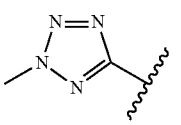 [SMILES: *c1nnn(C)n1] | 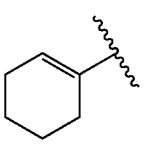 | |
| 2-152 | CH$_3$ | 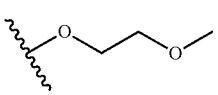 [SMILES: *OCCOC] | SO$_2$CH$_3$ | 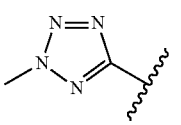 [SMILES: *c1nnn(C)n1] | 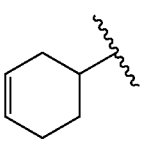 [SMILES: *C1CC=CCC1] | |
| 2-153 | CH$_3$ | 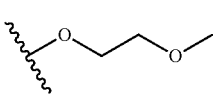 [SMILES: *OCCOC] | SO$_2$CH$_3$ | 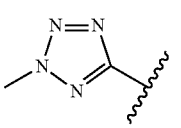 [SMILES: *c1nnn(C)n1] | 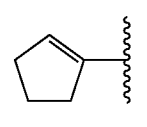 [SMILES: *C1=CCCC1] | |

TABLE 2-continued

Structures and Physical Properties of Part of Compounds of Formula I

| Compound | X₁ | X₂ | X₃ | Q | Z | Appearance (Melting Point °C.) |
|---|---|---|---|---|---|---|
| 2-154 | CH₃ | -O-CH₂CH₂-O-CH₃ | SO₂CH₃ | 2-methyltetrazol-5-yl | cyclopent-3-en-1-yl | |
| 2-155 | CH₃ | -O-CH₂CH₂-O-CH₃ | SO₂CH₃ | 2-methyltetrazol-5-yl | 4-(prop-1-en-2-yl)cyclohex-1-en-1-yl | |
| 2-156 | CH₃ | -O-CH₂CH₂-O-CH₃ | SO₂CH₃ | 2-methyltetrazol-5-yl | cyclohexa-2,4-dien-1-yl | |
| 2-157 | CH₃ | -O-CH₂-(tetrahydrofuran-2-yl) | SO₂CH₃ | 2-methyltetrazol-5-yl | cyclohex-1-en-1-yl | |
| 2-158 | CH₃ | -O-CH₂-(tetrahydrofuran-2-yl) | SO₂CH₃ | 2-methyltetrazol-5-yl | cyclohex-3-en-1-yl | |
| 2-159 | CH₃ | -O-CH₂-(tetrahydrofuran-2-yl) | SO₂CH₃ | 2-methyltetrazol-5-yl | cyclopent-1-en-1-yl | |
| 2-160 | CH | -O-CH₂-(tetrahydrofuran-2-yl) | SO₂CH₃ | 2-methyltetrazol-5-yl | cyclopent-3-en-1-yl | |
| 2-161 | CH | -O-CH₂-(tetrahydrofuran-2-yl) | SO₂CH₃ | 2-methyltetrazol-5-yl | 4-(prop-1-en-2-yl)cyclohex-1-en-1-yl | |
| 2-162 | CH₃ | -O-CH₂-(tetrahydrofuran-2-yl) | SO₂CH₃ | 2-methyltetrazol-5-yl | cyclohexa-2,4-dien-1-yl | |
| 2-163 | CH₃ | -O-CH₂CH₂-(1,3-dioxolan-2-yl) | SO₂CH₃ | 2-methyltetrazol-5-yl | cyclohex-1-en-1-yl | |

TABLE 2-continued

Structures and Physical Properties of Part of Compounds of Formula I

| Compound | $X_1$ | $X_2$ | $X_3$ | Q | Z | Appearance (Melting Point ° C.) |
|---|---|---|---|---|---|---|
| 2-164 | $CH_3$ | (2-(1,3-dioxolan-2-yl)ethoxy) | $SO_2CH_3$ | 2-methyl-2H-tetrazol-5-yl | cyclohex-3-en-1-yl | |
| 2-165 | $CH_3$ | (2-(1,3-dioxolan-2-yl)ethoxy) | $SO_2CH_3$ | 2-methyl-2H-tetrazol-5-yl | cyclopent-1-en-1-yl | |
| 2-166 | $CH_3$ | (2-(1,3-dioxolan-2-yl)ethoxy) | $SO_2CH_3$ | 2-methyl-2H-tetrazol-5-yl | cyclopent-2-en-1-yl | |
| 2-167 | $CH_3$ | (2-(1,3-dioxolan-2-yl)ethoxy) | $SO_2CH_3$ | 2-methyl-2H-tetrazol-5-yl | 4-(prop-1-en-2-yl)cyclohex-1-en-1-yl | |
| 2-168 | $CH_3$ | (2-(1,3-dioxolan-2-yl)ethoxy) | $SO_2CH_3$ | 2-methyl-2H-tetrazol-5-yl | cyclohexa-2,4-dien-1-yl | |
| 2-169 | $CH_3$ | 4,5-dihydroisoxazol-3-yl | $SO_2CH_3$ | 2-methyl-2H-tetrazol-5-yl | cyclohex-1-en-1-yl | |
| 2-170 | $CH_3$ | 4,5-dihydroisoxazol-3-yl | $SO_2CH_3$ | 2-methyl-2H-tetrazol-5-yl | cyclohex-3-en-1-yl | |
| 2-171 | $CH_3$ | 4,5-dihydroisoxazol-3-yl | $SO_2CH_3$ | 2-methyl-2H-tetrazol-5-yl | cyclopent-1-en-1-yl | |
| 2-172 | $CH_3$ | 4,5-dihydroisoxazol-3-yl | $SO_2CH_3$ | 2-methyl-2H-tetrazol-5-yl | cyclopent-2-en-1-yl | |
| 2-173 | $CH_3$ | 4,5-dihydroisoxazol-3-yl | $SO_2CH_3$ | 2-methyl-2H-tetrazol-5-yl | 4-(prop-1-en-2-yl)cyclohex-1-en-1-yl | |

TABLE 2-continued
Structures and Physical Properties of Part of Compounds of Formula I
| Compound | X₁ | X₂ | X₃ | Q | Z | Appearance (Melting Point ° C.) |
|---|---|---|---|---|---|---|
| 2-174 | CH₃ | 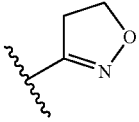 | SO₂CH₃ | 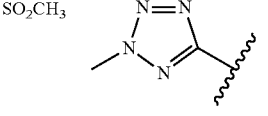 | 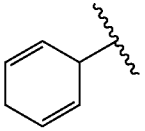 [SMILES: *C1C=CCC=C1] | |
| 2-175 | CH₃ | CH₃ | SO₂CH₃ | 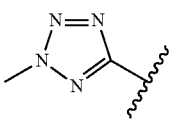 | 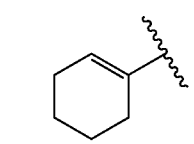 [SMILES: *C1=CCCCC1] | |
| 2-176 | CH₃ | CH₃ | SO₂CH₃ | 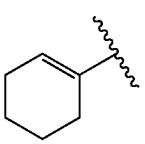 [SMILES: *C1=CCCCC1] | 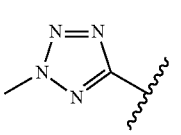 [SMILES: *c1nnn(C)n1] | |
| 2-177 | CH₃ | CH₃ | SO₂CH₃ | 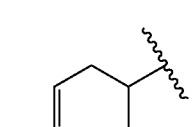 | 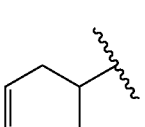 | |
| 2-178 | CH₃ | CH₃ | SO₂CH₃ | 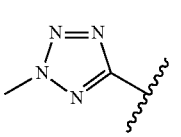 | 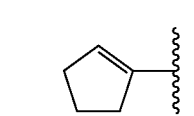 [SMILES: *C1=CCCC1] | |
| 2-179 | CH₃ | CH₃ | SO₂CH₃ | 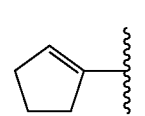 [SMILES: *C1=CCCC1] | 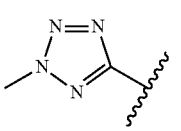 | |
| 2-180 | CH | CH₃ | SO₂CH₃ | 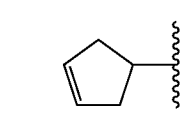 | 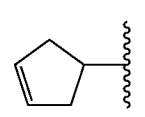 | |
| 2-181 | CH | 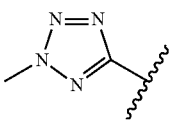 | SO₂CH₃ | 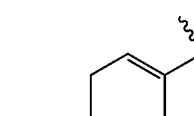 | 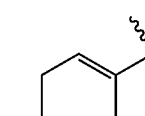 | |
| 2-182 | CH₃ | 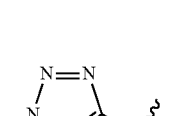 | SO₂CH₃ |  | 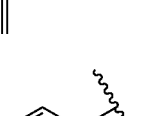 | |
| 2-183 | CH₃ | 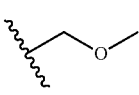 | SO₂CH₃ | 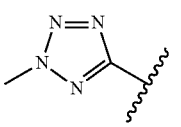 [SMILES: *c1nnn(C)n1] | 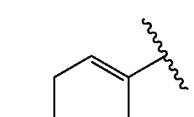 | |

TABLE 2-continued

Structures and Physical Properties of Part of Compounds of Formula I

| Compound | $X_1$ | $X_2$ | $X_3$ | Q | Z | Appearance (Melting Point ° C.) |
|---|---|---|---|---|---|---|
| 2-184 | $CH_3$ | -CH2OCH3 | $SO_2CH_3$ | 2-methyltetrazol-5-yl | cyclopent-3-en-1-yl | |
| 2-185 | $CH_3$ | -CH2OCH3 | $SO_2CH_3$ | 2-methyltetrazol-5-yl | 4-(prop-1-en-2-yl)cyclohex-1-en-1-yl | |
| 2-186 | $CH_3$ | -CH2OCH3 | $SO_2CH_3$ | 2-methyltetrazol-5-yl | cyclohexa-2,4-dien-1-yl | |
| 2-187 | Cl | -CH(OCH3)- | $SO_2CH_3$ | 2-methyltetrazol-5-yl | cyclohex-1-en-1-yl | |
| 2-188 | Cl | -CH(OCH3)- | $SO_2CH_3$ | 2-methyltetrazol-5-yl | cyclohex-3-en-1-yl | |
| 2-189 | Cl | -CH(OCH3)- | $SO_2CH_3$ | 2-methyltetrazol-5-yl | cyclopent-1-en-1-yl | |
| 2-190 | Cl | -CH(OCH3)- | $SO_2CH_3$ | 2-methyltetrazol-5-yl | cyclopent-3-en-1-yl | |
| 2-191 | Cl | -CH(OCH3)- | $SO_2CH_3$ | 2-methyltetrazol-5-yl | 4-(prop-1-en-2-yl)cyclohex-1-en-1-yl | |
| 2-192 | Cl | -CH(OCH3)- | $SO_2CH_3$ | 2-methyltetrazol-5-yl | cyclohexa-2,4-dien-1-yl | |
| 2-193 | Cl | -CH(OCH2CH3)- | $SO_2CH_3$ | 2-methyltetrazol-5-yl | cyclohex-1-en-1-yl | |

TABLE 2-continued
Structures and Physical Properties of Part of Compounds of Formula I
| Compound | $X_1$ | $X_2$ | $X_3$ | Q | Z | Appearance (Melting Point ° C.) |
|---|---|---|---|---|---|---|
| 2-194 | Cl | 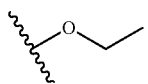 [SMILES: *OCC] | $SO_2CH_3$ | 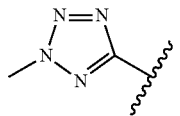 | 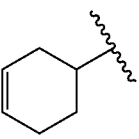 [SMILES: *C1CC=CCC1] | |
| 2-195 | Cl | 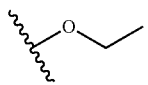 [SMILES: *OCC] | $SO_2CH_3$ | 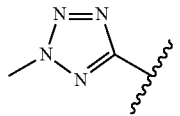 | 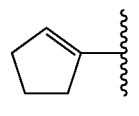 | |
| 2-196 | Cl | 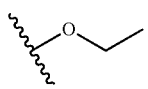 [SMILES: *OCC] | $SO_2CH_3$ | 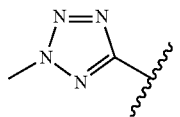 [SMILES: *c1nnn(C)n1] | 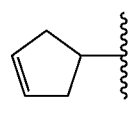 [SMILES: *C1CC=CC1] | |
| 2-197 | Cl | 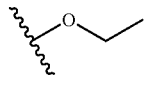 [SMILES: *OCC] | $SO_2CH_3$ | 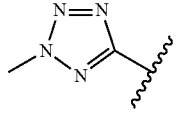 [SMILES: *c1nnn(C)n1] | 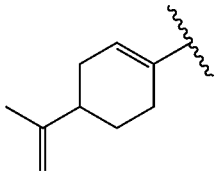 [SMILES: *C1=CCC(C(=C)C)CC1] | |
| 2-198 | Cl | 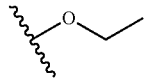 [SMILES: *OCC] | $SO_2CH_3$ | 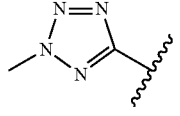 [SMILES: *c1nnn(C)n1] | 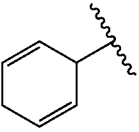 | |
| 2-199 | Cl | 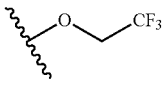 [SMILES: *OCC(F)(F)F] | $SO_2CH_3$ | 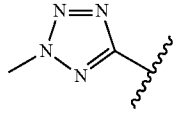 | 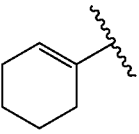 [SMILES: *C1=CCCCC1] | |
| 2-200 | Cl | 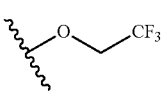 | $SO_2CH_3$ | 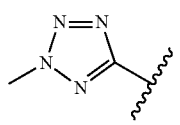 [SMILES: *c1nnn(C)n1] | 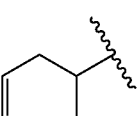 | |
| 2-201 | Cl | 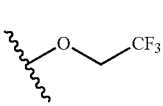 [SMILES: *OCC(F)(F)F] | $SO_2CH_3$ | 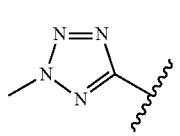 [SMILES: *c1nnn(C)n1] | 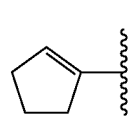 [SMILES: *C1=CCCC1] | |
| 2-202 | Cl | 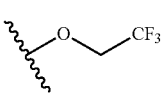 [SMILES: *OCC(F)(F)F] | $SO_2CH_3$ | 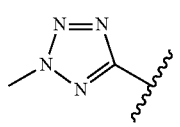 [SMILES: *c1nnn(C)n1] | 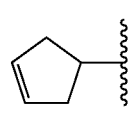 [SMILES: *C1CC=CC1] | |
| 2-203 | Cl | 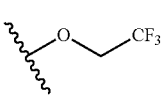 [SMILES: *OCC(F)(F)F] | $SO_2CH_3$ | 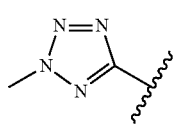 [SMILES: *c1nnn(C)n1] | 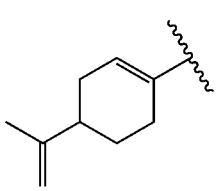 [SMILES: *C1=CCC(C(=C)C)CC1] | |

TABLE 2-continued

Structures and Physical Properties of Part of Compounds of Formula I

| Compound | $X_1$ | $X_2$ | $X_3$ | Q | Z | Appearance (Melting Point ° C.) |
|---|---|---|---|---|---|---|
| 2-204 | Cl | —O—CH$_2$—CF$_3$ | SO$_2$CH$_3$ | 2-methyl-tetrazol-5-yl | cyclohexa-1,3-dien-1-yl | |
| 2-205 | Cl | —O—CH$_2$CH$_2$—O—CH$_3$ | SO$_2$CH$_3$ | 2-methyl-tetrazol-5-yl | cyclohex-1-en-1-yl | |
| 2-206 | Cl | —O—CH$_2$CH$_2$—O—CH$_3$ | SO$_2$CH$_3$ | 2-methyl-tetrazol-5-yl | cyclohex-3-en-1-yl | |
| 2-207 | Cl | —O—CH$_2$CH$_2$—O—CH$_3$ | SO$_2$CH$_3$ | 2-methyl-tetrazol-5-yl | cyclopent-1-en-1-yl | |
| 2-208 | Cl | —O—CH$_2$CH$_2$—O—CH$_3$ | SO$_2$CH$_3$ | 2-methyl-tetrazol-5-yl | cyclopent-3-en-1-yl | |
| 2-209 | Cl | —O—CH$_2$CH$_2$—O—CH$_3$ | SO$_2$CH$_3$ | 2-methyl-tetrazol-5-yl | 4-(prop-1-en-2-yl)cyclohex-1-en-1-yl | |
| 2-210 | Cl | —O—CH$_2$CH$_2$—O—CH$_3$ | SO$_2$CH$_3$ | 2-methyl-tetrazol-5-yl | cyclohexa-1,3-dien-1-yl | |
| 2-211 | Cl | —O—CH$_2$-(tetrahydrofuran-2-yl) | SO$_2$CH$_3$ | 2-methyl-tetrazol-5-yl | cyclohex-1-en-1-yl | |
| 2-212 | Cl | —O—CH$_2$-(tetrahydrofuran-2-yl) | SO$_2$CH$_3$ | 2-methyl-tetrazol-5-yl | cyclohex-3-en-1-yl | |
| 2-213 | Cl | —O—CH$_2$-(tetrahydrofuran-2-yl) | SO$_2$CH$_3$ | 2-methyl-tetrazol-5-yl | cyclopent-1-en-1-yl | |

TABLE 2-continued

Structures and Physical Properties of Part of Compounds of Formula I

| Compound | X₁ | X₂ | X₃ | Q | Z | Appearance (Melting Point ° C.) |
|---|---|---|---|---|---|---|
| 2-214 | Cl | -O-CH₂-(tetrahydrofuran-2-yl) | SO₂CH₃ | 2-methyl-2H-tetrazol-5-yl | cyclopent-2-en-1-yl | |
| 2-215 | Cl | -O-CH₂-(tetrahydrofuran-2-yl) | SO₂CH₃ | 2-methyl-2H-tetrazol-5-yl | 4-(prop-1-en-2-yl)cyclohex-1-en-1-yl | |
| 2-216 | Cl | -O-CH₂-(tetrahydrofuran-2-yl) | SO₂CH₃ | 2-methyl-2H-tetrazol-5-yl | cyclohexa-2,5-dien-1-yl | |
| 2-217 | Cl | -O-CH₂CH₂-(1,3-dioxolan-2-yl) | SO₂CH₃ | 2-methyl-2H-tetrazol-5-yl | cyclohex-1-en-1-yl | |
| 2-218 | Cl | -O-CH₂CH₂-(1,3-dioxolan-2-yl) | SO₂CH₃ | 2-methyl-2H-tetrazol-5-yl | cyclohex-3-en-1-yl | |
| 2-219 | Cl | -O-CH₂CH₂-(1,3-dioxolan-2-yl) | SO₂CH₃ | 2-methyl-2H-tetrazol-5-yl | cyclopent-1-en-1-yl | |
| 2-220 | Cl | -O-CH₂CH₂-(1,3-dioxolan-2-yl) | SO₂CH₃ | 2-methyl-2H-tetrazol-5-yl | cyclopent-2-en-1-yl | |
| 2-221 | Cl | -O-CH₂CH₂-(1,3-dioxolan-2-yl) | SO₂CH₃ | 2-methyl-2H-tetrazol-5-yl | 4-(prop-1-en-2-yl)cyclohex-1-en-1-yl | |
| 2-222 | Cl | -O-CH₂CH₂-(1,3-dioxolan-2-yl) | SO₂CH₃ | 2-methyl-2H-tetrazol-5-yl | cyclohexa-2,5-dien-1-yl | |
| 2-223 | Cl | 4,5-dihydroisoxazol-3-yl | SO₂CH₃ | 2-methyl-2H-tetrazol-5-yl | cyclohex-1-en-1-yl | |

TABLE 2-continued

Structures and Physical Properties of Part of Compounds of Formula I

| Compound | $X_1$ | $X_2$ | $X_3$ | Q | Z | Appearance (Melting Point ° C.) |
|---|---|---|---|---|---|---|
| 2-224 | Cl | 4,5-dihydroisoxazol-3-yl | $SO_2CH_3$ | 2-methyl-2H-tetrazol-5-yl | cyclohex-3-en-1-yl | |
| 2-225 | Cl | 4,5-dihydroisoxazol-3-yl | $SO_2CH_3$ | 2-methyl-2H-tetrazol-5-yl | cyclopent-1-en-1-yl | |
| 2-226 | Cl | 4,5-dihydroisoxazol-3-yl | $SO_2CH_3$ | 2-methyl-2H-tetrazol-5-yl | cyclopent-3-en-1-yl | |
| 2-227 | Cl | 4,5-dihydroisoxazol-3-yl | $SO_2CH_3$ | 2-methyl-2H-tetrazol-5-yl | 4-(prop-1-en-2-yl)cyclohex-1-en-1-yl | |
| 2-228 | Cl | 4,5-dihydroisoxazol-3-yl | $SO_2CH_3$ | 2-methyl-2H-tetrazol-5-yl | cyclohexa-2,5-dien-1-yl | |
| 2-229 | Cl | $CH_3$ | $SO_2CH_3$ | 2-methyl-2H-tetrazol-5-yl | cyclohex-1-en-1-yl | |
| 2-230 | Cl | $CH_3$ | $SO_2CH_3$ | 2-methyl-2H-tetrazol-5-yl | cyclohex-3-en-1-yl | |
| 2-231 | Cl | $CH_3$ | $SO_2CH_3$ | 2-methyl-2H-tetrazol-5-yl | cyclopent-1-en-1-yl | |
| 2-232 | Cl | $CH_3$ | $SO_2CH_3$ | 2-methyl-2H-tetrazol-5-yl | cyclopent-3-en-1-yl | |
| 2-233 | Cl | $CH_3$ | $SO_2CH_3$ | 2-methyl-2H-tetrazol-5-yl | 4-(prop-1-en-2-yl)cyclohex-1-en-1-yl | |

TABLE 2-continued

Structures and Physical Properties of Part of Compounds of Formula I

| Compound | X₁ | X₂ | X₃ | Q | Z | Appearance (Melting Point ° C.) |
|---|---|---|---|---|---|---|
| 2-234 | Cl | CH₃ | SO₂CH₃ | 2-methyl-tetrazol-5-yl | cyclohexa-1,3-dien-1-yl | |
| 2-235 | Cl | CH₂OCH₃ | SO₂CH₃ | 2-methyl-tetrazol-5-yl | cyclohex-1-en-1-yl | yellow solid (82-84) |
| 2-236 | Cl | CH₂OCH₃ | SO₂CH₃ | 2-methyl-tetrazol-5-yl | cyclohex-3-en-1-yl | |
| 2-237 | Cl | CH₂OCH₃ | SO₂CH₃ | 2-methyl-tetrazol-5-yl | cyclopent-1-en-1-yl | yellow solid (128-130) |
| 2-238 | Cl | CH₂OCH₃ | SO₂CH₃ | 2-methyl-tetrazol-5-yl | cyclopent-3-en-1-yl | |
| 2-239 | Cl | CH₂OCH₃ | SO₂CH₃ | 2-methyl-tetrazol-5-yl | 4-(prop-1-en-2-yl)cyclohex-1-en-1-yl | |
| 2-240 | Cl | CH₂OCH₃ | SO₂CH₃ | 2-methyl-tetrazol-5-yl | cyclohexa-1,3-dien-1-yl | |
| 2-241 | Cl | CH₂OCH₂CF₃ | SO₂CH₃ | 2-methyl-tetrazol-5-yl | cyclohex-1-en-1-yl | |
| 2-242 | Cl | CH₂OCH₂CF₃ | SO₂CH₃ | 2-methyl-tetrazol-5-yl | cyclohex-3-en-1-yl | |
| 2-243 | Cl | CH₂OCH₂CF₃ | SO₂CH₃ | 2-methyl-tetrazol-5-yl | cyclopent-1-en-1-yl | |

TABLE 2-continued

Structures and Physical Properties of Part of Compounds of Formula I

| Compound | X₁ | X₂ | X₃ | Q | Z | Appearance (Melting Point ° C.) |
|---|---|---|---|---|---|---|
| 2-244 | Cl | -CH₂-O-CH₂-CF₃ | SO₂CH₃ | 2-methyl-tetrazol-5-yl | cyclopent-3-en-1-yl | |
| 2-245 | Cl | -CH₂-O-CH₂-CF₃ | SO₂CH₃ | 2-methyl-tetrazol-5-yl | 4-(prop-1-en-2-yl)cyclohex-1-en-1-yl | |
| 2-246 | Cl | -CH₂-O-CH₂-CF₃ | SO₂CH₃ | 2-methyl-tetrazol-5-yl | cyclohexa-2,5-dien-1-yl | |
| 2-247 | SO₂CH₃ | H | Cl | 2-methyl-tetrazol-5-yl | cyclohex-1-en-1-yl | |
| 2-248 | SO₂CH₃ | H | Cl | 2-methyl-tetrazol-5-yl | cyclohex-3-en-1-yl | |
| 2-249 | SO₂CH₃ | H | Cl | 2-methyl-tetrazol-5-yl | cyclopent-1-en-1-yl | |
| 2-250 | SO₂CH₃ | H | Cl | 2-methyl-tetrazol-5-yl | cyclopent-3-en-1-yl | |
| 2-251 | SO₂CH₃ | H | Cl | 2-methyl-tetrazol-5-yl | 4-(prop-1-en-2-yl)cyclohex-1-en-1-yl | |
| 2-252 | SO₂CH₃ | H | Cl | 2-methyl-tetrazol-5-yl | cyclohexa-2,5-dien-1-yl | |
| 2-253 | Cl | Cl | SO₂CH₃ | 2-methyl-tetrazol-5-yl | cyclohex-1-en-1-yl | |

TABLE 2-continued
Structures and Physical Properties of Part of Compounds of Formula I
| Compound | $X_1$ | $X_2$ | $X_3$ | Q | Z | Appearance (Melting Point ° C.) |
|---|---|---|---|---|---|---|
| 2-254 | Cl | Cl | $SO_2CH_3$ | 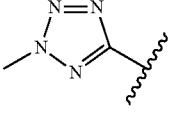 [SMILES: *c1nnn(C)n1] | 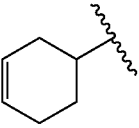 [SMILES: *C1CC=CCC1] | |
| 2-255 | Cl | Cl | $SO_2CH_3$ | 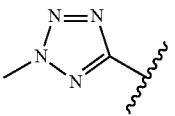 [SMILES: *c1nnn(C)n1] | 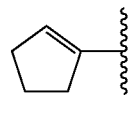 | |
| 2-256 | Cl | Cl | $SO_2CH_3$ | 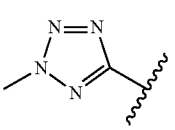 [SMILES: *c1nnn(C)n1] | 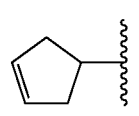 [SMILES: *C1CC=CC1] | |
| 2-257 | Cl | Cl | $SO_2CH_3$ | 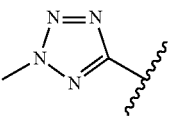 | 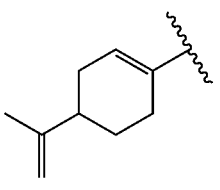 [SMILES: *C1=CCC(C(=C)C)CC1] | |
| 2-258 | Cl | Cl | $SO_2CH_3$ | 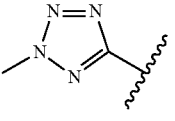 | 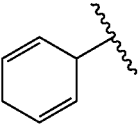 [SMILES: *C1C=CCC=C1] | |
| 2-259 | Cl | 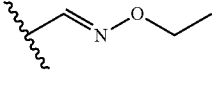 | $SO_2CH_3$ | 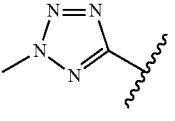 | 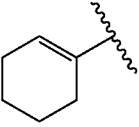 [SMILES: *C1=CCCCC1] | |
| 2-260 | Cl | 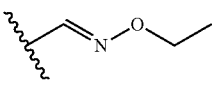 [SMILES: */C=N/OCC] | $SO.CH_3$ | 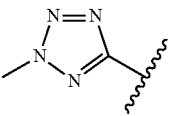 [SMILES: *c1nnn(C)n1] | 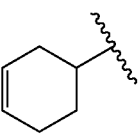 | |
| 2-261 | Cl | 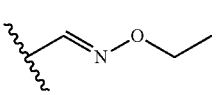 | $SO_2CH_3$ | 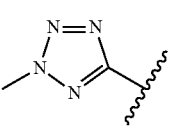 [SMILES: *c1nnn(C)n1] | 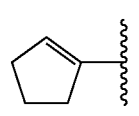 [SMILES: *C1=CCCC1] | |
| 2-262 | Cl | 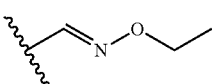 | $SO_2CH_3$ | 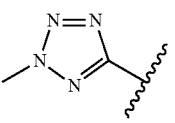 | 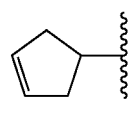 [SMILES: *C1CC=CC1] | |
| 2-263 | Cl | 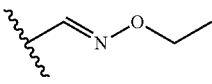 | $SO_2CH_3$ | 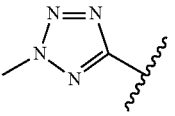 [SMILES: *c1nnn(C)n1] | 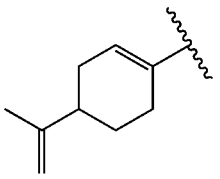 [SMILES: *C1=CCC(C(=C)C)CC1] | |

TABLE 2-continued

Structures and Physical Properties of Part of Compounds of Formula I

| Compound | $X_1$ | $X_2$ | $X_3$ | Q | Z | Appearance (Melting Point °C.) |
|---|---|---|---|---|---|---|
| 2-264 | Cl | -CH=N-O-CH2CH3 | $SO_2CH_3$ | 2-methyl-tetrazol-5-yl | cyclohexa-1,3-dien-yl | |
| 2-265 | $SO_2CH_3$ | H | CFa | 1-methyl-tetrazol-5-yl | cyclohex-1-en-yl | off-white solid (131-133) |
| 2-266 | $SO_2CH_3$ | H | $CF_3$ | 1-methyl-tetrazol-5-yl | cyclopent-1-en-yl | off-white solid (107-109) |
| 2-267 | $NO_2$ | H | Cl | 1-methyl-tetrazol-5-yl | cyclohex-1-en-yl | yellow oil |
| 2-268 | Cl | H | Cl | 1-methyl-tetrazol-5-yl | cyclohex-1-en-yl | pale yellow oil |
| 2-269 | Cl | H | $SO_2CH_3$ | 1-methyl-tetrazol-5-yl | cyclohex-1-en-yl | pale yellow solid (126-128) |
| 2-270 | Cl | -CH2-O-CH2CH2-O-CH3 | $SO_2CH_3$ | 1-methyl-tetrazol-5-yl | cyclohex-1-en-yl | pale yellow oil |
| 2-271 | Cl | H | $NO_2$ | 1-methyl-tetrazol-5-yl | cyclohex-1-en-yl | yellow oil |
| 2-272 | Cl | $CH_3SO_2CH_2$ | $SO_2CH_3$ | 1-methyl-tetrazol-5-yl | cyclohex-1-en-yl | |
| 2-273 | Cl | $CH_3SO_2CH_2$ | $SO_2CH_3$ | 1-methyl-tetrazol-5-yl | cyclopent-1-en-yl | |

TABLE 2-continued

Structures and Physical Properties of Part of Compounds of Formula I

| Compound | $X_1$ | $X_2$ | $X_3$ | Q | Z | Appearance (Melting Point ° C.) |
|---|---|---|---|---|---|---|
| 2-274 | $CH_3$ | -O-CH$_2$CH$_2$-O-CH$_2$CH$_3$ | $SO_2CH_3$ | N-methyl tetrazole | cyclohexenyl | yellow oil |
| 2-275 | $CH_3$ | -O-CH$_2$CH$_2$-O-CH$_2$CH$_3$ | $SO_2CH_3$ | N-methyl tetrazole | cyclopentenyl | yellow oil |
| 2-276 | $SO_2CH$ | H | Cl | N-methyl tetrazole | cyclohexenyl | yellow oil (175-176) |
| 2-277 | $CH_3$ | -O-propyl | $SO_2CH_3$ | N-methyl tetrazole | cyclopentenyl | brown solid (122-124) |
| 2-278 | $CH_3$ | -O-propyl | $SO_2CH_3$ | N-methyl tetrazole | cyclohexenyl | orange yellow solid (139-141) |
| 2-279 | Cl | -CH$_2$-O-propyl | $SO_2CH_3$ | N-methyl tetrazole | cyclohexenyl | orange oil |
| 2-280 | Cl | -O-CH$_2$CH$_2$-O-CH$_2$CH$_3$ | $SO_2CH_3$ | N-methyl tetrazole | cyclohexenyl | yellow oil |
| 2-281 | Cl | -O-CH$_2$CH$_2$CH$_2$-O-CH$_3$ | $SO_2CH_3$ | N-methyl tetrazole | cyclohexenyl | yellow oil |
| 2-282 | Cl | -O-isopropyl | $SO_2CH_3$ | N-methyl tetrazole | cyclohexenyl | pale yellow oil |
| 2-283 | Cl | -O-CH$_2$-cyclopropyl | $SO_2CH_3$ | N-methyl tetrazole | cyclohexenyl | pale yellow oil |

In the compound of the formula I, W is N and the stereo configuration is trans.

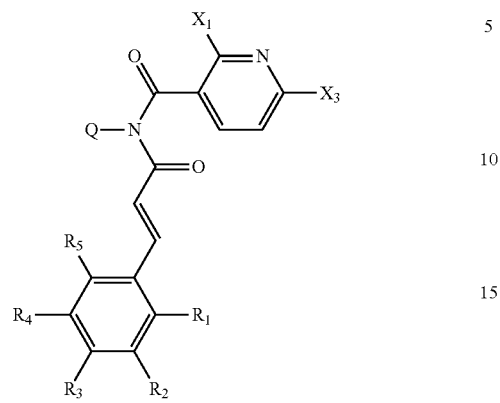

TABLE 3

Structures and Physical Properties of Part of Compounds of Formula 1

| Compound | $X_1$ | $X_3$ | Q | $R_1$ | $R_2$ | $R_3$ | $R_4$ | $R_5$ | Appearance (Melting Point ° C.) |
|---|---|---|---|---|---|---|---|---|---|
| 3-1 | $SO_2CH_3$ | CF | N-methyl tetrazolyl | H | H | H | H | H | |
| 3-2 | $SO_2CH_3$ | CF | N-methyl tetrazolyl | Cl | H | Cl | H | H | |
| 3-3 | $SO_2CH_3$ | CF | N-methyl tetrazolyl | H | H | $OCH_3$ | H | H | |
| 3-4 | $SO_2CH_3$ | CF | N-methyl tetrazolyl | H | H | $NO_2$ | H | H | |
| 3-5 | $SO_2CH_3$ | $CF_3$ | N-methyl tetrazolyl | H | H | $CF_3$ | H | H | |
| 3-6 | $SO_2CH_3$ | $CF_3$ | N-methyl tetrazolyl | H | $OCF_3$ | H | H | H | |
| 3-7 | $SO_2CH_3$ | $CF_3$ | N-methyl tetrazolyl | H | H | phenyl | H | H | |

TABLE 3-continued

Structures and Physical Properties of Part of Compounds of Formula 1

| Compound | $X_1$ | $X_3$ | Q | $R_1$ | $R_2$ | $R_3$ | $R_4$ | $R_5$ | Appearance (Melting Point ° C.) |
|---|---|---|---|---|---|---|---|---|---|
| 3-8 | $SO_2CH_3$ | $CF_3$ | 1-methyl-tetrazol-5-yl | H | | -O-CH$_2$-O- (dioxolane) | H | H | |
| 3-9 | $SO_2CH_3$ | $CF_3$ | 1-methyl-tetrazol-5-yl | H | | -O-CH$_2$CH$_2$-O- (dioxane) | H | H | |
| 3-10 | $SO_2CH_3$ | $CF_3$ | 1-methyl-tetrazol-5-yl | H | | -CH=CH-CH=CH- | H | H | |
| 3-11 | $SO_2CH_3$ | $CF_3$ | 1-methyl-tetrazol-5-yl | H | -CH=CH-CH=CH- | H | H | H | |
| 3-12 | $NO_2$ | $SO_2CH_3$ | 1-methyl-tetrazol-5-yl | H | H | H | H | H | |
| 3-13 | $NO_2$ | $SO_2CH_3$ | 1-methyl-tetrazol-5-yl | H | H | -O-CH$_2$-O- | H | H | |
| 3-14 | $NO_2$ | Cl | 1-methyl-tetrazol-5-yl | H | H | H | H | H | |
| 3-15 | Cl | Cl | 1-methyl-tetrazol-5-yl | H | H | H | H | H | |

TABLE 3-continued
Structures and Physical Properties of Part of Compounds of Formula 1
| Compound | $X_1$ | $X_3$ | Q | $R_1$ | $R_2$ | $R_3$ | $R_4$ | $R_5$ | Appearance (Melting Point ° C.) |
|---|---|---|---|---|---|---|---|---|---|
| 3-16 | Cl | Cl | 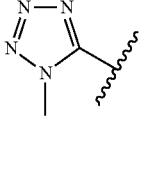 | H | | 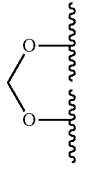 | H | H | |
| 3-17 | Cl | SO$_2$CH$_3$ | 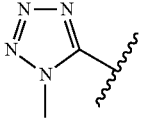 | H | H | H | H | H | |
| 3-18 | Cl | SO$_2$CH$_3$ | 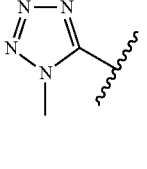 | H | | 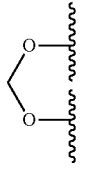 | H | H | |
| 3-19 | CH$_3$ | SO$_2$CH$_3$ | 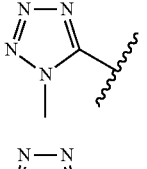 | H | H | H | H | H | |
| 3-20 | CN | SO$_2$CH$_3$ | 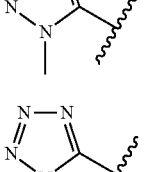 | H | H | H | H | H | |
| 3-21 | CF$_3$ | SO$_2$CH$_3$ | 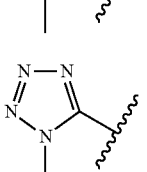 | H | H | H | H | H | |
| 3-22 | 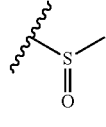 [SMILES: *S(C)=O] | SO$_2$CH$_3$ | 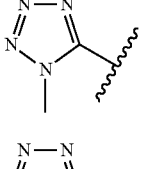 | H | H | H | H | H | |
| 3-23 | 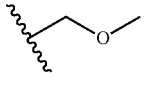 [SMILES: *COC] | SO$_2$CH$_3$ | 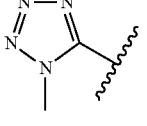 | H | H | H | H | H | |
| 3-24 | 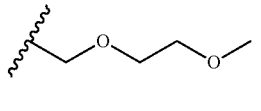 [SMILES: *COCCOC] | SO$_2$CH$_3$ | 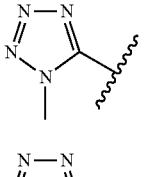 | H | H | H | H | H | |
| 3-25 | 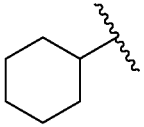 [SMILES: *C1CCCCC1] | SO$_2$CH$_3$ | 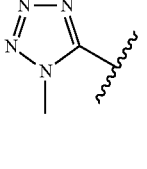 | H | H | H | H | H | |

TABLE 3-continued

Structures and Physical Properties of Part of Compounds of Formula 1

| Compound | $X_1$ | $X_3$ | Q | $R_1$ | $R_2$ | $R_3$ | $R_4$ | $R_5$ | Appearance (Melting Point ° C.) |
|---|---|---|---|---|---|---|---|---|---|
| 3-26 | cyclohexylmethyl | $SO_2CH_3$ | 1-methyltetrazol-5-yl | H | H | H | H | H | |
| 3-27 | vinyl | $SO_2CH_3$ | 1-methyltetrazol-5-yl | H | H | H | H | H | |
| 3-28 | ethynyl | $SO_2CH_3$ | 1-methyltetrazol-5-yl | H | H | H | H | H | |
| 3-29 | $SO_2CH{=}CH_2$ | $SO_2CH_3$ | 1-methyltetrazol-5-yl | H | H | H | H | H | |
| 3-30 | ethynylsulfonyl | $SO_2CH_3$ | 1-methyltetrazol-5-yl | H | H | H | H | H | |
| 3-31 | phenyl | $SO_2CH_3$ | 1-methyltetrazol-5-yl | H | H | H | H | H | |
| 3-32 | phenylsulfonyl | $SO_2CH_3$ | 1-methyltetrazol-5-yl | H | H | H | H | H | |
| 3-33 | 4,5-dihydroisoxazol-3-yl | $SO_2CH_3$ | 1-methyltetrazol-5-yl | H | H | H | H | H | |
| 3-34 | 3,5-dimethylpyrazol-1-yl | $SO_2CH_3$ | 1-methyltetrazol-5-yl | H | H | H | H | H | |
| 3-35 | isoxazolidin-2-ylmethyl | $SO_2CH_3$ | 1-methyltetrazol-5-yl | H | H | H | H | H | |

TABLE 3-continued

Structures and Physical Properties of Part of Compounds of Formula 1

| Compound | $X_1$ | $X_3$ | Q | $R_1$ | $R_2$ | $R_3$ | $R_4$ | $R_5$ | Appearance (Melting Point ° C.) |
|---|---|---|---|---|---|---|---|---|---|
| 3-36 | 2,5-dimethylpyrazol-1-ylmethyl | $SO_2CH_3$ | 1-methyltetrazol-5-yl | H | H | H | H | H | |
| 3-37 | $SO_2CH_3$ | $CF_3$ | 5-methyl-1,3,4-oxadiazol-2-yl | H | H | H | H | H | |
| 3-38 | $SO_2CH_3$ | $CF_3$ | 5-methyl-1,3,4-oxadiazol-2-yl | Cl | H | Cl | H | H | |
| 3-39 | $SO_2CH_3$ | $CF_3$ | 5-methyl-1,3,4-oxadiazol-2-yl | H | H | $OCH_3$ | H | H | |
| 3-40 | $SO_2CH_3$ | $CF_3$ | 5-methyl-1,3,4-oxadiazol-2-yl | H | H | $NO_2$ | H | H | |
| 3-41 | $SO_2CH_3$ | $CF_3$ | 5-methyl-1,3,4-oxadiazol-2-yl | H | H | $CF_3$ | H | H | |
| 3-42 | $SO_2CH_3$ | $CF_3$ | 5-methyl-1,3,4-oxadiazol-2-yl | H | $OCF_3$ | H | H | H | |
| 3-43 | $SO_2CH_3$ | $CF_3$ | 5-methyl-1,3,4-oxadiazol-2-yl | H | H | phenyl | H | H | |
| 3-44 | $SO_2CH_3$ | $CF_3$ | 5-methyl-1,3,4-oxadiazol-2-yl | H | 1,3-dioxolan-2-yl (R2,R3 fused) | | H | H | |
| 3-45 | $SO_2CH_3$ | $CF_3$ | 5-methyl-1,3,4-oxadiazol-2-yl | H | 1,3-dioxan-2-yl (R2,R3 fused) | | H | H | |

TABLE 3-continued
Structures and Physical Properties of Part of Compounds of Formula 1
| Compound | $X_1$ | $X_3$ | Q | $R_1$ | $R_2$ | $R_3$ | $R_4$ | $R_5$ | Appearance (Melting Point ° C.) |
|---|---|---|---|---|---|---|---|---|---|
| 3-46 | $SO_2CH_3$ | $CF_3$ | 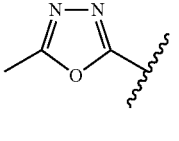 [SMILES: *c1nnc(C)o1] | H | | 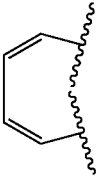 [SMILES: */C=C\C=C/*] | H | H | |
| 3-47 | $SO_2CH_3$ | $CF_3$ | 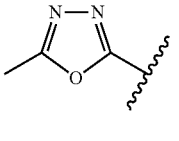 [SMILES: *c1nnc(C)o1] | | H | 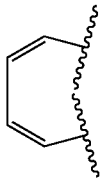 [SMILES: */C=C\C=C/*] | H | H | |
| 3-48 | $NO_2$ | $SO_2CH_3$ | 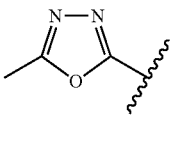 [SMILES: *c1nnc(C)o1] | H | H | H | H | H | |
| 3-49 | $NO_2$ | $SO_2CH_3$ | 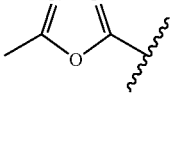 | H | 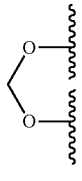 | | H | H | |
| 3-50 | $NO_2$ | Cl | 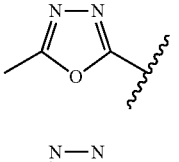 | H | H | H | H | H | |
| 3-51 | Cl | Cl | 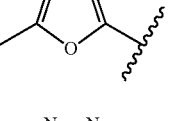 | H | H | H | H | H | |
| 3-52 | Cl | Cl | 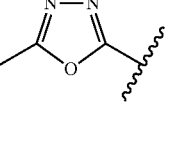 | H | 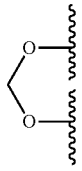 [SMILES: *OCO*] | | H | H | |
| 3-53 | Cl | $SO_2CH_3$ | 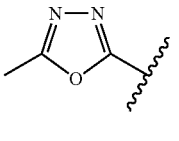 [SMILES: *c1nnc(C)o1] | H | H | H | H | H | |
| 3-54 | Cl | $SO_2CH_3$ | 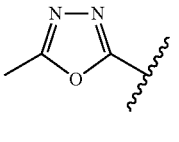 [SMILES: *c1nnc(C)o1] | H | 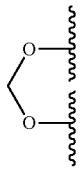 | | H | H | |

TABLE 3-continued

Structures and Physical Properties of Part of Compounds of Formula 1

| Compound | $X_1$ | $X_3$ | Q | $R_1$ | $R_2$ | $R_3$ | $R_4$ | $R_5$ | Appearance (Melting Point ° C.) |
|---|---|---|---|---|---|---|---|---|---|
| 3-55 | $CH_3$ | $SO_2CH_3$ | methyl-oxadiazole | H | H | H | H | H | |
| 3-56 | CN | $SO_2CH_3$ | methyl-oxadiazole | H | H | H | H | H | |
| 3-57 | $CF_3$ | $SO_2CH_3$ | methyl-oxadiazole | H | H | H | H | H | |
| 3-58 | S(=O)CH₃ | $SO_2CH_3$ | methyl-oxadiazole | H | H | H | H | H | |
| 3-59 | CH₂OCH₃ | $SO_2CH_3$ | methyl-oxadiazole | H | H | H | H | H | |
| 3-60 | CH₂OCH₂CH₂OCH₃ | $SO_2CH_3$ | methyl-oxadiazole | H | H | H | H | H | |
| 3-61 | cyclohexyl | $SO_2CH_3$ | methyl-oxadiazole | H | H | H | H | H | |
| 3-62 | cyclohexylmethyl | $SO_2CH_3$ | methyl-oxadiazole | H | H | H | H | H | |
| 3-63 | CH₂CH=CH₂ | $SO_2CH_3$ | methyl-oxadiazole | H | H | H | H | H | |
| 3-64 | CH₂C≡CH | $SO_2CH_3$ | methyl-oxadiazole | H | H | H | H | H | |
| 3-65 | $SO_2CH=CH_2$ | $SO_2CH_3$ | methyl-oxadiazole | H | H | H | H | H | |

TABLE 3-continued

Structures and Physical Properties of Part of Compounds of Formula 1

| Compound | $X_1$ | $X_3$ | Q | $R_1$ | $R_2$ | $R_3$ | $R_4$ | $R_5$ | Appearance (Melting Point ° C.) |
|---|---|---|---|---|---|---|---|---|---|
| 3-66 | ethynylsulfonyl | $SO_2CH_3$ | methyl-1,3,4-oxadiazolyl | H | H | H | H | H | |
| 3-67 | phenyl | $SO_2CH_3$ | methyl-1,3,4-oxadiazolyl | H | H | H | H | H | |
| 3-68 | phenylsulfonyl | $SO_2CH_3$ | methyl-1,3,4-oxadiazolyl | H | H | H | H | H | |
| 3-69 | 4,5-dihydroisoxazol-3-yl | $SO_2CH_3$ | methyl-1,3,4-oxadiazolyl | H | H | H | H | H | |
| 3-70 | 3,5-dimethylpyrazol-1-yl | $SO_2CH_3$ | methyl-1,3,4-oxadiazolyl | H | H | H | H | H | |
| 3-71 | isoxazolidin-2-ylmethyl | $SO_2CH_3$ | methyl-1,3,4-oxadiazolyl | H | H | H | H | H | |
| 3-72 | (3,5-dimethylpyrazol-1-yl)methyl | $SO_2CH_3$ | methyl-1,3,4-oxadiazolyl | H | H | H | H | H | |
| 3-73 | $SO_2CH_3$ | $CF_3$ | methyl-1,3,4-thiadiazolyl | H | H | H | H | H | |
| 3-74 | $SO_2CH_3$ | $CF_3$ | methyl-1,3,4-thiadiazolyl | Cl | H | Cl | H | H | |
| 3-75 | $SO_2CH_3$ | $CF_3$ | methyl-1,3,4-thiadiazolyl | H | H | $OCH_3$ | H | H | |
| 3-76 | $SO_2CH_3$ | $CF_3$ | methyl-1,3,4-thiadiazolyl | H | H | $NO_2$ | H | H | |

TABLE 3-continued

Structures and Physical Properties of Part of Compounds of Formula 1

| Compound | $X_1$ | $X_3$ | Q | $R_1$ | $R_2$ | $R_3$ | $R_4$ | $R_5$ | Appearance (Melting Point ° C.) |
|---|---|---|---|---|---|---|---|---|---|
| 3-77 | $SO_2CH_3$ | $CF_3$ | 2-methyl-1,3,4-thiadiazol-5-yl | H | H | $CF_3$ | H | H | |
| 3-78 | $SO_2CH_3$ | $CF_3$ | 2-methyl-1,3,4-thiadiazol-5-yl | H | $OCF_3$ | H | H | H | |
| 3-79 | $SO_2CH_3$ | $CF_3$ | 2-methyl-1,3,4-thiadiazol-5-yl | H | H | phenyl | H | H | |
| 3-80 | $SO_2CH_3$ | $CF_3$ | 2-methyl-1,3,4-thiadiazol-5-yl | H | H | -OCH$_2$O- | H | H | |
| 3-81 | $SO_2CH_3$ | $CF_3$ | 2-methyl-1,3,4-thiadiazol-5-yl | H | H | -OCH$_2$CH$_2$O- | H | H | |
| 3-82 | $SO_2CH_3$ | $CF_3$ | 2-methyl-1,3,4-thiadiazol-5-yl | H | H | -CH=CH-CH=CH- | H | H | |
| 3-83 | $SO_2CH_3$ | $CF_3$ | 2-methyl-1,3,4-thiadiazol-5-yl | H | -CH=CH-CH=CH- | H | H | H | |
| 3-84 | $NO_2$ | $SO_2CH_3$ | 2-methyl-1,3,4-thiadiazol-5-yl | H | H | H | H | H | |
| 3-85 | $NO_2$ | $SO_2CH_3$ | 2-methyl-1,3,4-thiadiazol-5-yl | H | H | -OCH$_2$O- | H | H | |

TABLE 3-continued

Structures and Physical Properties of Part of Compounds of Formula 1

| Compound | $X_1$ | $X_3$ | Q | $R_1$ | $R_2$ | $R_3$ | $R_4$ | $R_5$ | Appearance (Melting Point ° C.) |
|---|---|---|---|---|---|---|---|---|---|
| 3-86 | $NO_2$ | Cl | 5-methyl-1,3,4-thiadiazol-2-yl | H | H | H | H | H | |
| 3-87 | Cl | Cl | 5-methyl-1,3,4-thiadiazol-2-yl | H | H | H | H | H | |
| 3-88 | Cl | Cl | 5-methyl-1,3,4-thiadiazol-2-yl | H | | -OCH$_2$O- | H | H | |
| 3-89 | Cl | $SO_2CH_3$ | 5-methyl-1,3,4-thiadiazol-2-yl | H | H | H | H | H | |
| 3-90 | Cl | $SO_2CH_3$ | 5-methyl-1,3,4-thiadiazol-2-yl | H | | -OCH$_2$O- | H | H | |
| 3-91 | $CH_3$ | $SO_2CH_3$ | 5-methyl-1,3,4-thiadiazol-2-yl | H | H | H | H | H | |
| 3-92 | CN | $SO_2CH_3$ | 5-methyl-1,3,4-thiadiazol-2-yl | H | H | H | H | H | |
| 3-93 | $CF_3$ | $SO_2CH_3$ | 5-methyl-1,3,4-thiadiazol-2-yl | H | H | H | H | H | |
| 3-94 | -S(=O)CH$_3$ | $SO_2CH_3$ | 5-methyl-1,3,4-thiadiazol-2-yl | H | H | H | H | H | |
| 3-95 | -CH$_2$OCH$_3$ | $SO_2CH_3$ | 5-methyl-1,3,4-thiadiazol-2-yl | H | H | H | H | H | |

TABLE 3-continued

Structures and Physical Properties of Part of Compounds of Formula 1

| Compound | $X_1$ | $X_3$ | Q | $R_1$ | $R_2$ | $R_3$ | $R_4$ | $R_5$ | Appearance (Melting Point ° C.) |
|---|---|---|---|---|---|---|---|---|---|
| 3-96 | -CH$_2$CH$_2$OCH$_2$CH$_2$OCH$_3$ | SO$_2$CH$_3$ | 5-methyl-1,3,4-thiadiazol-2-yl | H | H | H | H | H | |
| 3-97 | cyclohexyl | SO$_2$CH$_3$ | 5-methyl-1,3,4-thiadiazol-2-yl | H | H | H | H | H | |
| 3-98 | cyclohexylmethyl | SO$_2$CH$_3$ | 5-methyl-1,3,4-thiadiazol-2-yl | H | H | H | H | H | |
| 3-99 | allyl | SO$_2$CH$_3$ | 5-methyl-1,3,4-thiadiazol-2-yl | H | H | H | H | H | |
| 3-100 | propargyl | SO$_2$CH$_3$ | 5-methyl-1,3,4-thiadiazol-2-yl | H | H | H | H | H | |
| 3-101 | SO$_2$CH=CH$_2$ | SO$_2$CH$_3$ | 5-methyl-1,3,4-thiadiazol-2-yl | H | H | H | H | H | |
| 3-102 | -S(O)$_2$C≡CH | SO$_2$CH$_3$ | 5-methyl-1,3,4-thiadiazol-2-yl | H | H | H | H | H | |
| 3-103 | benzyl | SO$_2$CH$_3$ | 5-methyl-1,3,4-thiadiazol-2-yl | H | H | H | H | H | |
| 3-104 | -S(O)$_2$Ph | SO$_2$CH$_3$ | 5-methyl-1,3,4-thiadiazol-2-yl | H | H | H | H | H | |
| 3-105 | 4,5-dihydroisoxazol-3-yl | SO$_2$CH$_3$ | 5-methyl-1,3,4-thiadiazol-2-yl | H | H | H | H | H | |
| 3-106 | 3,5-dimethyl-1H-pyrazol-1-yl | SO$_2$CH$_3$ | 5-methyl-1,3,4-thiadiazol-2-yl | H | H | H | H | H | |

TABLE 3-continued

Structures and Physical Properties of Part of Compounds of Formula 1

| Compound | $X_1$ | $X_3$ | Q | $R_1$ | $R_2$ | $R_3$ | $R_4$ | $R_5$ | Appearance (Melting Point ° C.) |
|---|---|---|---|---|---|---|---|---|---|
| 3-107 | (isoxazolidinyl-methyl) | $SO_2CH_3$ | (methyl-thiadiazolyl) | H | H | H | H | H | |
| 3-108 | (dimethyl-pyrazolyl-methyl) | $SO_2CH_3$ | (methyl-thiadiazolyl) | H | H | H | H | H | |
| 3-109 | $SO_2CH_3$ | $CF_3$ | (N-methyl-tetrazolyl) | H | H | H | H | H | |
| 3-110 | $SO_2CH_3$ | $CF_3$ | (N-methyl-tetrazolyl) | H | H | H | H | H | |
| 3-111 | $SO_2CH_3$ | $CF_3$ | (N-methyl-tetrazolyl) | H | H | H | H | H | |
| 3-112 | $SO_2CH_3$ | $CF_3$ | (N-methyl-tetrazolyl) | H | H | H | H | H | |
| 3-113 | $SO_2CH_3$ | $CF_3$ | (N-methyl-tetrazolyl) | H | H | H | H | H | |
| 3-114 | $SO_2CH_3$ | $CF_3$ | (N-methyl-tetrazolyl) | H | $OCF_3$ | H | H | H | |
| 3-115 | $SO_2CH_3$ | $CF_3$ | (N-methyl-tetrazolyl) | H | H | (phenyl) | H | H | |
| 3-116 | $SO_2CH_3$ | $CF_3$ | (N-methyl-tetrazolyl) | H | (1,3-dioxolanyl) | | H | H | |

TABLE 3-continued
Structures and Physical Properties of Part of Compounds of Formula 1
| Compound | X$_1$ | X$_3$ | Q | R$_1$ | R$_2$ | R$_3$ | R$_4$ | R$_5$ | Appearance (Melting Point ° C.) |
|---|---|---|---|---|---|---|---|---|---|
| 3-117 | SO$_2$CH$_3$ | CF$_3$ | 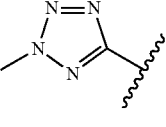 [SMILES: *c1nnn(C)n1] | H | 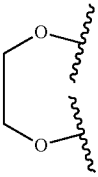 | | H | H | |
| 3-118 | SO$_2$CH$_3$ | CF$_3$ | 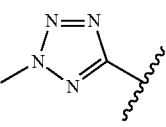 [SMILES: *c1nnn(C)n1] | H | 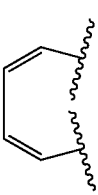 [SMILES: */C=C\C=C/*] | | H | H | |
| 3-119 | SO$_2$CH$_3$ | CF$_3$ | 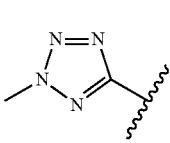 [SMILES: *c1nnn(C)n1] | | 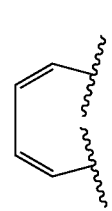 | H | H | H | |
| 3-120 | NO$_2$ | SO$_2$CH$_3$ | 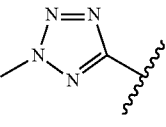 | H | H | H | H | H | |
| 3-121 | NO$_2$ | SO$_2$CH$_3$ | 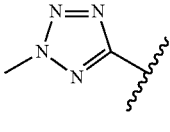 [SMILES: *c1nnn(C)n1] | H | 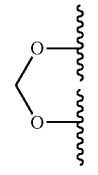 [SMILES: *OCO*] | | H | H | |
| 3-122 | NO$_2$ | Cl | 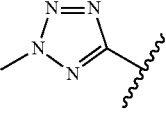 [SMILES: *c1nnn(C)n1] | H | H | H | H | H | |
| 3-123 | Cl | Cl | 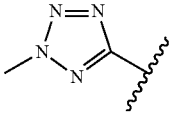 [SMILES: *c1nnn(C)n1] | H | H | H | H | H | |
| 3-124 | Cl | Cl | 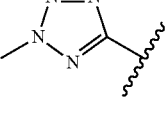 | H | 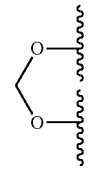 [SMILES: *OCO*] | | H | H | |
| 3-125 | Cl | SO$_2$CH$_3$ | 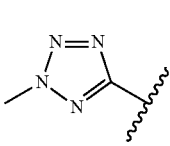 [SMILES: *c1nnn(C)n1] | H | H | H | H | H | |

TABLE 3-continued

Structures and Physical Properties of Part of Compounds of Formula 1

| Compound | X₁ | X₃ | Q | R₁ | R₂ | R₃ | R₄ | R₅ | Appearance (Melting Point ° C.) |
|---|---|---|---|---|---|---|---|---|---|
| 3-126 | Cl | SO₂CH₃ | 2-methyltetrazol-5-yl | H | | methylenedioxy | H | H | |
| 3-127 | CH₃ | SO₂CH₃ | 2-methyltetrazol-5-yl | H | H | H | H | H | |
| 3-128 | CN | SO₂CH₃ | 2-methyltetrazol-5-yl | H | H | H | H | H | |
| 3-129 | CF₃ | SO₂CH₃ | 2-methyltetrazol-5-yl | H | H | H | H | H | |
| 3-130 | S(=O)CH₃ | SO₂CH₃ | 2-methyltetrazol-5-yl | H | H | H | H | H | |
| 3-131 | CH₂OCH₃ | SO₂CH₃ | 2-methyltetrazol-5-yl | H | H | H | H | H | |
| 3-132 | CH₂OCH₂CH₂OCH₃ | SO₂CH₃ | 2-methyltetrazol-5-yl | H | H | H | H | H | |
| 3-133 | cyclohexyl | SO₂CH₃ | 2-methyltetrazol-5-yl | H | H | H | H | H | |
| 3-134 | cyclohexylmethyl | SO₂CH₃ | 2-methyltetrazol-5-yl | H | H | H | H | H | |
| 3-135 | allyl | SO₂CH₃ | 2-methyltetrazol-5-yl | H | H | H | H | H | |
| 3-136 | propargyl | SO₂CH₃ | 2-methyltetrazol-5-yl | H | H | H | H | H | |

TABLE 3-continued

Structures and Physical Properties of Part of Compounds of Formula 1

| Compound | X₁ | X₃ | Q | R₁ | R₂ | R₃ | R₄ | R₅ | Appearance (Melting Point ° C.) |
|---|---|---|---|---|---|---|---|---|---|
| 3-137 | SO₂CH=CH₂ | SO₂CH₃ | 2-methyl-2H-tetrazol-5-yl | H | H | H | H | H | |
| 3-138 | -S(O)₂-C≡CH | SO₂CH₃ | 2-methyl-2H-tetrazol-5-yl | H | H | H | H | H | |
| 3-139 | phenyl | SO₂CH₃ | 2-methyl-2H-tetrazol-5-yl | H | H | H | H | H | |
| 3-140 | -S(O)₂-phenyl | SO₂CH₃ | 2-methyl-2H-tetrazol-5-yl | H | H | H | H | H | |
| 3-141 | 4,5-dihydroisoxazol-3-yl | SO₂CH₃ | 2-methyl-2H-tetrazol-5-yl | H | H | H | H | H | |
| 3-142 | 3,5-dimethyl-1H-pyrazol-1-yl | SO₂CH₃ | 2-methyl-2H-tetrazol-5-yl | H | H | H | H | H | |
| 3-143 | (isoxazolidin-2-yl)methyl | SO₂CH₃ | 2-methyl-2H-tetrazol-5-yl | H | H | H | H | H | |
| 3-144 | (3,5-dimethyl-1H-pyrazol-1-yl)methyl | SO₂CH₃ | 2-methyl-2H-tetrazol-5-yl | H | H | H | H | H | |
| 3-145 | SO₂CH₃ | CF₃ | 1-methyl-1H-1,2,4-triazol-5-yl | H | H | H | H | H | |
| 3-146 | SO₂CH₃ | CF₃ | 1-methyl-1H-1,2,4-triazol-5-yl | Cl | H | Cl | H | H | |
| 3-147 | SO₂CH₃ | CF₃ | 1-methyl-1H-1,2,4-triazol-5-yl | H | H | OCH₃ | H | H | |

TABLE 3-continued
Structures and Physical Properties of Part of Compounds of Formula 1
| Compound | $X_1$ | $X_3$ | Q | $R_1$ | $R_2$ | $R_3$ | $R_4$ | $R_5$ | Appearance (Melting Point ° C.) |
|---|---|---|---|---|---|---|---|---|---|
| 3-148 | $SO_2CH_3$ | $CF_3$ | 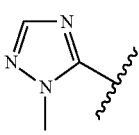 | H | H | $NO_2$ | H | H | |
| 3-149 | $SO_2CH_3$ | $CF_3$ | 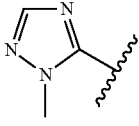 | H | H | $CF_3$ | H | H | |
| 3-150 | $SO_2CH_3$ | $CF_3$ | 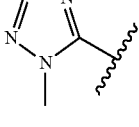 | H | $OCF_3$ | H | H | H | |
| 3-151 | $SO_2CH_3$ | $CF_3$ | 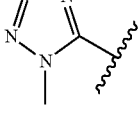 | H | H | 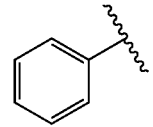 | H | H | |
| 3-152 | $SO_2CH_3$ | $CF_3$ | 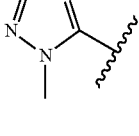 | H | 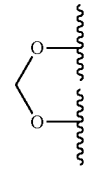 [SMILES: *OCO*] | | H | H | |
| 3-153 | $SO_2CH_3$ | $CF_3$ | 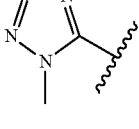 | H | 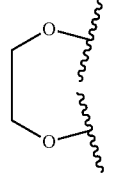 [SMILES: *OCCO*] | | H | H | |
| 3-154 | $SO_2CH_3$ | $CF_3$ | 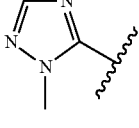 | H | 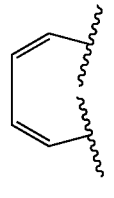 [SMILES: */C=C\C=C/*] | | H | H | |
| 3-155 | $SO_2CH_3$ | $CF_3$ | 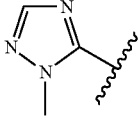 | | 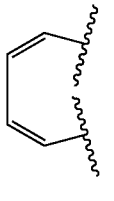 [SMILES: */C=C\C=C/*] | H | H | H | |
| 3-156 | $NO_2$ | $SO_2CH_3$ | 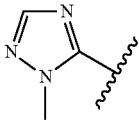 | H | H | H | H | H | |

TABLE 3-continued

Structures and Physical Properties of Part of Compounds of Formula 1

| Compound | X₁ | X₃ | Q | R₁ | R₂ | R₃ | R₄ | R₅ | Appearance (Melting Point ° C.) |
|---|---|---|---|---|---|---|---|---|---|
| 3-157 | NO₂ | SO₂CH₃ | 1-methyl-1,2,4-triazol-5-yl | H | methylenedioxy | H | H | H | |
| 3-158 | NO₂ | Cl | 1-methyl-1,2,4-triazol-5-yl | H | H | H | H | H | |
| 3-159 | Cl | Cl | 1-methyl-1,2,4-triazol-5-yl | H | H | H | H | H | |
| 3-160 | Cl | Cl | 1-methyl-1,2,4-triazol-5-yl | H | methylenedioxy | H | H | H | |
| 3-161 | Cl | SO₂CH₃ | 1-methyl-1,2,4-triazol-5-yl | H | H | H | H | H | |
| 3-162 | Cl | SO₂CH₃ | 1-methyl-1,2,4-triazol-5-yl | H | methylenedioxy | H | H | H | |
| 3-163 | CH₃ | SO₂CH₃ | 1-methyl-1,2,4-triazol-5-yl | H | H | H | H | H | |
| 3-164 | CN | SO₂CH₃ | 1-methyl-1,2,4-triazol-5-yl | H | H | H | H | H | |
| 3-165 | CF₃ | SO₂CH₃ | 1-methyl-1,2,4-triazol-5-yl | H | H | H | H | H | |
| 3-166 | S(O)CH₃ | SO₂CH₃ | 1-methyl-1,2,4-triazol-5-yl | H | H | H | H | H | |

TABLE 3-continued

Structures and Physical Properties of Part of Compounds of Formula 1

| Compound | $X_1$ | $X_3$ | Q | $R_1$ | $R_2$ | $R_3$ | $R_4$ | $R_5$ | Appearance (Melting Point ° C.) |
|---|---|---|---|---|---|---|---|---|---|
| 3-167 | -CH$_2$-O-CH$_3$ | SO$_2$CH$_3$ | N-methyl-triazolyl | H | H | H | H | H | |
| 3-168 | -CH$_2$-O-CH$_2$-CH$_2$-O-CH$_3$ | SO$_2$CH$_3$ | N-methyl-triazolyl | H | H | H | H | H | |
| 3-169 | cyclohexyl | SO$_2$CH$_3$ | N-methyl-triazolyl | H | H | H | H | H | |
| 3-170 | cyclohexyl-CH$_2$- | SO$_2$CH$_3$ | N-methyl-triazolyl | H | H | H | H | H | |
| 3-171 | -CH$_2$-CH=CH$_2$ | SO$_2$CH$_3$ | N-methyl-triazolyl | H | H | H | H | H | |
| 3-172 | -CH$_2$-C≡CH | SO$_2$CH$_3$ | N-methyl-triazolyl | H | H | H | H | H | |
| 3-173 | SO$_2$CH=CH$_2$ | SO$_2$CH$_3$ | N-methyl-triazolyl | H | H | H | H | H | |
| 3-174 | -SO$_2$-C≡CH | SO$_2$CH$_3$ | N-methyl-triazolyl | H | H | H | H | H | |
| 3-175 | phenyl | SO$_2$CH$_3$ | N-methyl-triazolyl | H | H | H | H | H | |
| 3-176 | -SO$_2$-phenyl | SO$_2$CH$_3$ | N-methyl-triazolyl | H | H | H | H | H | |

TABLE 3-continued

Structures and Physical Properties of Part of Compounds of Formula 1

| Compound | X₁ | X₃ | Q | R₁ | R₂ | R₃ | R₄ | R₅ | Appearance (Melting Point ° C.) |
|---|---|---|---|---|---|---|---|---|---|
| 3-177 | (4,5-dihydroisoxazol-3-yl) | SO₂CH₃ | (1-methyl-1,2,4-triazol-5-yl) | H | H | H | H | H | |
| 3-178 | (1,5-dimethyl-1H-pyrazol-3-yl) | SO₂CH₃ | (1-methyl-1,2,4-triazol-5-yl) | H | H | H | H | H | |
| 3-179 | (isoxazolidin-2-yl-methyl) | SO₂CH₃ | (1-methyl-1,2,4-triazol-5-yl) | H | H | H | H | H | |
| 3-180 | ((3,5-dimethyl-1H-pyrazol-1-yl)methyl) | SO₂CH₃ | (1-methyl-1,2,4-triazol-5-yl) | H | H | H | H | H | |
| 3-181 | SO₂CH₃ | CF₃ | (4-methyl-1,2,5-oxadiazol-3-yl) | H | H | H | H | H | |
| 3-182 | SO₂CH₃ | CF₃ | (4-methyl-1,2,5-oxadiazol-3-yl) | Cl | H | Cl | H | H | |
| 3-183 | SO₂CH₃ | CF₃ | (4-methyl-1,2,5-oxadiazol-3-yl) | H | H | OCH₃ | H | H | |
| 3-184 | SO₂CH₃ | CF₃ | (4-methyl-1,2,5-oxadiazol-3-yl) | H | H | NO₂ | H | H | |
| 3-185 | SO₂CH₃ | CF₃ | (4-methyl-1,2,5-oxadiazol-3-yl) | H | H | CF₃ | H | H | |
| 3-186 | SO₂CH₃ | CF₃ | (4-methyl-1,2,5-oxadiazol-3-yl) | H | OCF₃ | H | H | H | |
| 3-187 | SO₂CH₃ | CF₃ | (4-methyl-1,2,5-oxadiazol-3-yl) | H | H | phenyl | H | H | |

TABLE 3-continued

Structures and Physical Properties of Part of Compounds of Formula 1

| Compound | X₁ | X₃ | Q | R₁ | R₂ | R₃ | R₄ | R₅ | Appearance (Melting Point ° C.) |
|---|---|---|---|---|---|---|---|---|---|
| 3-188 | SO₂CH₃ | CF₃ | oxadiazole | H | | -OCH₂O- | H | H | |
| 3-189 | SO₂CH₃ | CF₃ | oxadiazole | H | | -OCH₂CH₂O- | H | H | |
| 3-190 | SO₂CH₃ | CF₃ | oxadiazole | H | | -CH=CH-CH=CH- | H | H | |
| 3-191 | SO₂CH₃ | CF₃ | oxadiazole | H | -CH=CH-CH=CH- | H | H | H | |
| 3-192 | NO₂ | SO₂CH₃ | oxadiazole | H | H | H | H | H | |
| 3-193 | NO₂ | SO₂CH₃ | oxadiazole | H | | -OCH₂O- | H | H | |
| 3-194 | NO₂ | Cl | oxadiazole | H | H | H | H | H | |
| 3-195 | Cl | Cl | oxadiazole | H | H | H | H | H | |

TABLE 3-continued
Structures and Physical Properties of Part of Compounds of Formula 1
| Compound | $X_1$ | $X_3$ | Q | $R_1$ | $R_2$ | $R_3$ | $R_4$ | $R_5$ | Appearance (Melting Point ° C.) |
|---|---|---|---|---|---|---|---|---|---|
| 3-196 | Cl | Cl | 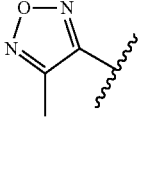 | H | | 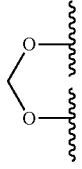 [SMILES: *OCO*] | H | H | |
| 3-197 | Cl | SO$_2$CH$_3$ | 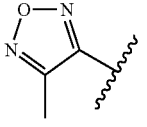 | H | H | H | H | H | |
| 3-198 | Cl | SO$_2$CH$_3$ | 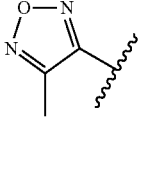 | H | H | 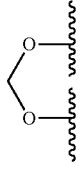 | H | H | |
| 3-199 | CH$_3$ | SO$_2$CH$_3$ | 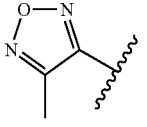 | H | H | H | H | H | |
| 3-200 | CN | SO$_2$CH$_3$ | 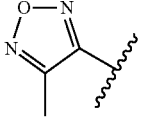 | H | H | H | H | H | |
| 3-201 | CF$_3$ | SO$_2$CH$_3$ | 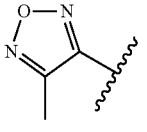 | H | H | H | H | H | |
| 3-202 | 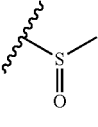 [SMILES: *S(C)=O] | SO$_2$CH$_3$ | 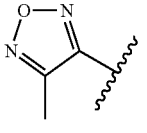 | H | H | H | H | H | |
| 3-203 | 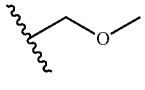 | SO$_2$CH$_3$ | 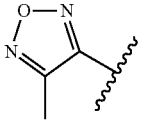 | H | H | H | H | H | |
| 3-204 | 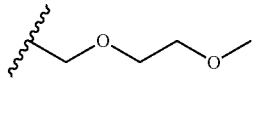 [SMILES: *COCCOC] | SO$_2$CH$_3$ | 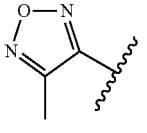 | H | H | H | H | H | |
| 3-205 | 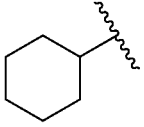 [SMILES: *C1CCCCC1] | SO$_2$CH$_3$ | 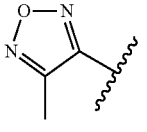 | H | H | H | H | H | |

TABLE 3-continued

Structures and Physical Properties of Part of Compounds of Formula 1

| Compound | $X_1$ | $X_3$ | Q | $R_1$ | $R_2$ | $R_3$ | $R_4$ | $R_5$ | Appearance (Melting Point ° C.) |
|---|---|---|---|---|---|---|---|---|---|
| 3-206 | cyclohexylmethyl | $SO_2CH_3$ | methyl-furazanyl | H | H | H | H | H | |
| 3-207 | vinyl | $SO_2CH_3$ | methyl-furazanyl | H | H | H | H | H | |
| 3-208 | ethynyl | $SO_2CH_3$ | methyl-furazanyl | H | H | H | H | H | |
| 3-209 | $SO_2CH=CH_2$ | $SO_2CH_3$ | methyl-furazanyl | H | H | H | H | H | |
| 3-210 | ethynylsulfonyl | $SO_2CH_3$ | methyl-furazanyl | H | H | H | H | H | |
| 3-211 | benzyl | $SO_2CH_3$ | methyl-furazanyl | H | H | H | H | H | |
| 3-212 | phenylsulfonyl | $SO_2CH_3$ | methyl-furazanyl | H | H | H | H | H | |
| 3-213 | 4,5-dihydroisoxazol-3-yl | $SO_2CH_3$ | methyl-furazanyl | H | H | H | H | H | |
| 3-214 | 3,5-dimethylpyrazol-1-yl | $SO_2CH_3$ | methyl-furazanyl | H | H | H | H | H | |
| 3-215 | isoxazolidin-2-ylmethyl | $SO_2CH_3$ | methyl-furazanyl | H | H | H | H | H | |

TABLE 3-continued

Structures and Physical Properties of Part of Compounds of Formula 1

| Compound | $X_1$ | $X_3$ | Q | $R_1$ | $R_2$ | $R_3$ | $R_4$ | $R_5$ | Appearance (Melting Point ° C.) |
|---|---|---|---|---|---|---|---|---|---|
| 3-216 | 3,5-dimethylpyrazol-1-ylmethyl | $SO_2CH_3$ | 3-methyl-1,2,4-oxadiazol-5-yl | H | H | H | H | H | |
| 3-217 | Cl | $CF_3$ | 1-methyltetrazol-5-yl | H | H | H | H | H | white solid (158-164) |
| 3-218 | H | Cl | 1-methyltetrazol-5-yl | H | H | H | H | H | white solid (171-175) |
| 3-219 | Cl | $CH_3$ | 1-methyltetrazol-5-yl | H | H | H | H | H | white solid (124-130) |
| 3-220 | H | H | 1-methyltetrazol-5-yl | H | H | H | H | H | white solid (110-116) |

In the compound of the formula I, W is N.

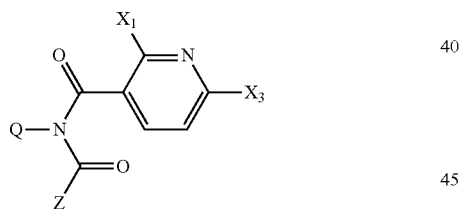

TABLE 4

Structures and Physical Properties of Part of Compounds of Formula 1

| Compound | $X_1$ | $X_3$ | Q | Z | Appearance (Melting Point °C.) |
|---|---|---|---|---|---|
| 4-1 | $SO_2CH_3$ | $CF_3$ | 1-methyltetrazol-5-yl | cyclohex-1-en-1-yl | |
| 4-2 | $SO_2CH_3$ | $CF_3$ | 1-methyltetrazol-5-yl | cyclohex-3-en-1-yl | |

TABLE 4-continued
Structures and Physical Properties of Part of Compounds of Formula 1
| Compound | $X_1$ | $X_3$ | Q | Z | Appearance (Melting Point °C.) |
|---|---|---|---|---|---|
| 4-3 | $SO_2CH_3$ | $CF_3$ | 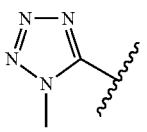 [SMILES: *c1nnnn1C] | 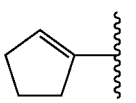 [SMILES: *C1=CCCC1] | |
| 4-4 | $SO_2CH_3$ | $CF_3$ | 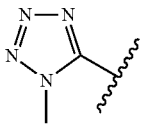 [SMILES: *c1nnnn1C] | 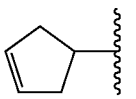 | |
| 4-5 | $SO_2CH_3$ | $CF_3$ | 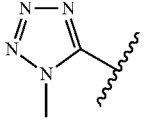 [SMILES: *c1nnnn1C] | 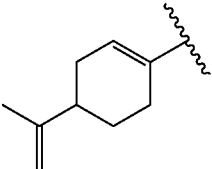 [SMILES: *C1=CCC(C(=C)C)CC1] | |
| 4-6 | $SO_2CH_3$ | $CF_3$ | 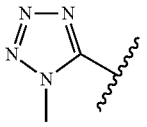 | 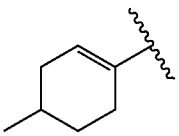 [SMILES: *C1=CCC(C)CC1] | |
| 4-7 | $SO_2CH_3$ | $CF_3$ | 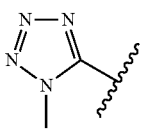 [SMILES: *c1nnnn1C] | 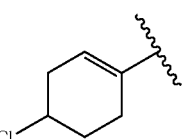 | |
| 4-8 | $SO_2CH_3$ | $CF_3$ | 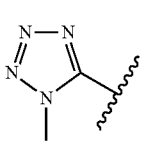 [SMILES: *c1nnnn1C] | 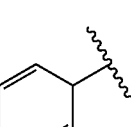 | |
| 4-9 | $SO_2CH_3$ | $CF_3$ | 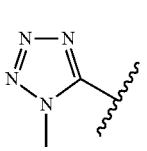 [SMILES: *c1nnnn1C] | 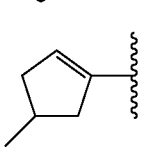 | |
| 4-10 | $SO_2CH_3$ | $CF_3$ | 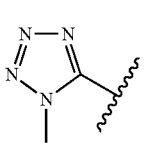 [SMILES: *c1nnnn1C] | 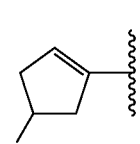 | |
| 4-11 | $SO_2CH_3$ | $CF_3$ | 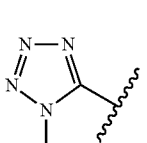 | 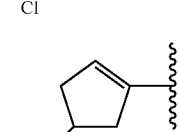 | |
| 4-12 | $NO_2$ | $SO_2CH_3$ | 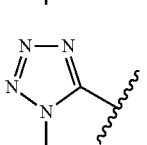 | 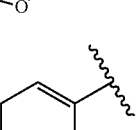 | |

TABLE 4-continued
Structures and Physical Properties of Part of Compounds of Formula 1
| Compound | X₁ | X₃ | Q | Z | Appearance (Melting Point °C.) |
|---|---|---|---|---|---|
| 4-13 | NO₂ | SO₂CH₃ | 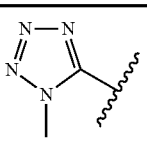 | 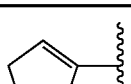 | |
| 4-14 | NO₂ | Cl | 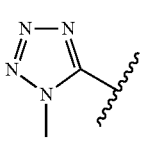 [SMILES: *c1nnnn1C] | 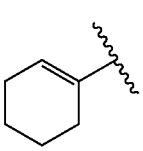 [SMILES: *C1=CCCCC1] | |
| 4-15 | Cl | Cl | 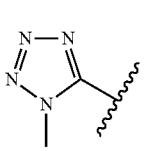 | 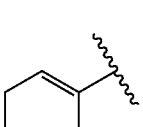 | |
| 4-16 | Cl | Cl | 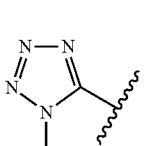 | 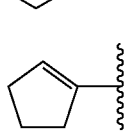 | |
| 4-17 | Cl | SO₂CH₃ | 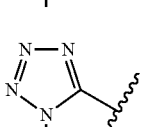 | 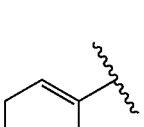 | |
| 4-18 | Cl | SO₂CH₃ | 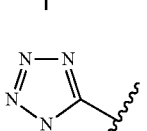 | 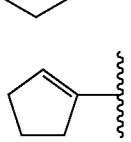 | |
| 4-19 | CH₃ | SO₂CH₃ | 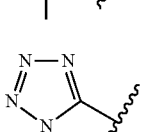 | 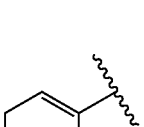 | |
| 4-20 | CN | SO₂CH₃ | 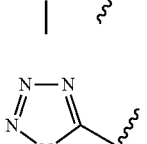 | 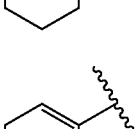 | |
| 4-21 | CF₃ | SO₂CH₃ | 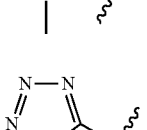 | 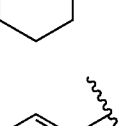 | |
| 4-22 | 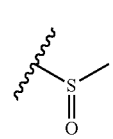 | SO₂CH₃ | 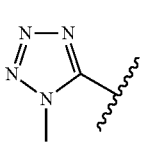 [SMILES: *c1nnnn1C] | 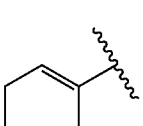 | |

TABLE 4-continued

Structures and Physical Properties of Part of Compounds of Formula 1

| Compound | X₁ | X₃ | Q | Z | Appearance (Melting Point °C.) |
|---|---|---|---|---|---|
| 4-23 | -CH₂-O-CH₃ | SO₂CH₃ | 1-methyl-tetrazol-5-yl | cyclohexenyl | |
| 4-24 | -CH₂-O-CH₂-CH₂-O-CH₃ | SO₂CH₃ | 1-methyl-tetrazol-5-yl | cyclohexenyl | |
| 4-25 | cyclohexyl | SO₂CH₃ | 1-methyl-tetrazol-5-yl | cyclohexenyl | |
| 4-26 | cyclohexyl-CH₂- | SO₂CH₃ | 1-methyl-tetrazol-5-yl | cyclohexenyl | |
| 4-27 | -CH₂-CH=CH₂ | SO₂CH₃ | 1-methyl-tetrazol-5-yl | cyclohexenyl | |
| 4-28 | -CH₂-C≡CH | SO₂CH₃ | 1-methyl-tetrazol-5-yl | cyclohexenyl | |
| 4-29 | SO₂CH₃=CH₂ | SO₂CH₃ | 1-methyl-tetrazol-5-yl | cyclohexenyl | |
| 4-30 | -CH(SO₂-C≡CH)- | SO₂CH₃ | 1-methyl-tetrazol-5-yl | cyclohexenyl | |
| 4-31 | phenyl-CH₂- | SO₂CH₃ | 1-methyl-tetrazol-5-yl | cyclohexenyl | |
| 4-32 | -CH₂-SO₂-phenyl | SO₂CH₃ | 1-methyl-tetrazol-5-yl | cyclohexenyl | |

TABLE 4-continued

Structures and Physical Properties of Part of Compounds of Formula 1

| Compound | X$_1$ | X$_3$ | Q | Z | Appearance (Melting Point °C.) |
|---|---|---|---|---|---|
| 4-33 | (4,5-dihydroisoxazol-3-yl) | SO$_2$CH$_3$ | (1-methyltetrazol-5-yl) | (cyclohex-1-en-1-yl) | |
| 4-34 | (3,5-dimethylpyrazol-1-yl-methyl) | SO$_2$CH$_3$ | (1-methyltetrazol-5-yl) | (cyclohex-1-en-1-yl) | |
| 4-35 | (isoxazolidin-2-yl-methyl) | SO$_2$CH$_3$ | (1-methyltetrazol-5-yl) | (cyclohex-1-en-1-yl) | |
| 4-36 | (3,5-dimethylpyrazol-1-yl-methyl) | SO$_2$CH$_3$ | (1-methyltetrazol-5-yl) | (cyclohex-1-en-1-yl) | |
| 4-37 | SO$_2$CH$_3$ | CF$_3$ | (5-methyl-1,3,4-oxadiazol-2-yl) | (cyclohex-1-en-1-yl) | |
| 4-38 | SO$_2$CH$_3$ | CF$_3$ | (5-methyl-1,3,4-oxadiazol-2-yl) | (cyclohex-3-en-1-yl) | |
| 4-39 | SO$_2$CH$_3$ | CF$_3$ | (5-methyl-1,3,4-oxadiazol-2-yl) | (cyclopent-1-en-1-yl) | |
| 4-40 | SO$_2$CH$_3$ | CF$_3$ | (5-methyl-1,3,4-oxadiazol-2-yl) | (cyclopent-3-en-1-yl) | |
| 4-41 | SO$_2$CH$_3$ | CF$_3$ | (5-methyl-1,3,4-oxadiazol-2-yl) | (4-(prop-1-en-2-yl)cyclohex-1-en-1-yl) | |
| 4-42 | SO$_2$CH$_3$ | CF$_3$ | (5-methyl-1,3,4-oxadiazol-2-yl) | (4-methylcyclohex-1-en-1-yl) | |

TABLE 4-continued

Structures and Physical Properties of Part of Compounds of Formula 1

| Compound | $X_1$ | $X_3$ | Q | Z | Appearance (Melting Point °C.) |
|---|---|---|---|---|---|
| 4-43 | $SO_2CH_3$ | $CF_3$ | methyl-1,3,4-oxadiazole | 4-chlorocyclohex-1-enyl | |
| 4-44 | $SO_2CH_3$ | $CF_3$ | methyl-1,3,4-oxadiazole | cyclohexa-1,3-dienyl | |
| 4-45 | $SO_2CH_3$ | $CF_3$ | methyl-1,3,4-oxadiazole | 4-methylcyclopent-1-enyl | |
| 4-46 | $SO_2CH_3$ | $CF_3$ | methyl-1,3,4-oxadiazole | 4-chlorocyclopent-1-enyl | |
| 4-47 | $SO_2CH_3$ | $CF_3$ | methyl-1,3,4-oxadiazole | 4-methoxycyclopent-1-enyl | |
| 4-48 | $NO_2$ | $SO_2CH_3$ | methyl-1,3,4-oxadiazole | cyclohex-1-enyl | |
| 4-49 | $NO_2$ | $SO_2CH_3$ | methyl-1,3,4-oxadiazole | cyclopent-1-enyl | |
| 4-50 | $NO_2$ | Cl | methyl-1,3,4-oxadiazole | cyclohex-1-enyl | |
| 4-51 | Cl | Cl | methyl-1,3,4-oxadiazole | cyclohex-1-enyl | |
| 4-52 | Cl | Cl | methyl-1,3,4-oxadiazole | cyclopent-1-enyl | |

TABLE 4-continued

Structures and Physical Properties of Part of Compounds of Formula 1

| Compound | X₁ | X₃ | Q | Z | Appearance (Melting Point °C.) |
|---|---|---|---|---|---|
| 4-53 | Cl | SO₂CH₃ | 5-methyl-1,3,4-oxadiazol-2-yl | cyclohex-1-en-1-yl | |
| 4-54 | Cl | SO₂CH₃ | 5-methyl-1,3,4-oxadiazol-2-yl | cyclopent-1-en-1-yl | |
| 4-55 | CH₃ | SO₂CH₃ | 5-methyl-1,3,4-oxadiazol-2-yl | cyclohex-1-en-1-yl | |
| 4-56 | CN | SO₂CH₃ | 5-methyl-1,3,4-oxadiazol-2-yl | cyclohex-1-en-1-yl | |
| 4-57 | CF₃ | SO₂CH₃ | 5-methyl-1,3,4-oxadiazol-2-yl | cyclohex-1-en-1-yl | |
| 4-58 | S(=O)CH₃ | SO₂CH₃ | 5-methyl-1,3,4-oxadiazol-2-yl | cyclohex-1-en-1-yl | |
| 4-59 | CH₂OCH₃ | SO₂CH₃ | 5-methyl-1,3,4-oxadiazol-2-yl | cyclohex-1-en-1-yl | |
| 4-60 | CH₂OCH₂CH₂OCH₃ | SO₂CH₃ | 5-methyl-1,3,4-oxadiazol-2-yl | cyclohex-1-en-1-yl | |
| 4-61 | cyclohexyl | SO₂CH₃ | 5-methyl-1,3,4-oxadiazol-2-yl | cyclohex-1-en-1-yl | |
| 4-62 | cyclohexylmethyl | SO₂CH₃ | 5-methyl-1,3,4-oxadiazol-2-yl | cyclohex-1-en-1-yl | |

TABLE 4-continued

Structures and Physical Properties of Part of Compounds of Formula 1

| Compound | X₁ | X₃ | Q | Z | Appearance (Melting Point °C.) |
|---|---|---|---|---|---|
| 4-63 | –CH=CH₂ | SO₂CH₃ | 5-methyl-1,3,4-oxadiazol-2-yl | cyclohex-1-en-1-yl | |
| 4-64 | –C≡CH | SO₂CH₃ | 5-methyl-1,3,4-oxadiazol-2-yl | cyclohex-1-en-1-yl | |
| 4-65 | SO₂CH=CH₂ | SO₂CH₃ | 5-methyl-1,3,4-oxadiazol-2-yl | cyclohex-1-en-1-yl | |
| 4-66 | –SO₂C≡CH | SO₂CH₃ | 5-methyl-1,3,4-oxadiazol-2-yl | cyclohex-1-en-1-yl | |
| 4-67 | phenyl | SO₂CH₃ | 5-methyl-1,3,4-oxadiazol-2-yl | cyclohex-1-en-1-yl | |
| 4-68 | –SO₂-phenyl | SO₂CH₃ | 5-methyl-1,3,4-oxadiazol-2-yl | cyclohex-1-en-1-yl | |
| 4-69 | 4,5-dihydroisoxazol-3-yl | SO₂CH₃ | 5-methyl-1,3,4-oxadiazol-2-yl | cyclohex-1-en-1-yl | |
| 4-70 | 3,5-dimethyl-1H-pyrazol-1-yl | SO₂CH₃ | 5-methyl-1,3,4-oxadiazol-2-yl | cyclohex-1-en-1-yl | |
| 4-71 | isoxazolidin-2-yl | SO₂CH₃ | 5-methyl-1,3,4-oxadiazol-2-yl | cyclohex-1-en-1-yl | |
| 4-72 | 3,5-dimethyl-4,5-dihydro-1H-pyrazol-1-yl | SO₂CH₃ | 5-methyl-1,3,4-oxadiazol-2-yl | cyclohex-1-en-1-yl | |

TABLE 4-continued
Structures and Physical Properties of Part of Compounds of Formula 1
| Compound | $X_1$ | $X_3$ | Q | Z | Appearance (Melting Point °C.) |
|---|---|---|---|---|---|
| 4-73 | $SO_2CH_3$ | $CF_3$ | 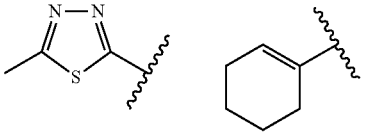 | 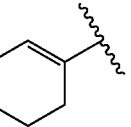 | |
| 4-74 | $SO_2CH_3$ | $CF_3$ | 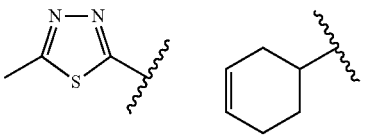 | 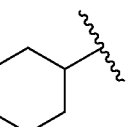 | |
| 4-75 | $SO_2CH_3$ | $CF_3$ | 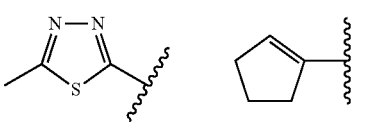 | 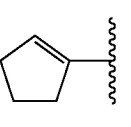 [SMILES: *C1=CCCC1] | |
| 4-76 | $SO_2CH_3$ | $CF_3$ | 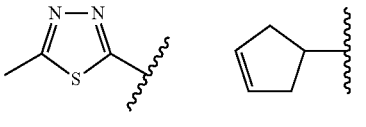 | 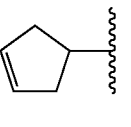 [SMILES: *C1CC=CC1] | |
| 4-77 | $SO_2CH_3$ | $CF_3$ | 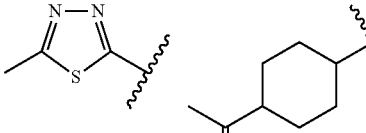 | 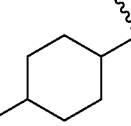 | |
| 4-78 | $SO_2CH_3$ | $CF_3$ | 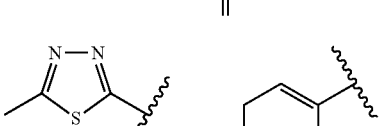 | 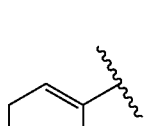 | |
| 4-79 | $SO_2CH_3$ | $CF_3$ |  | 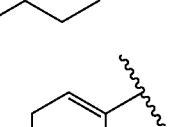 | |
| 4-80 | $SO_2CH_3$ | $CF_3$ | 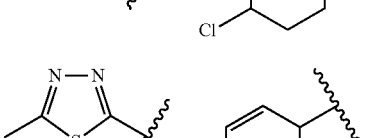 | 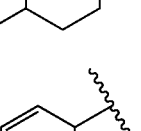 | |
| 4-81 | $SO_2CH_3$ | $CF_3$ |  | 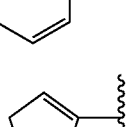 | |
| 4-82 | $SO_2CH_3$ | $CF_3$ |  | 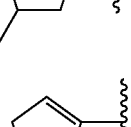 | |

TABLE 4-continued

Structures and Physical Properties of Part of Compounds of Formula 1

| Compound | $X_1$ | $X_3$ | Q | Z | Appearance (Melting Point °C.) |
|---|---|---|---|---|---|
| 4-83 | $SO_2CH_3$ | $CF_3$ | 5-methyl-1,3,4-thiadiazol-2-yl | 4-methoxycyclopent-1-en-1-yl | |
| 4-84 | $NO_2$ | $SO_2CH_3$ | 5-methyl-1,3,4-thiadiazol-2-yl | cyclohex-1-en-1-yl | |
| 4-85 | $NO_2$ | $SO_2CH_3$ | 5-methyl-1,3,4-thiadiazol-2-yl | cyclopent-1-en-1-yl | |
| 4-86 | $NO_2$ | Cl | 5-methyl-1,3,4-thiadiazol-2-yl | cyclohex-1-en-1-yl | |
| 4-87 | Cl | Cl | 5-methyl-1,3,4-thiadiazol-2-yl | cyclohex-1-en-1-yl | |
| 4-88 | Cl | Cl | 5-methyl-1,3,4-thiadiazol-2-yl | cyclopent-1-en-1-yl | |
| 4-89 | Cl | $SO_2CH_3$ | 5-methyl-1,3,4-thiadiazol-2-yl | cyclohex-1-en-1-yl | |
| 4-90 | Cl | $SO_2CH_3$ | 5-methyl-1,3,4-thiadiazol-2-yl | cyclopent-1-en-1-yl | |
| 4-91 | $CH_3$ | $SO_2CH_3$ | 5-methyl-1,3,4-thiadiazol-2-yl | cyclohex-1-en-1-yl | |
| 4-92 | CN | $SO_2CH_3$ | 5-methyl-1,3,4-thiadiazol-2-yl | cyclohex-1-en-1-yl | |

TABLE 4-continued

Structures and Physical Properties of Part of Compounds of Formula 1

| Compound | $X_1$ | $X_3$ | Q | Z | Appearance (Melting Point °C.) |
|---|---|---|---|---|---|
| 4-93 | $CF_3$ | $SO_2CH_3$ | methyl-thiadiazole | cyclohexenyl | |
| 4-94 | $S(=O)CH_3$ | $SO_2CH_3$ | methyl-thiadiazole | cyclohexenyl | |
| 4-95 | $CH_2OCH_3$ | $SO_2CH_3$ | methyl-thiadiazole | cyclohexenyl | |
| 4-96 | $CH_2OCH_2CH_2OCH_3$ | $SO_2CH_3$ | methyl-thiadiazole | cyclohexenyl | |
| 4-97 | cyclohexyl | $SO_2CH_3$ | methyl-thiadiazole | cyclohexenyl | |
| 4-98 | cyclohexylmethyl | $SO_2CH_3$ | methyl-thiadiazole | cyclohexenyl | |
| 4-99 | $CH_2CH=CH_2$ | $SO_2CH_3$ | methyl-thiadiazole | cyclohexenyl | |
| 4-100 | $CH_2C\equiv CH$ | $SO_2CH_3$ | methyl-thiadiazole | cyclohexenyl | |
| 4-101 | $SO_2CH_3=CH_2$ | $SO_2CH_3$ | methyl-thiadiazole | cyclohexenyl | |
| 4-102 | $SO_2C\equiv CH$ | $SO_2CH_3$ | methyl-thiadiazole | cyclohexenyl | |

TABLE 4-continued

Structures and Physical Properties of Part of Compounds of Formula 1

| Compound | X₁ | X₃ | Q | Z | Appearance (Melting Point °C.) |
|---|---|---|---|---|---|
| 4-103 | phenyl | SO₂CH₃ | methyl-1,3,4-thiadiazolyl | cyclohexenyl | |
| 4-104 | phenylsulfonyl | SO₂CH₃ | methyl-1,3,4-thiadiazolyl | cyclohexenyl | |
| 4-105 | 4,5-dihydroisoxazol-3-yl | SO₂CH₃ | methyl-1,3,4-thiadiazolyl | cyclohexenyl | |
| 4-106 | 3,5-dimethylpyrazol-1-yl | SO₂CH₃ | methyl-1,3,4-thiadiazolyl | cyclohexenyl | |
| 4-107 | isoxazolidin-2-ylmethyl | SO₂CH₃ | methyl-1,3,4-thiadiazolyl | cyclohexenyl | |
| 4-108 | (3,5-dimethylpyrazol-1-yl)methyl | SO₂CH₃ | methyl-1,3,4-thiadiazolyl | cyclohexenyl | |
| 4-109 | SO₂CH₃ | CF₃ | 2-methyl-2H-tetrazol-5-yl | cyclohexenyl | |
| 4-110 | SO₂CH₃ | CF₃ | 2-methyl-2H-tetrazol-5-yl | cyclohexenyl | |
| 4-111 | SO₂CH₃ | CF₃ | 2-methyl-2H-tetrazol-5-yl | cyclopentenyl | |
| 4-112 | SO₂CH₃ | CF₃ | 2-methyl-2H-tetrazol-5-yl | cyclopentenyl | |

TABLE 4-continued
Structures and Physical Properties of Part of Compounds of Formula 1
| Compound | $X_1$ | $X_3$ | Q | Z | Appearance (Melting Point °C.) |
|---|---|---|---|---|---|
| 4-113 | $SO_2CH_3$ | $CF_3$ | 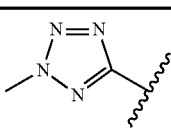 | 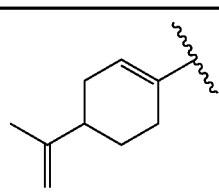 | |
| 4-114 | $SO_2CH_3$ | $CF_3$ | 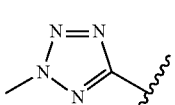 | 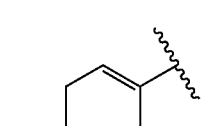 | |
| 4-115 | $SO_2CH_3$ | $CF_3$ | 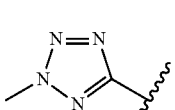 | 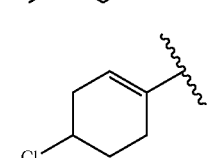 | |
| 4-116 | $SO_2CH_3$ | $CF_3$ | 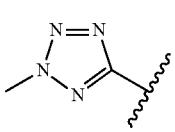 | 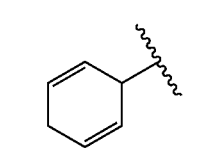 [SMILES: *C1C=CCC=C1] | |
| 4-117 | $SO_2CH_3$ | $CF_3$ | 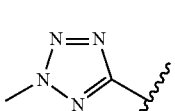 | 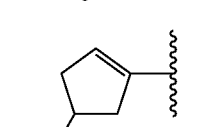 | |
| 4-118 | $SO_2CH_3$ | $CF_3$ | 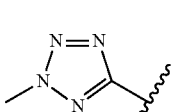 | 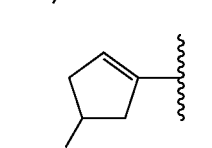 | |
| 4-119 | $SO_2CH_3$ | CF | 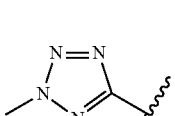 | 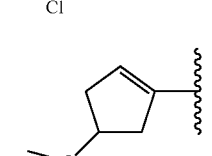 | |
| 4-120 | $NO_2$ | $SO_2CH_3$ | 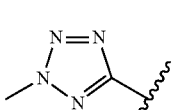 | 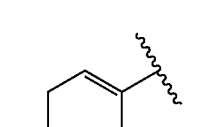 | |
| 4-121 | $NO_2$ | $SO_2CH_3$ | 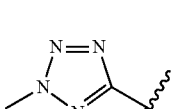 | 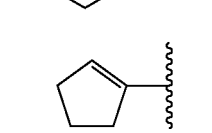 | |
| 4-122 | $NO_2$ | Cl | 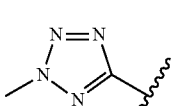 | 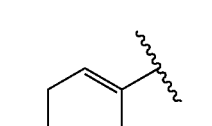 | |

TABLE 4-continued
Structures and Physical Properties of Part of Compounds of Formula 1
| Compound | X₁ | X₃ | Q | Z | Appearance (Melting Point °C.) |
|---|---|---|---|---|---|
| 4-123 | Cl | Cl | 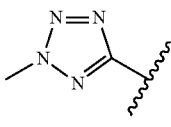 [SMILES: *c1nnn(C)n1] | 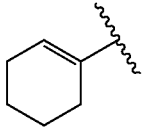 | |
| 4-124 | Cl | Cl | 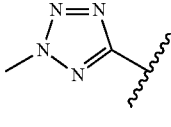 [SMILES: *c1nnn(C)n1] | 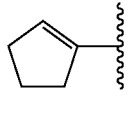 [SMILES: *C1=CCCC1] | |
| 4-125 | Cl | SO₂CH₃ | 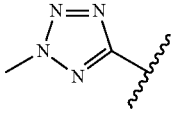 [SMILES: *c1nnn(C)n1] | 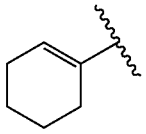 [SMILES: *C1=CCCCC1] | |
| 4-126 | Cl | SO₂CH₃ | 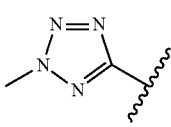 [SMILES: *c1nnn(C)n1] | 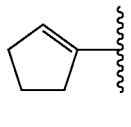 [SMILES: *C1=CCCC1] | |
| 4-127 | CH₃ | SO₂CH₃ | 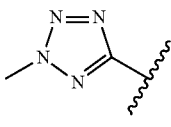 [SMILES: *c1nnn(C)n1] | 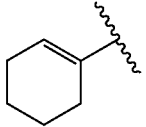 [SMILES: *C1=CCCCC1] | |
| 4-128 | CN | SO₂CH₃ | 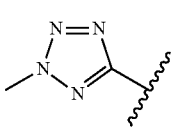 [SMILES: *c1nnn(C)n1] | 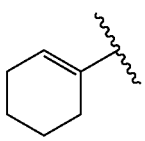 [SMILES: *C1=CCCCC1] | |
| 4-129 | CF₃ | SO₂CH₃ | 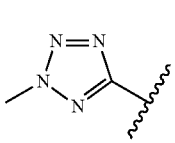 [SMILES: *c1nnn(C)n1] | 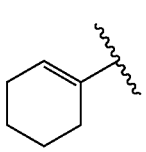 [SMILES: *C1=CCCCC1] | |
| 4-130 | 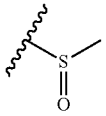 [SMILES: *S(C)=O] | SO₂CH₃ | 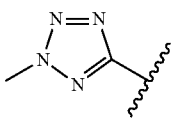 [SMILES: *c1nnn(C)n1] | 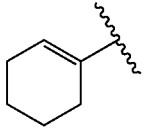 [SMILES: *C1=CCCCC1] | |
| 4-131 | 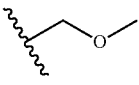 | SO₂CH₃ | 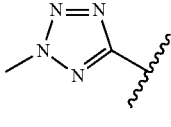 [SMILES: *c1nnn(C)n1] | 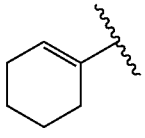 [SMILES: *C1=CCCCC1] | |
| 4-132 | 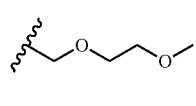 | SO₂CH₃ | 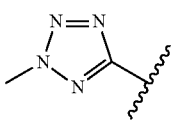 [SMILES: *c1nnn(C)n1] | 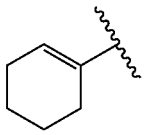 [SMILES: *C1=CCCCC1] | |

TABLE 4-continued

Structures and Physical Properties of Part of Compounds of Formula 1

| Compound | $X_1$ | $X_3$ | Q | Z | Appearance (Melting Point °C.) |
|---|---|---|---|---|---|
| 4-133 | cyclohexyl | $SO_2CH_3$ | 2-methyl-2H-tetrazol-5-yl | cyclohexenyl | |
| 4-134 | cyclohexylmethyl | $SO_2CH_3$ | 2-methyl-2H-tetrazol-5-yl | cyclohexenyl | |
| 4-135 | vinyl | $SO_2CH_3$ | 2-methyl-2H-tetrazol-5-yl | cyclohexenyl | |
| 4-136 | ethynyl | $SO_2CH_3$ | 2-methyl-2H-tetrazol-5-yl | cyclohexenyl | |
| 4-137 | $SO_2CH_3={CH_2}$ | $SO_2CH_3$ | 2-methyl-2H-tetrazol-5-yl | cyclohexenyl | |
| 4-138 | ethynylsulfonyl | $SO_2CH_3$ | 2-methyl-2H-tetrazol-5-yl | cyclohexenyl | |
| 4-139 | phenyl | $SO_2CH_3$ | 2-methyl-2H-tetrazol-5-yl | cyclohexenyl | |
| 4-140 | phenylsulfonyl | $SO_2CH_3$ | 2-methyl-2H-tetrazol-5-yl | cyclohexenyl | |
| 4-141 | 4,5-dihydroisoxazol-3-yl | $SO_2CH_3$ | 2-methyl-2H-tetrazol-5-yl | cyclohexenyl | |
| 4-142 | 1,4-dimethyl-2,5-dihydro-1H-imidazol-2-yl | $SO_2CH_3$ | 2-methyl-2H-tetrazol-5-yl | cyclohexenyl | |

TABLE 4-continued

Structures and Physical Properties of Part of Compounds of Formula 1

| Compound | X₁ | X₃ | Q | Z | Appearance (Melting Point °C.) |
|---|---|---|---|---|---|
| 4-143 | isoxazolidin-2-ylmethyl | SO₂CH₃ | 2-methyl-2H-tetrazol-5-yl | cyclohex-1-en-1-yl | |
| 4-144 | (3,5-dimethyl-1H-pyrazol-1-yl)methyl | SO₂CH₃ | 2-methyl-2H-tetrazol-5-yl | cyclohex-1-en-1-yl | |
| 4-145 | SO₂CH₃ | CF₃ | 1-methyl-1H-1,2,4-triazol-5-yl | cyclohex-1-en-1-yl | |
| 4-146 | SO₂CH₃ | CF₃ | 1-methyl-1H-1,2,4-triazol-5-yl | cyclohex-3-en-1-yl | |
| 4-147 | SO₂CH₃ | CF₃ | 1-methyl-1H-1,2,4-triazol-5-yl | cyclopent-1-en-1-yl | |
| 4-148 | SO₂CH₃ | CF₃ | 1-methyl-1H-1,2,4-triazol-5-yl | cyclopent-3-en-1-yl | |
| 4-149 | SO₂CH₃ | CF₃ | 1-methyl-1H-1,2,4-triazol-5-yl | 4-(prop-1-en-2-yl)cyclohex-1-en-1-yl | |
| 4-150 | SO₂CH₃ | CF₃ | 1-methyl-1H-1,2,4-triazol-5-yl | 4-methylcyclohex-1-en-1-yl | |
| 4-151 | SO₂CH₃ | CF₃ | 1-methyl-1H-1,2,4-triazol-5-yl | 4-chlorocyclohex-1-en-1-yl | |
| 4-152 | SO₂CH₃ | CF₃ | 1-methyl-1H-1,2,4-triazol-5-yl | cyclohexa-2,5-dien-1-yl | |

TABLE 4-continued

Structures and Physical Properties of Part of Compounds of Formula 1

| Compound | $X_1$ | $X_3$ | Q | Z | Appearance (Melting Point °C.) |
|---|---|---|---|---|---|
| 4-153 | $SO_2CH_3$ | $CF_3$ | triazole | methylcyclopentenyl | |
| 4-154 | $SO_2CH_3$ | $CF_3$ | triazole | chlorocyclopentenyl | |
| 4-155 | $SO_2CH_3$ | $CF_3$ | triazole | methoxycyclopentenyl | |
| 4-156 | $NO_2$ | $SO_2CH_3$ | triazole | cyclohexenyl | |
| 4-157 | $NO_2$ | $SO_2CH_3$ | triazole | cyclopentenyl | |
| 4-158 | $NO_2$ | Cl | triazole | cyclohexenyl | |
| 4-159 | Cl | Cl | triazole | cyclohexenyl | |
| 4-160 | Cl | Cl | triazole | cyclopentenyl | |
| 4-161 | Cl | $SO_2CH_3$ | triazole | cyclohexenyl | |
| 4-162 | Cl | $SO_2CH_3$ | triazole | cyclopentenyl | |

TABLE 4-continued
Structures and Physical Properties of Part of Compounds of Formula 1
| Compound | X₁ | X₃ | Q | Z | Appearance (Melting Point °C.) |
|---|---|---|---|---|---|
| 4-163 | CH₃ | SO₂CH₃ | 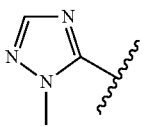 [SMILES: *c1ncnn1C] | 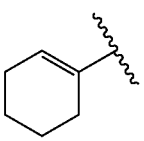 [SMILES: *C1=CCCCC1] | |
| 4-164 | CN | SO₂CH₃ | 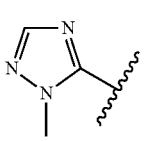 | 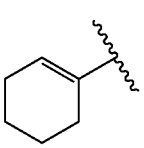 [SMILES: *C1=CCCCC1] | |
| 4-165 | CF₃ | SO₂CH₃ | 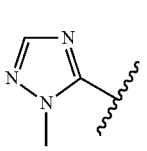 [SMILES: *c1ncnn1C] | 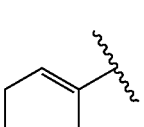 | |
| 4-166 | 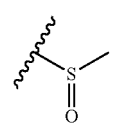 [SMILES: *S(C)=O] | SO₂CH₃ | 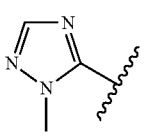 | 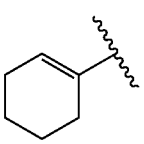 [SMILES: *C1=CCCCC1] | |
| 4-167 | 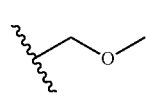 [SMILES: *COC] | SO₂CH₃ | 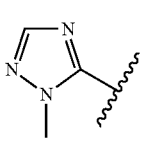 | 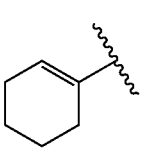 [SMILES: *C1=CCCCC1] | |
| 4-168 | 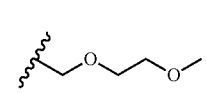 [SMILES: *COCCOC] | SO₂CH₃ | 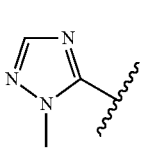 [SMILES: *c1ncnn1C] | 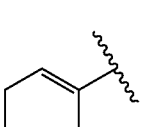 | |
| 4-169 | 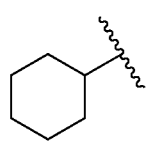 [SMILES: *C1CCCCC1] | SO₂CH₃ | 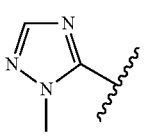 | 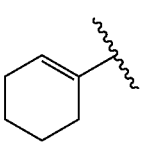 [SMILES: *C1=CCCCC1] | |
| 4-170 | 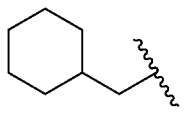 [SMILES: *CC1CCCCC1] | SO₂CH₃ | 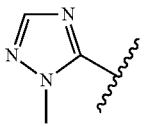 [SMILES: *c1ncnn1C] | 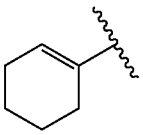 [SMILES: *C1=CCCCC1] | |
| 4-171 |  | SO₂CH₃ | 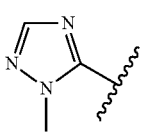 | 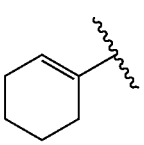 [SMILES: *C1=CCCCC1] | |
| 4-172 |  | SO₂CH₃ | 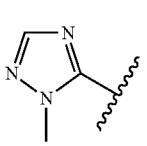 | 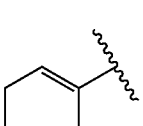 | |

TABLE 4-continued

Structures and Physical Properties of Part of Compounds of Formula 1

| Compound | X₁ | X₃ | Q | Z | Appearance (Melting Point °C.) |
|---|---|---|---|---|---|
| 4-173 | SO₂CH₃=CH₂ | SO₂CH₃ | 1-methyl-1,2,4-triazol-5-yl | cyclohex-1-en-1-yl | |
| 4-174 | ethynylsulfonyl | SO₂CH₃ | 1-methyl-1,2,4-triazol-5-yl | cyclohex-1-en-1-yl | |
| 4-175 | phenyl | SO₂CH₃ | 1-methyl-1,2,4-triazol-5-yl | cyclohex-1-en-1-yl | |
| 4-176 | phenylsulfonyl | SO₂CH₃ | 1-methyl-1,2,4-triazol-5-yl | cyclohex-1-en-1-yl | |
| 4-177 | 4,5-dihydroisoxazol-3-yl | SO₂CH₃ | 1-methyl-1,2,4-triazol-5-yl | cyclohex-1-en-1-yl | |
| 4-178 | 3,5-dimethylpyrazol-1-yl | SO₂CH₃ | 1-methyl-1,2,4-triazol-5-yl | cyclohex-1-en-1-yl | |
| 4-179 | isoxazolidin-2-ylmethyl | SO₂CH₃ | 1-methyl-1,2,4-triazol-5-yl | cyclohex-1-en-1-yl | |
| 4-180 | (3,5-dimethylpyrazol-1-yl)methyl | SO₂CH₃ | 1-methyl-1,2,4-triazol-5-yl | cyclohex-1-en-1-yl | |
| 4-181 | SO₂CH₃ | CF₃ | 4-methyl-1,2,5-oxadiazol-3-yl | cyclohex-1-en-1-yl | |
| 4-182 | SO₂CH₃ | CF₃ | 4-methyl-1,2,5-oxadiazol-3-yl | cyclohex-3-en-1-yl | |

TABLE 4-continued

Structures and Physical Properties of Part of Compounds of Formula 1

| Compound | $X_1$ | $X_3$ | Q | Z | Appearance (Melting Point °C.) |
|---|---|---|---|---|---|
| 4-183 | $SO_2CH_3$ | $CF_3$ | | | |
| 4-184 | $SO_2CH_3$ | $CF_3$ | | | |
| 4-185 | $SO_2CH_3$ | $CF_3$ | | | |
| 4-186 | $SO_2CH_3$ | $CF_3$ | | | |
| 4-187 | $SO_2CH_3$ | $CF_3$ | | | |
| 4-188 | $SO_2CH_3$ | $CF_3$ | | | |
| 4-189 | $SO_2CH_3$ | $CF_3$ | | | |
| 4-190 | $SO_2CH_3$ | $CF_3$ | | | |
| 4-191 | $SO_2CH_3$ | $CF_3$ | | | |
| 4-192 | $NO_2$ | $SO_2CH_3$ | | | |

TABLE 4-continued
Structures and Physical Properties of Part of Compounds of Formula 1
| Compound | X₁ | X₃ | Q | Z | Appearance (Melting Point °C.) |
|---|---|---|---|---|---|
| 4-193 | NO₂ | SO₂CH₃ | 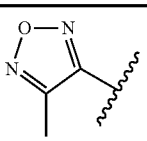 | 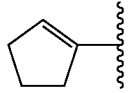 [SMILES: *C1=CCCC1] | |
| 4-194 | NO₂ | Cl | 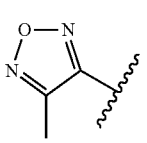 [SMILES: *c1nonc1C] | 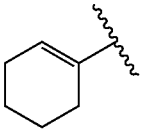 [SMILES: *C1=CCCCC1] | |
| 4-195 | Cl | Cl | 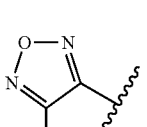 | 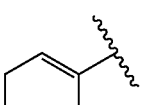 | |
| 4-196 | Cl | Cl | 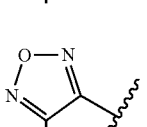 | 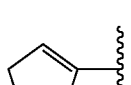 | |
| 4-197 | Cl | SO₂CH₃ | 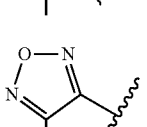 | 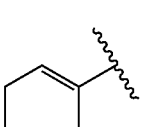 | |
| 4-198 | Cl | SO₂CH₃ | 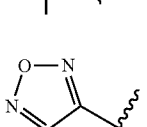 | 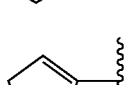 | |
| 4-199 | CH₃ | SO₂CH₃ | 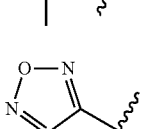 | 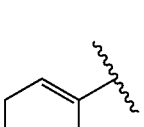 | |
| 4-200 | CN | SO₂CH₃ | 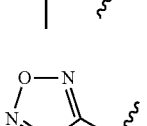 | 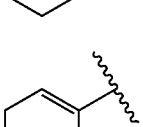 | |
| 4-201 | CF₃ | SO₂CH₃ | 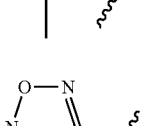 | 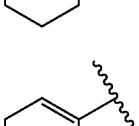 | |
| 4-202 | 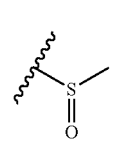 [SMILES: *S(C)=O] | SO₂CH₃ | 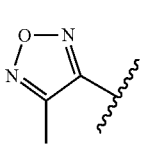 [SMILES: *c1nonc1C] | 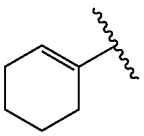 [SMILES: *C1=CCCCC1] | |

TABLE 4-continued

Structures and Physical Properties of Part of Compounds of Formula 1

| Compound | X₁ | X₃ | Q | Z | Appearance (Melting Point °C.) |
|---|---|---|---|---|---|
| 4-203 | —CH₂OCH₃ | SO₂CH₃ | methylfurazanyl | cyclohexenyl | |
| 4-204 | —CH₂OCH₂CH₂OCH₃ | SO₂CH₃ | methylfurazanyl | cyclohexenyl | |
| 4-205 | cyclohexyl | SO₂CH₃ | methylfurazanyl | cyclohexenyl | |
| 4-206 | cyclohexylmethyl | SO₂CH₃ | methylfurazanyl | cyclohexenyl | |
| 4-207 | —CH₂CH=CH₂ | SO₂CH₃ | methylfurazanyl | cyclohexenyl | |
| 4-208 | —CH₂C≡CH | SO₂CH₃ | methylfurazanyl | cyclohexenyl | |
| 4-209 | SO₂CH₃=CH₂ | SO₂CH₃ | methylfurazanyl | cyclohexenyl | |
| 4-210 | —S(O)₂C≡CH | SO₂CH₃ | methylfurazanyl | cyclohexenyl | |
| 4-211 | phenyl | SO₂CH₃ | methylfurazanyl | cyclohexenyl | |
| 4-212 | —S(O)₂Ph | SO₂CH₃ | methylfurazanyl | cyclohexenyl | |

TABLE 4-continued

Structures and Physical Properties of Part of Compounds of Formula 1

| Compound | X₁ | X₃ | Q | Z | Appearance (Melting Point °C.) |
|---|---|---|---|---|---|
| 4-213 | 4,5-dihydroisoxazol-3-yl | SO₂CH₃ | 4-methyl-1,2,5-oxadiazol-3-yl | cyclohex-1-en-1-yl | |
| 4-214 | 3,5-dimethyl-1H-pyrazol-1-yl | SO₂CH₃ | 4-methyl-1,2,5-oxadiazol-3-yl | cyclohex-1-en-1-yl | |
| 4-215 | isoxazolidin-2-ylmethyl | SO₂CH₃ | 4-methyl-1,2,5-oxadiazol-3-yl | cyclohex-1-en-1-yl | |
| 4-216 | (3,5-dimethyl-1H-pyrazol-1-yl)methyl | SO₂CH₃ | 4-methyl-1,2,5-oxadiazol-3-yl | cyclohex-1-en-1-yl | |
| 4-217 | 1H-1,2,4-triazol-1-yl | CF₃ | 1-methyl-1H-tetrazol-5-yl | cyclohex-1-en-1-yl | |
| 4-218 | 1H-imidazol-1-yl | CF₃ | 1-methyl-1H-tetrazol-5-yl | cyclohex-1-en-1-yl | |
| 4-219 | 2-methyl-1H-imidazol-1-yl | CF₃ | 1-methyl-1H-tetrazol-5-yl | cyclohex-1-en-1-yl | |
| 4-220 | 4-isopropyl-1H-pyrazol-1-yl | CF₃ | 1-methyl-1H-tetrazol-5-yl | cyclohex-1-en-1-yl | |
| 4-221 | 4-bromo-1H-pyrazol-1-yl | CF₃ | 1-methyl-1H-tetrazol-5-yl | cyclohex-1-en-1-yl | |

TABLE 4-continued

Structures and Physical Properties of Part of Compounds of Formula 1

| Compound | $X_1$ | $X_3$ | Q | Z | Appearance (Melting Point °C.) |
|---|---|---|---|---|---|
| 4-222 | 3,5-dimethylpyrazol-1-yl | $CF_3$ | 1-methyltetrazol-5-yl | cyclohex-1-en-1-yl | |
| 4-223 | 4-iodopyrazol-1-yl | CF | 1-methyltetrazol-5-yl | cyclohex-1-en-1-yl | |
| 4-224 | 4-chloropyrazol-1-yl | $CF_3$ | 1-methyltetrazol-5-yl | cyclohex-1-en-1-yl | |
| 4-225 | 4-methylpyrazol-1-yl | $CF_3$ | 1-methyltetrazol-5-yl | cyclohex-1-en-1-yl | |
| 4-226 | 3-methylpyrazol-1-yl | $CF_3$ | 1-methyltetrazol-5-yl | cyclohex-1-en-1-yl | |
| 4-227 | 5-methylpyrazol-1-yl | $CF_3$ | 1-methyltetrazol-5-yl | cyclohex-1-en-1-yl | |
| 4-228 | 2-isopropylimidazol-1-yl | $CF_3$ | 1-methyltetrazol-5-yl | cyclohex-1-en-1-yl | |
| 4-229 | 3-ethyl-1,2,4-triazol-1-yl | $CF_3$ | 1-methyltetrazol-5-yl | cyclohex-1-en-1-yl | |
| 4-230 | 3-methyl-1,2,4-triazol-1-yl | $CF_3$ | 1-methyltetrazol-5-yl | cyclohex-1-en-1-yl | |

TABLE 4-continued

Structures and Physical Properties of Part of Compounds of Formula 1

| Compound | X₁ | X₃ | Q | Z | Appearance (Melting Point °C.) |
|---|---|---|---|---|---|
| 4-231 | 3-phenyl-1,2,4-triazol-1-yl | CF₃ | 1-methyltetrazol-5-yl | cyclohexenyl | |
| 4-232 | 3-(methoxymethyl)-1,2,4-triazol-1-yl | CF₃ | 1-methyltetrazol-5-yl | cyclohexenyl | |
| 4-233 | 3-propyl-1,2,4-triazol-1-yl | CF₃ | 1-methyltetrazol-5-yl | cyclohexenyl | |
| 4-234 | 1,2,4-triazol-1-yl | CF₃ | 1-methyltetrazol-5-yl | cyclohexenyl | |
| 4-235 | 1,2,3-triazol-1-yl | CF₃ | 1-methyltetrazol-5-yl | cyclohexenyl | |
| 4-236 | 3-cyano-1,2,4-triazol-1-yl | CF₃ | 1-methyltetrazol-5-yl | cyclohexenyl | |
| 4-237 | 3-trifluoromethyl-1,2,4-triazol-1-yl | CF₃ | 1-methyltetrazol-5-yl | cyclohexenyl | |
| 4-238 | 3-bromo-1,2,4-triazol-1-yl | CF₃ | 1-methyltetrazol-5-yl | cyclohexenyl | |
| 4-239 | 3-methoxy-1,2,4-triazol-1-yl | CF₃ | 1-methyltetrazol-5-yl | cyclohexenyl | |

TABLE 4-continued

Structures and Physical Properties of Part of Compounds of Formula 1

| Compound | $X_1$ | $X_3$ | Q | Z | Appearance (Melting Point °C.) |
|---|---|---|---|---|---|
| 4-240 | 3-(trifluoromethyl)-5-methyl-1H-1,2,4-triazol-1-yl | $CF_3$ | 1-methyl-1H-tetrazol-5-yl | cyclohex-1-en-1-yl | |
| 4-241 | 3,5-dimethyl-1H-1,2,4-triazol-1-yl | $CF_3$ | 1-methyl-1H-tetrazol-5-yl | cyclohex-1-en-1-yl | |
| 4-242 | 3-chloro-1H-1,2,4-triazol-1-yl | $CF_3$ | 1-methyl-1H-tetrazol-5-yl | cyclohex-1-en-1-yl | |
| 4-243 | 3-amino-1H-1,2,4-triazol-1-yl | $CF_3$ | 1-methyl-1H-tetrazol-5-yl | cyclohex-1-en-1-yl | |
| 4-244 | 3-chloro-5-methyl-1H-1,2,4-triazol-1-yl | $CF_3$ | 1-methyl-1H-tetrazol-5-yl | cyclohex-1-en-1-yl | |
| 4-245 | 3-cyano-1H-pyrazol-1-yl | $CF_3$ | 1-methyl-1H-tetrazol-5-yl | cyclohex-1-en-1-yl | |
| 4-246 | 4-(trifluoromethyl)-2-methyl-1H-pyrrol-1-yl | $CF_3$ | 1-methyl-1H-tetrazol-5-yl | cyclohex-1-en-1-yl | |
| 4-247 | 4,5-dichloro-1H-imidazol-1-yl | $CF_3$ | 1-methyl-1H-tetrazol-5-yl | cyclohex-1-en-1-yl | |
| 4-248 | Cl | $CF_3$ | 1-methyl-1H-tetrazol-5-yl | cyclohex-1-en-1-yl | white oil |

TABLE 4-continued

Structures and Physical Properties of Part of Compounds of Formula 1

| Compound | $X_1$ | $X_3$ | Q | Z | Appearance (Melting Point °C.) |
|---|---|---|---|---|---|
| 4-249 | Cl | $CF_3$ | 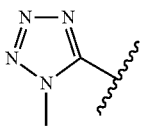 [SMILES: *c1nnnn1C] | 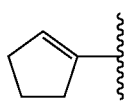 [SMILES: *C1=CCCC1] | white oil |

$^1$H NMR data of part of compounds is as follows:

Compound 1-1 (600 MHz, DMSO-$d_6$): 8.40 (s, 1H), 8.28 (d, 1H), 8.18 (d, 1H), 7.79 (d, 1H), 7.63 (d, 2H), 7.40-7.47 (m, 3H), 6.56 (s, 1H), 4.17 (s, 3H), 3.41 (s, 3H).

Compound 1-8 (600 MHz, DMSO-$d_6$): 8.39 (s, 1H), 8.31 (s, 1H), 8.27 (d, 1H), 8.16 (d, 1H), 7.70 (d, 1H), 7.34 (s, 1H), 7.17 (d, 1H), 6.96 (d, 1H), 6.09 (s, 2H), 4.16 (s, 3H), 3.39 (s, 3H).

Compound 1-12 (600 MHz, DMSO-$d_6$): 8.78 (s, 1H), 8.52 (s, 1H), 8.27 (s, 1H), 7.79 (d, 1H), 7.65 (s, 2H), 7.42-7.45 (m, 3H), 6.56 (d, 1H), 4.22 (s, 3H), 3.46 (s, 3H).

Compound 1-13 (600 MHz, DMSO-$d_6$): 8.76 (s, 1H), 8.50 (d, 1H), 8.24 (d, 1H), 7.70 (d, 1H), 7.37 (s, 1H), 7.18 (d, 1H), 6.96 (d, 1H), 6.07-6.09 (m, 3H), 4.20 (s, 3H), 3.46 (s, 3H).

Compound 1-14 (600 MHz, DMSO-$d_6$): 8.43 (d, 1H), 8.07 (dd, 1H), 7.98 (d, 1H), 7.79 (d, 1H), 7.65 (d, 2H), 7.41-7.43 (m, 3H), 6.65 (d, 1H), 4.17 (s, 3H).

Compound 1-15 (600 MHz, DMSO-$d_6$): 7.81-7.83 (m, 3H), 7.67 (d, 2H), 7.59 (d, 1H), 7.43-7.47 (m, 3H), 6.90 (d, 1H), 4.09 (s, 3H).

Compound 1-16 (600 MHz, DMSO-$d_6$): 7.80-7.82 (m, 2H), 7.72-7.75 (m, 1H), 7.58 (dd, 1H), 7.34 (s, 1H), 7.22 (d, 1H), 6.98 (d, 1H), 6.65 (d, 1H), 6.10 (s, 2H), 4.08 (s, 3H).

Compound 1-17 (600 MHz, DMSO-$d_6$): 8.14 (s, 1H), 8.10 (d, 1H), 8.02 (d, 1H), 7.83 (d, 1H), 7.67 (d, 2H), 7.42-7.49 (m, 3H), 6.82 (s, 1H), 4.14 (s, 3H), 3.35 (s, 3H).

Compound 1-18 (600 MHz, DMSO-$d_6$): 8.14 (s, 1H), 8.08 (d, 1H), 8.01 (dd, 1H), 7.74 (d, 1H), 7.37 (s, 1H), 7.22 (d, 1H), 6.98 (d, 1H), 6.56 (d, 1H), 6.10 (s, 2H), 4.12 (s, 3H), 3.36 (s, 3H).

Compound 1-19 (600 MHz, DMSO-$d_6$): 8.03 (d, 1H), 7.89 (d, 1H), 7.82 (d, 1H), 7.66 (d, 2H), 7.39-7.49 (m, 3H), 6.79 (d, 1H), 4.14 (s, 3H), 3.32 (s, 3H), 2.72 (s, 3H).

Compound 1-20 (600 MHz, DMSO-$d_6$): 8.02 (d, 1H), 7.88 (d, 1H), 7.73 (d, 1H), 7.36 (s, 1H), 7.21 (d, 1H), 6.98 (d, 1H), 6.54 (d, 1H), 6.10 (s, 3H), 4.13 (s, 3H), 3.34 (s, 3H), 2.72 (s, 3H).

Compound 1-21 (600 MHz, DMSO-$d_6$): 8.02 (d, 1H), 7.87 (d, 1H), 7.78 (d, 1H), 7.63 (d, 2H), 6.98 (d, 2H), 6.58 (d, 1H), 4.13 (s, 3H), 3.80 (s, 3H), 3.33 (s, 3H), 2.72 (s, 3H).

Compound 1-22 (600 MHz, DMSO-$d_6$): 8.03 (d, 1H), 7.86-7.91 (m, 2H), 7.71-7.76 (m, 6H), 7.49 (t, 2H), 7.41 (t, 1H), 6.82 (d, 1H), 4.15 (s, 3H), 3.34 (s, 3H), 2.73 (s, 3H).

Compound 1-24 (600 MHz, DMSO-$d_6$): 8.10 (d, 1H), 8.06 (d, 1H), 7.82 (d, 1H), 7.66 (d, 2H), 7.42-7.49 (m, 3H), 6.76 (d, 1H), 4.95 (s, 2H), 4.15 (s, 3H), 3.39 (s, 3H), 3.35 (s, 3H).

Compound 1-26 (600 MHz, CDCl$_3$): 8.18 (d, 1H), 7.84 (d, 1H), 7.66 (d, 1H), 7.42 (d, 2H), 6.89 (d, 2H), 6.42 (d, 1H), 5.07 (s, 2H), 4.06 (s, 3H), 3.85 (s, 3H), 3.49 (s, 3H), 3.25 (s, 3H).

Compound 1-28 (600 MHz, CDCl$_3$): 8.18 (d, 1H), 7.88 (d, 1H), 7.64-7.67 (m, 3H), 7.58-7.61 (m, 2H), 6.79 (d, 1H), 5.05 (s, 2H), 4.05 (s, 3H), 3.47 (s, 3H), 3.23 (s, 3H).

Compound 1-30 (600 MHz, DMSO-$d_6$): 8.11 (d, 2H), 7.87 (d, 1H), 7.72-7.78 (m, 7H), 7.49 (t, 2H), 7.41 (t, 1H), 4.96 (s, 2H), 4.17 (s, 3H), 3.40 (s, 3H), 3.38 (s, 3H).

Compound 1-31 (600 MHz, CDCl$_3$): 8.17 (d, 1H), 7.77 (d, 1H), 7.65 (d, 1H), 7.00 (dd, 1H), 6.91 (d, 1H), 6.81 (d, 1H), 6.40 (d, 1H), 6.03 (s, 2H), 5.06 (s, 2H), 4.05 (s, 3H), 3.48 (s, 3H), 3.24 (s, 3H).

Compound 1-33 (600 MHz, CDCl$_3$): 8.75 (d, 1H), 8.20 (d, 1H), 8.13 (d, 1H), 7.96 (d, 1H), 7.88 (d, 1H), 7.68-7.70 (m, 2H), 7.58-7.60 (m, 1H), 7.54-7.56 (m, 1H), 7.48 (t, 1H), 6.71 (d, 1H), 5.08 (s, 2H), 4.09 (s, 3H), 3.49 (s, 3H), 3.25 (s, 3H).

Compound 1-41 (600 MHz, DMSO-$d_6$): 8.06-8.11 (m, 2H), 7.82 (d, 1H), 7.65 (d, 2H), 7.43-7.48 (m, 4H), 5.06 (s, 2H), 4.15 (s, 3H), 3.69-3.72 (m, 1H), 3.50-3.62 (m, 4H), 3.38 (s, 3H), 1.75-1.78 (m, 3H), 1.49-1.54 (m, 1H).

Compound 1-53 (600 MHz, DMSO-$d_6$): 8.09 (s, 2H), 7.82 (d, 1H), 7.66 (d, 2H), 7.43-7.47 (m, 3H), 6.78 (d, 1H), 5.05 (s, 2H), 4.16 (s, 3H), 3.68 (s, 2H), 3.49 (s, 2H), 3.37 (s, 3H), 3.23 (s, 3H).

Compound 1-56 (600 MHz, CDCl$_3$): 7.98 (d, 1H), 7.87 (d, 1H), 7.43-7.48 (m, 4H), 7.36-7.41 (m, 2H), 6.61 (d, 1H), 4.06 (s, 3H), 4.05 (s, 3H), 3.24 (s, 3H).

Compound 1-57 (600 MHz, CDCl$_3$): 7.98 (d, 1H), 7.87 (d, 1H), 7.36-7.49 (m, 6H), 6.62 (d, 1H), 4.27 (q, 2H), 4.05 (s, 3H), 3.25 (s, 3H), 1.49 (t, 3H).

Compound 1-90 (600 MHz, DMSO-$d_6$): 8.15 (d, 1H), 8.07 (d, 1H), 7.85 (d, 1H), 7.67 (d, 2H), 7.43-7.48 (m, 3H), 6.76 (d, 1H), 4.16 (s, 3H), 3.48 (s, 3H).

Compound 1-91 (600 MHz, CDCl$_3$): 7.79-7.84 (m, 2H), 7.67-7.69 (m, 3H), 7.44-7.49 (m, 3H), 7.08 (d, 1H), 4.10 (s, 3H), 3.22 (s, 3H), 2.60 (s, 3H), 2.40 (s, 3H).

compound 1-95 (600 MHz, CDCl$_3$): 7.92 (d, 1H), 7.81 (d, 1H), 7.46-7.53 (m, 5H), 7.19 (d, 1H), 6.87 (d, 1H), 4.01 (s, 3H), 3.96 (s, 3H), 3.22 (s, 3H), 2.53 (s, 3H).

Compound 1-96 (600 MHz, DMSO-$d_6$): 7.81 (d, 1H), 7.73 (d, 1H), 7.63-7.68 (m, 3H), 7.44-7.49 (m, 3H), 7.05 (d, 1H), 4.10 (s, 3H), 4.01 (q, 2H), 3.29 (s, 3H), 2.41 (s, 3H), 1.41 (t, 3H).

Compound 1-97 (600 MHz, DMSO-$d_6$): 7.81 (d, 1H), 7.75 (d, 1H), 7.67-7.68 (m, 3H), 7.44-7.49 (m, 3H), 7.07 (d, 1H), 4.06-4.11 (m, 5H), 3.74 (t, 2H), 3.36 (s, 3H), 3.33 (s, 3H), 2.44 (s, 3H).

Compound 1-98 (600 MHz, CDCl$_3$): 7.88 (d, 1H), 7.85 (d, 1H), 7.79 (d, 1H), 7.66-7.68 (m, 2H), 7.43-7.49 (m, 3H), 7.03 (d, 1H), 4.86 (s, 2H), 4.11 (s, 3H), 3.38 (s, 3H), 3.25 (s, 3H), 2.51 (s, 3H).

Compound 1-100 (600 MHz, CDCl$_3$): 7.91 (d, 1H), 7.82 (d, 1H), 7.40-7.52 (m, 5H), 7.20 (d, 1H), 6.86 (d, 1H), 4.37-4.41 (m, 1H), 4.03-4.09 (m, 2H), 4.01 (s, 3H), 3.95-

3.98 (m, 1H), 3.86-3.90 (m, 1H), 3.28 (s, 3H), 2.56 (s, 3H), 2.06-2.12 (m, 1H), 1.93-1.99 (m, 2H), 1.67-1.73 (m, 1H).

Compound 1-102 (600 MHz, DMSO-d$_6$): 7.79-7.81 (m, 3H), 7.67 (d, 2H), 7.44-7.50 (m, 3H), 7.03 (d, 1H), 4.64 (q, 2H), 4.12 (s, 3H), 3.31 (s, 3H), 2.45 (s, 3H).

Compound 1-1.54 (600 MHz, DMSO-d$_6$): 8.25 (s, 1H), 8.22 (d, 1H), 8.05 (d, 1 IT), 7.93 (d, 1H), 7.75-7.77 (m, 2H), 7.73 (s, 1H), 7.46-7.50 (m, 3H), 3.63 (s, 3H), 2.66 (s, 3H).

Compound 1-187 (600 MHz, CDCl$_3$): 8.29 (s, 1H), 7.91 (d, 1H), 7.70-7.74 (m, 2H), 7.30-7.37 (m, 5H), 6.44 (d, 1H), 4.39 (s, 3H), 3.23 (s, 3H).

Compound 1-296 (600 MHz, CDCl$_3$): 7.91 (s, 1H), 7.80 (d, 1H), 7.51-7.53 (m, 2H), 7.46 (t, 1H), 7.40-7.43 (m, 2H), 7.16 (d, 1H), 6.89 (d, 4.00-4.02 (m, 5H), 3.23 (s, 3H), 2.51 (s, 3H), 1.88-1.94 (m, 2H), 1.09 (t, 3H).

Compound 1-297 (600 MHz, CDCl$_3$): 7.92 (d, 1H), 7.84 (d, 1H), 7.53-7.55 (m, 2H), 7.45-7.48 (m, 1H), 7.40-7.43 (m, 2H), 7.11 (d, 1H), 6.96 (d, 1H), 4.83-4.87 (m, 1H), 4.00 (s, 3H), 3.20 (s, 3H), 2.51 (s, 3H), 1.33 (d, 6H).

Compound 1-298 (600 MHz, CDCl$_3$): 8.17 (d, 1H), 7.84 (d, 1H), 7.65 (d, 1H), 7.35 (d, 2H), 7.18 (d, 2H), 6.53 (d, 1H), 5.06 (s, 2H), 4.05 (s, 3H), 3.48 (s, 3H), 3.24 (s, 3H), 2.38 (s, 3H).

Compound 1-299 (600 MHz, CDCl$_3$): 8.18 (d, 1H), 7.84 (d, 1H), 7.66 (d, 1H), 7.47-7.49 (m, 2H), 7.09 (t, 2H), 6.58 (d, 1H), 5.06 (s, 2H), 4.06 (s, 3H), 3.48 (s, 3H), 3.24 (s, 3H).

Compound 1-300 (600 MHz, CDCl$_3$): 8.17-8.19 (m, 2H), 7.67 (d, 1H), 7.42 (d, 1H), 7.31-7.34 (m, 1H), 7.18-7.26 (m, 2H), 6.51 (d, 1H), 5.07 (s, 2H), 4.07 (s, 3H), 3.49 (s, 3H), 3.24 (s, 3H), 2.41 (s, 3H).

Compound 1-301 (600 MHz, CDCl$_3$): 8.17 (d, 1H), 8.04 (d, 1H), 7.65 (d, 1H), 7.34-7.40 (m, 2H), 6.88-6.94 (m, 2H), 6.66 (d, 1H), 5.07 (s, 2H), 4.06 (s, 3H), 3.81 (s, 3H), 3.48 (s, 3H), 3.24 (s, 3H).

Compound 1-302 (600 MHz, CDCl$_3$): 7.88 (d, 1H), 7.80 (d, 1H), 7.50-7.51 (m, 2H), 7.44-7.46 (m, 1H), 7.39-7.41 (m, 2H), 7.19 (d, 1H), 6.86 (d, 1H), 4.21 (t, 2H), 3.99 (s, 3H), 3.82 (t, 2H), 3.61 (q, 2H), 3.26 (s, 3H), 2.55 (s, 3H), 1.26 (t, 3H).

Compound 1-303 (600 MHz, CDCl$_3$): 8.18 (d, 1H), 7.97 (d, 1H), 7.66 (d, 1H), 7.39-7.46 (m, 2H), 7.14-7.19 (m, 1H), 7.06-7.12 (m, 1H), 6.70 (d, 1H), 5.06 (s, 2H), 4.05 (s, 3H), 3.47 (s, 3H), 3.24 (s, 3H).

Compound 1-304 (600 MHz, CDCl$_3$): 8.19-8.23 (m, 1H), 8.18 (d, 1H), 7.71 (d, 1H), 7.67 (d, 1H), 7.51-7.61 (m, 3H), 6.67 (d, 1H), 5.06 (s, 2H), 4.05 (s, 3H), 3.47 (s, 3H), 3.24 (s, 3H).

Compound 1-305 (600 MHz, CDCl$_3$): 8.27 (d, 1H), 8.17 (d, 1H), 7.66 (d, 1H), 7.50 (d, 1H), 7.42 (d, 1H), 7.33-7.38 (m, 1H), 7.26-7.30 (m, 1H), 6.67 (d, 1H), 5.06 (s, 2H), 4.05 (s, 3H), 3.47 (s, 3H), 3.24 (s, 3H).

Compound 1-306 (600 MHz, CDCl$_3$): 8.24 (d, 1H), 8.18 (d, 1H), 7.66 (d, 1H), 7.62 (d, 1H), 7.49 (d, 1H), 7.30-7.34 (m, 1H), 7.26-7.30 (m, 1H), 6.63 (d, 1H), 5.06 (s, 2H), 4.05 (s, 3H), 3.47 (s, 3H), 3.24 (s, 3H).

Compound 1-307 (600 MHz, CDCl$_3$): 8.18 (d, 1H), 7.84 (d, 1H), 7.67 (d, 1H), 7.26-7.29 (m, 4H), 6.57 (d, 1H), 5.06 (s, 2H), 4.05 (s, 3H), 3.47 (s, 3H), 3.24 (s, 3H), 2.35 (s, 3H).

Compound 1-308 (600 MHz, CDCl$_3$): 8.17 (d, 1H), 7.79 (d, 1H), 7.66 (d, 1H), 7.60 (d, 1H), 7.57 (d, 1H), 7.38-7.41 (m, 1H), 7.26-7.29 (m, 1H), 6.68 (d, 1H), 5.06 (s, 2H), 4.05 (s, 3H), 3.47 (s, 3H), 3.24 (s, 3H).

Compound 1-309 (600 MHz, CDCl$_3$): 8.17 (d, 1H), 7.79 (d, 1H), 7.67 (d, 1H), 7.38-7.46 (m, 2H), 7.30-7.36 (m, 2H), 6.68 (d, 1H), 5.06 (s, 2H), 4.05 (s, 3H), 3.47 (s, 3H), 3.24 (s, 3H).

Compound 1-310 (600 MHz, CDCl$_3$): 8.17 (d, 1H), 7.89 (d, 1H), 7.65-7.72 (m, 4H), 7.51-7.57 (m, 1H), 6.80 (d, 1H), 5.06 (s, 2H), 4.05 (s, 3H), 3.46 (s, 3H), 3.23 (s, 3H).

Compound 1-311 (600 MHz, CDCl$_3$): 8.18 (d, 1H), 7.82 (d, 1H), 7.66 (d, 1H), 7.34-7.40 (m, 1H), 726-7.28 (m, 1H), 7.12-7.18 (m, 2H), 6.65-6.69 (d, 1H), 5.06 (s, 2H), 4.05 (s, 3H), 3.46 (s, 3H), 3.23 (s, 3H).

Compound 1-312 (600 MHz, CDCl$_3$): 7.91 (d, 1H), 7.81 (d, 1H), 7.51-7.52 (m, 2H), 7.46-7.48 (m, 1H), 7.40-7.45 (m, 2H), 7.17 (d, 1H), 6.88 (d, 1H), 4.15 (t, 2H), 4.00 (s, 3H), 3.66 (t, 2H), 3.38 (s, 3H), 3.22 (s, 3H), 2.51 (s, 3H), 2.12-2.16 (m, 2H).

Compound 1-313 (600 MHz, CDCl$_3$): 7.92 (d, 1H), 7.90 (d, 7.79-7.81 (m, 2H), 7.51-7.52 (m, 1H), 7.41-7.46 (m, 2H), 7.16 (d, 1H), 6.88 (d, 1H), 4.07 (t, 2H), 4.00 (s, 3H), 3.47 (t, 2H), 3.36 (s, 3H), 3.22 (s, 3H), 2.51 (s, 3H), 1.93-1.96 (m, 2H), 1.78-1.80 (m, 2H).

Compound 1-314 (600 MHz, CDCl$_3$): 8.09 (d, 1H), 8.06 (d, 1H), 7.83 (d, 1H), 7.65-7.66 (m, 2H), 7.41-7.49 (m, 3H), 6.77 (d, 1H), 5.06 (s, 2H), 4.15 (s, 3H), 3.68 (t, 2H), 3.52 (t, 2H), 3.42 (q, 2H), 3.39 (s, 3H), 1.07 (t, 3H).

Compound 1-315 (600 MHz, CDCl$_3$): 8.00 (d, 1H), 7.87 (d, 1H), 7.43-7.50 (m, 4H), 7.36-7.42 (m, 2H), 6.63 (d, 1H), 4:33-4.42 (m, 2H), 4.04 (s, 3H), 3.78-3.84 (m, 2H), 3.45 (s, 3H), 3.29 (s, 3H).

Compound 1-316 (600 MHz, CDCl$_3$): 8.01 (d, 1H), 7.87 (d, 1H), 7.44-7.48 (m, 41-H), 7.38-7.41 (m, 2H), 6.63 (d, 1H), 4.39 (t, 2H), 4.05 (s, 3H), 3.86 (t, 2H), 3.62 (q, 2H), 3.31 (s, 3H), 1.25 (t, 3H).

Compound 1-317 (600 MHz, CDCl$_3$): 7.99 (d, 1H), 7.87 (d, 1H), 7.42-7.47 (m, 4H), 7.37-7.41 (m, 2H), 6.62 (d, 1H), 4.31 (t, 2H), 4.06 (s, 3H), 3.61 (t, 2H), 3.36 (s, 3H), 3.25 (s, 3H), 2.12-2.17 (m, 2H).

Compound 1-318 (600 MHz, CDCl$_3$): 7.98 (d, 1H), 7.87 (d, 1H), 7.37-7.48 (m, 6H), 6.62 (d, 1H), 4.17 (t, 2H), 4.05 (s, 3H), 3.24 (s, 3H), 1.91 (q, 2H), 1.06 (t, 3H).

Compound 1-319 (600 MHz, CDCl$_3$): 7.98 (d, 1H), 7.87 (d, 1H), 7.37-7.48 (m, 6H), 6.62 (d, 1H), 4.05 (d, 2H), 4.01 (s, 3H), 3.29 (s, 3H), 1.42. (ddd, 1H), 0.60-0.70 (m, 2H), 0.43 (dt, 2H).

Compound 2-7 (600 MHz, CDCl$_3$): 7.86 (d, 1H), 7.27 (d, 1H), 6.76-6.78 (m, 1H), 4.11 (q, 2H), 3.98 (s, 3H), 3.24 (s, 3H), 2.44 (s, 3H), 2.09-2.13 (m, 2H), 1.99-2.06 (m, 2H), 1.49 (t, 3H), 1.43-1.47 (m, 4H).

Compound 2-9 (600 MHz, CDCl$_3$): 7.84 (d, 1H), 7.25 (d, 1H), 6.61-6.63 (m, 1H), 4.11 (q, 2H), 3.97 (s, 3H), 3.25 (s, 3H), 2.46-2.48 (m, 2H), 2.45 (s, 3H), 2.34-2.40 (m, 2H), 1.83-1.88 (m, 2H), 1.48 (t, 3H), Compound 2-13 (600 MHz, CDCl$_3$): 7.90 (d, 1H), 7.37 (d, 1H), 6.76-6.77 (m, 1H), 4.48 (q, 2H), 3.98 (s, 3H), 3.26 (s, 3H), 2.49 (s, 3H), 2.12-2.16 (m, 2H), 205-2.09 (m, 2H), 1.47-1.55 (m, 4H).

Compound 2-15 (600 MHz, CDCl$_3$): 7.89 (d, 1H), 7.38 (d, 1H), 6.61-6.63 (m, 1H), 4.49 (q, 2H), 3.98 (s, 3H), 3.26 (s, 3H), 2.50 (s, 3H), 2.47-2.49 (m, 2H), 2.37-2.41 (m, 2H), 1.86-1.91 (m, 2H).

Compound 2-19 (600 MHz, CDCl$_3$): 7.88 (d, 1H), 7.29 (d, 1H), 6.78-6.80 (m, 1H), 4.24 (t, 2H), 3.99 (s, 3H), 3.81 (t, 2H), 3.48 (s, 3H), 3.29 (s, 3H). 2.50 (s, 3H), 2.01-2.16 (m, 4H), 1.33-1.53 (m, 4H).

Compound 2-21 (600 MHz, CDCl$_3$): 7.85 (d, 1H), 7.30 (d, 1H), 6.59-6.64 (m,1H), 4.19-4.25 (m, 2H), 3.97 (s, 3H), 3.78-3.83 (m, 2H), 3.47 (s, 3H), 3.28 (s, 3H), 2.48 (s, 3H), 2.43-2.48 (m, 2H), 2.31-2.40 (m, 2H), 1.80-1.90 (m, 2H).

Compound 2-37 (600 MHz, CDCl$_3$): 8.06 (d, 1H), 7.61 (d, 1H), 6.79-6.82 (m, 1H), 4.61 (t, 2H), 4.01 (s, 3H), 3.36

(brs, 2H), 3.19 (s, 3H), 2.44 (s, 3H), 2.13-2.15 (m, 2H), 2.02-2.04 (m, 2H), 1.48-1.54 (m, 4H).

Compound 2-43 (600 MHz, CDCl$_3$): 7.98 (d, 1H), 7.37 (d, 1H), 6.77-6.78 (m, 1H), 3.99 (s, 3H), 3.10 (s, 3H), 2.69 (s, 3H), 2.44 (s, 3H), 2.12-2.13 (m, 2H), 2.00-2.01 (m, 2H), 1.46-1.47 (m, 4H).

Compound 2-55 (600 MHz, CDCl$_3$): 7.99 (d, 1H), 7.43 (d, 1H), 6.74 (d, 11-H), 4.07 (s, 3H), 4.03 (s, 3H), 3.25 (s, 3H), 2.10-2.15 (m, 2H), 1.96-2.00 (m, 2H), 1.47 (q, 4H).

Compound 2-61 (600 MHz, CDCl$_3$): 7.96 (d, 1H), 7.40 (d, 1H), 6.72 (d, 1H), 4.27 (q, 2H), 4.01 (s, 3H), 3.24 (s, 3H), 2.07-2.12 (m, 2H), 1.96-2.00 (m, 2H), 1.48 (t, 3H), 1.44 (qd, 4H).

Compound 2-97 (6001\i1Hz, CDCl$_3$): 8.13 (d, 1H), 7.55 (d, 1H), 6.74 (s, 1H), 4.06 (s, 3H), 3.15 (s, 3H), 2.81 (s, 3H), 2.11-2.12 (m, 2H), 2.01-2.02 (m, 2H), 1.46-1.48 (m, 1H).

Compound 2-103 (600 MHz, CDCl$_3$): 8.18 (d, 1H), 7.68 (d, 1H), 6.75 (s, 1H), 5.08 (s, 2H), 4.06 (s, 3H), 3.51 (s, 3H), 3.26 (s, 3H), 2.11-2.12 (m, 2H), 1.99-2.00 (m, 2H), 1.44-1.46 (m, 4H).

Compound 2-104 (600 MHz, CDCl$_3$): 8.16 (d, 1H), 7.58 (d, 1H), 5.61-5.69 (m, 2H), 5.05 (s, 2H), 4.03 (s, 3H), 3.48 (s, 3H), 3.24 (s, 3H), 2.84-2.89 (m, 1H), 1.99-2.32 (m, 5H), 1.66-1.73 (m, 1H).

Compound 2-105 (600 MHz, CDCl$_3$): 8.20 (d, 1H), 7.68 (d, 1H), 6.51-6.54 (m, 1H), 5.0$ (s, 2H), 406 (s, 3H), 3.50 (s, 3H), 3.26 (s, 3H), 2.43-2.46 (m, 2H), 2.29-2.32 (m, 2H), 1.83-1.88 (m, 2H).

Compound 2-106 (600 MHz, CDCl$_3$): 8.17 (d, 1H), 7.58 (d, 1H), 5.61 (s, 2H), 5.06 (s, 2H), 4.05 (s, 3H), 3.46-3.51 (m, 4H), 3.25 (s, 3H), 2.69-2.72 (m, 2H), 2.52-2.57 (m, 2H).

Compound 2-235 (600 MHz, DMSO-d$_6$): 8.09 (d, 1H), 7.93 (d, 1H), 6.82-680 (m,1H), 4.95 (s, 2H), 4.45 (s, 3H), 3.40 (s, 3H), 3.36 (s, 3H), 2.10-2.06 (m, 2H), 1.92-1.86 (m, 2H), 1.36-1.28 (m, 4H).

Compound 2-237 (600 MHz, DMSO-d$_6$): 8.07 (d, 1H), 7.94 (d, 1H), 6.66-6.63 (m,1H), 4.95 (s, 2H), 4.44 (s, 3H), 3.40 (s, 3H), 3.36 (s, 3H), 2.40-2.36 (m, 2H), 2.25-2.21 (m, 2H), 1.72-1.67 (m, 2H).

Compound 2-265 (600 MHz, DMSO-d$_6$): 8.38 (s, 1H), 8.32 (d, 1H), 8.27 (d, 1H), 6.72 (s, 1H), 4.15 (s, 3H), 3.40 (s, 3H), 1.92-1.99 (m, 4H), 1.31-1.35 (m, 4H).

Compound 2-266 (600 MHz, DMSO-d$_6$): 8.38 (s, 1H), 8.29 (d, 1H), 8.25 (d, 1H), 6.48 (s, 1H), 4.16 (s, 3H), 3.38 (s, 3H), 2.33-2.35 (m, 2H), 2.13-2.21 (m, 2H), 1.69-1.74 (m, 2H).

Compound 2-267 (600 MHz, CDCl$_3$): 8.16 (d, 1H), 7.76 (dd, 1H), 7.56 (d, 1H), 6.45 (t, 1H), 4.18 (s, 3H), 1.99-2.02 (m, 4H), 1.47-1.50 (m, 2H), 1.41-1.44 (m, 2H).

Compound 2-268 (600 MHz, CDCl$_3$): 7.48 (d, 1H), 7.43 (d, 1H), 7.36 (dd, 1H), 6.73 (t, 1H), 3.98 (s, 3H), 2.09-2.10 (m, 2H), 2.01-2.02 (m, 2H), 1.43-1.47 (m, 4H).

Compound 2-269 (600 MHz, CDCl$_3$): 8.02 (s, 1H), 7.97 (d, 1H), 7.77 (d, 1H), 6.73 (s, 1H), 4.05 (s, 3H), 3.12 (s, 3H), 2.12-2.13 (m, 2H), 2.03-2.04 (m, 2H), 1.49-1.50 (m, 4H).

Compound 2-270 (600 MHz, CDCl$_3$): 8.14 (d, 1H), 7.63 (d, 1H), 6.71 (t, 1H), 5.13 (s, 2H), 4.02 (s, 3H), 3.75 (t, 2H), 3.53 (t, 2H), 3.30 (s, 3H), 3.27 (s, 3H), 2.06-2.07 (m, 2H), 1.94-1.96 (m, 2H), 1.39-1.40 (m, 4H).

Compound 2-271 (600 MHz, CDCl$_3$): 8.27 (d, 1H), 8.24 (dd, 1H), 7.74 (d, 1H), 6.70 (t, 1H), 4.03 (s, 3H), 2.11-2.12 (m, 2H), 2.01-2.02 (m, 2H), 1.45-1.51 (m, 4H).

Compound 2-274 (600 MHz, CDCl$_3$): 7.86 (d, 1H), 7.28 (d, 1H), 6.74-6.79 (m, 1H), 419-4.25 (m, 2H), 3.98 (s, 3H), 3.80-3.85 (m, 2H), 3.56-3.65 (m, 2H), 3.28 (s, 3H), 2.48 (s, 3H), 2.08-2.16 (m, 2H), 1.98-2.07 (m, 2H), 1.41-1.49 (m, 4H), 1.17-1.26 (m, 3H).

Compound 2-275 (600 MHz, CDCl$_3$): 7.85 (d, 1H), 7.29 (d, 1H), 6.60-6.64 (m, 1H), 4.20-4.25 (m, 2H), 3.97 (s, 3H), 3.8-3.85 (m, 2H), 3.57-3.65 (m, 2H), 3.29 (s, 3H), 2.49 (s, 3H), 2.44-2.48 (m, 2H), 2.35-2.40 (m, 2H), 1.80-1.90 (m, 2H), 1.18-1.28 (m, 3H).

Compound 2-276 (600 MHz, CDCl$_3$): 8.06 (s, 1H), 7.68-7.69 (m, 1H), 7.63-7.64 (m, 1H), 6.83 (s, 1H), 4.07 (s, 3H), 3.24 (s, 3H), 2.04-2.13 (m, 4H), 1.41-1.51 (m, 4H).

Compound 2-277 (600 MHz, CDCl$_3$): 7.82 (d, 1H), 7.25 (d, 1H), 6.61-6.64 (m, 1H), 4.00-4.04 (m, 2H), 3.97 (s, 3H), 3.20 (s, 3H), 2.46-2.50 (m, 2H), 2.45 (s, 3H), 1.84-1.92 (m, 4H), 1.59-1.63 (m, 2H), 1.07 (t, 3H).

Compound 2-278 (600 MHz, CDCl$_3$): 7.84 (d, 1H), 7.25 (d, 1H), 6.76-6.77 (m, 1H), 4.01-4.03 (m, 2H), 3.98 (s, 3H), 3.24 (s, 1H), 2.44 (s, 3H), 2.10-2.16 (m, 2H), 2.00-2.06 (m, 2H), 1.84-1.94 (m, 2H), 1.43-1.51 (m, 4H), 1.08 (t, 3H).

Compound 2-279 (600 MHz, CDCl$_3$): 8.11 (d, 1H), 8.08 (d, 1H), 686-687 (m, 1H), 5.00 (s, 2H), 4.12 (s, 3H), 3.54 (t, 2H), 3.89 (s, 3H), 2.03-2.04 (m, 2H), 1.89-1.90 (m, 2H), 1.56-1.57 (m, 2H), 1.28-1.30 (m, 4H), 0.88 (t, 3H).

Compound 2-280 (600 MHz, CDCl$_3$): 8.01 (d, 1H), 7.44 (d, 1H), 6.71-6.73 (m, 1H), 4.39 (t, 2H), 4.03 (s, 3H), 3.87 (t, 2H), 3.62 (q, 2H), 3.31 (s, 3H), 2.12-2.14 (m, 2H), 2.02-2.04 (m, 2H), 1.49-1.52 (m, 4H), 1.25 (t, 3H).

Compound 2-281 (600 MHz, CDCl$_3$): 7.99 (d, 1H), 7.42 (d, 1H), 6.73-6.75 (m, 1H), 4.33 (t, 2H), 4.03 (s, 3H), 3.61 (t, 2H), 3.37 (s, 3H), 3.26 (s, 3H), 2.15-2.19 (m, 2H), 2.13-2.15 (m, 2H), 2.02-2.04 (m, 2H), 1.48-1.52 (m, 4H).

Compound 2-282 (600 MHz, CDCl$_3$): 7.94 (d, 1H), 7.39 (d, 1H), 6.70 (q, 1H), 4.05 (qt, 2H), 3.99 (s, 3H), 3.22 (s, 3H), 2.04-2.11 (m, 2H), 1.96-2.00 (m, 2H), 1.81-1.93 (m, 2H), 1.44 (qd, 4H), 1.03 (tt, 3H).

Compound 2-283 (600 MHz, CDCl$_3$): 7.97 (d, 1H), 7.40 (d, 1H), 6.72 (tt, 1H), 4.05 (d, 2H), 4.01 (s, 3H), 3.29 (s, 3H), 2.08-2.13 (m, 2H), 2.00 (t, 2H), 1.38-1.49 (m, 5H), 0.61-0.68 (m, 2H), 0.43 (dt, 2H).

Compound 3-217 (600 MHz, CDCl$_3$): 8.09 (d, 1H), 7.91 (d, 1H), 7.77 (d, 1H), 7.43-7.50 (m, 3H), 7.35-7.42 (m, 2H), 6.51 (d, 1H), 4.07 (s, 3H).

Compound 3-218 (600 MHz, CDCl$_3$): 8.65 (d, 1H), 7.96-8.01 (m, 1H), 7.92 (d, 1H), 7.37-7.53 (m, 6H), 6.61 (d, 1H), 3.98 (s, 3H).

Compound 3-219 (600 MHz, CDCl$_3$): 8.23-8.27 (m, 1H), 7.92 (d, 1H), 7.84 (d, 1H), 7.49-7.53 (m, 2H), 7.37-7.47 (m, 3H), 6.76 (d, 1H), 4.03 (s, 3H), 2.56 (s, 3H).

Compound 3-220 (600 MHz, CDCl$_3$): 8.86 (d, 1H), 8.76-8.79 (m, 1H), 8.04 (d, 1H), 7.92 (d, 1H), 7.48-7.53 (m, 2H), 7.37-7.47 (m, 1H), 6.71 (d, 1H), 4.00 (s, 3H).

Compound 4-248 (600 MHz, CDCl$_3$): 8.10 (d, 1H), 7.79 (d, 1H), 6.62-6.65 (m, 1H), 4.06 (s, 3H), 2.10-2.15 (m, 2H), 2.02-2.08 (m, 2H), 1.58-1.70 (m, 2H), 1.49-1.52 (m, 2H).

Compound 4-249 (600 MHz, CDCl$_3$): 8.11 (d, 1H), 7.80 (d, 1H), 6.50-6.52. (m, 1H), 4.06 (s, 3H), 2.42-2.49 (m, 2H), 2.24-2.32 (m, 2H), 1.84-1.93 (m, 2H).

BIOMETRIC TEST EXAMPLES

Embodiment 4 Determination of Herbicidal Activity

Seeds of broadleaf weeds (zinnia and piemarker) or grassy weeds (green bristlegrass and barnyard grass) are respectively sown in a paper cup having a diameter of 7 cm and containing nutrient soil; after sowing, the seeds are covered with 1 cm of soil; the soil is pressed and watered, and then the seeds are cultivated in a greenhouse according to a conventional method; and stems and leaves are sprayed after 2-3 leaf stage of the weeds.

After the original medicinal acetone was dissolved, the test requires to use 1% of Tween 80 to stand in running water to prepare the solution to be tested with a required concentration. According to the design dose of the test, spray treatment was carried out on a track-type crop sprayer (designed and produced by British Engineer Research Ltd.) (spray pressure is 1.95 kg/cm$^2$, spray volume is 50 L/hm$^2$ and track speed is 1.48 km/h). The test was repeated for three times. The test material was treated and then placed in an operation hall. The medicinal liquid was naturally dried in the shade, and then was placed in a greenhouse and managed according to the conventional method, The response of the weeds to the drug was observed and recorded, After treatment, the control effects of the test drug on the weeds were visually inspected regularly, expressed by 0-100%. "0" represents no control effect and "100%" represents complete killing.

The test results show that the compounds of the formula I generally have high control effects on various weeds, Part of the test compounds, such as compounds 1-1, 1-8, 1-15, 1-17, 1-19, 1-24, 1-41, 1-53, 1-95, 1-100, 1-296, 2-7, 2-9, 2-13, 2-15, 2-19, 2-43, 2-97, 2-103, 2-104, 2-105, 2-106, 2-115, 2-265, 2-266, 2-267, 2-268, 2-269 and 2-270, have good control effects on zinnia, piemarker, green bristlegrass or barnyard grass at the application dose of 600 g a.i./hm$^2$, and the control effects are greater than or equal to 90%.

According to the above test method, part of the compounds of the formula I and KC are selected for activity test of controlling the zinnia. The results are shown in Table 5.

TABLE 5

Zinnia Control Activity of Part of Compounds of Formula I and Reference Compound KC
(after emergence, control effect %)

| Compound | dose g a.i./hm$^2$ | | |
|---|---|---|---|
| | 600 | 150 | 37.5 |
| 1-1 | 100 | 100 | 100 |
| 1-8 | 100 | 95 | 90 |
| 1-19 | 100 | 95 | 95 |
| 1-24 | 100 | 100 | 100 |
| 1-95 | 100 | 100 | 100 |
| 2-13 | 100 | 100 | 100 |
| 2-15 | 100 | 100 | 100 |
| 2-97 | 100 | 100 | 100 |
| 2-103 | 100 | 95 | 90 |
| 2-106 | 100 | 100 | 100 |
| 2-265 | 100 | 100 | 95 |
| 2-266 | 100 | 98 | 95 |
| KC | / | 90 | 65 |

"/" in the table indicates no test.

According to the above test method, part of the compounds of the formula I and KC are selected for activity test of controlling the piemarker. The results are shown in Table 6.

TABLE 6

Piemarker Control Activity of Part of Compounds of Formula I and Reference Compound KC
(after emergence, control effect %)

| Compound | dose g a.i./hm2 | | |
|---|---|---|---|
| | 600 | 150 | 37.5 |
| 1-1 | 100 | 100 | 100 |
| 1-8 | 100 | 100 | 100 |

TABLE 6-continued

Piemarker Control Activity of Part of Compounds of Formula I and Reference Compound KC
(after emergence, control effect %)

| Compound | dose g a.i./hm2 | | |
|---|---|---|---|
| | 600 | 150 | 37.5 |
| 1-19 | 98 | 90 | 90 |
| 1-24 | 100 | 100 | 100 |
| 2-97 | 100 | 100 | 95 |
| 2-103 | 100 | 100 | 95 |
| 2-265 | 95 | 95 | 90 |
| 2-266 | 100 | 95 | 90 |
| 2-269 | 100 | 95 | 90 |
| 2-270 | 100 | 98 | 90 |
| KC | / | 85 | 60 |

"/" in the table indicates no test.

At the same time, part of compounds of the formula I are further subjected to the activity test of controlling piemarker in a smaller dose. Namely, under the dose of 18.75 g a.i./hm$^2$, the compounds have obvious effects, wherein the control effects of 1-1, 1-8, 1-19, 1-24, 2-103, 2-265 and 2-266 are greater than or equal to 70%. The control effects of 2-265 and 2-266 can reach 90%.

According to the above test method, part of the compounds of the formula I and KC are selected for the activity test of controlling the green bristlegrass. The results are shown in Table 7.

TABLE 7

Green Bristlegrass Control Activity of Part of Compounds of Formula I and Reference Compound KC
(after emergence, control effect %)

| Compound | dose g a.i./hm2 | | |
|---|---|---|---|
| | 600 | 150 | 37.5 |
| 2-15 | 100 | 100 | 90 |
| 2-97 | 100 | 95 | 80 |
| 2-103 | 95 | 90 | 80 |
| 2-265 | 95 | 90 | 80 |
| 2-266 | 100 | 95 | 90 |
| 2-270 | 98 | 95 | 90 |
| KC | / | 70 | 45 |

"/" in the table indicates no test.

According to the above test method, part of the compounds of the formula I and KC are selected for the activity test of controlling the barnyard grass. The results are shown in Table 8.

TABLE 8

Barnyard Grass Control Activity of Part of Compounds of Formula I and Reference Compound KC
(after emergence, control effect %)

| Compound | dose g a.i./hm2 | | |
|---|---|---|---|
| | 600 | 150 | 37.5 |
| 1-24 | 100 | 95 | 95 |
| 1-100 | 100 | 100 | 100 |
| 1-296 | 100 | 100 | 100 |
| 2-13 | 100 | 100 | 80 |
| 2-15 | 100 | 100 | 85 |
| 2-19 | 100 | 100 | 90 |
| 2-97 | 100 | 95 | 90 |
| 2-103 | 100 | 90 | 80 |

TABLE 8-continued

Barnyard Grass Control Activity of Part of Compounds of Formula I
and Reference Compound KC
(after emergence, control effect %)

| Compound | dose g a.i./hm2 | | |
|---|---|---|---|
| | 600 | 150 | 37.5 |
| 2-105 | 100 | 90 | 90 |
| 2-265 | 95 | 95 | 95 |
| 2-266 | 95 | 90 | 85 |
| 2-269 | 95 | 90 | 80 |
| 2-270 | 100 | 95 | 90 |
| KC | / | 65 | 50 |

"/" in the table indicates no test.

To sum up, the alkene-containing amide compound of the present invention has excellent herbicidal activity, also has high herbicidal activity at a lower dosage, and can be used for agriculturally controlling various weeds.

The invention claimed is:

1. An alkene-containing amide compound of formula I, a stereoisomer of the compound, and/or an agriculturally acceptable salt thereof,

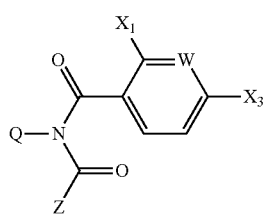

I wherein:
X$_1$ and X$_3$ are independently selected from halogen, C$_1$-C$_6$ alkylsulfonyl, C$_1$-C$_6$ alkyl, and C$_1$-C$_6$ haloalkyl;
W is CX$_2$, X$_2$ being hydrogen, Y$_1$ oxy, Y$_1$ oxy C$_1$-C$_6$ alkyl, Y$_1$ sulfonyl C$_1$-C$_6$ alkyl, 5-7 membered aliphatic heterocycle containing 1-4 heteroatoms, 5-7 membered aromatic heterocycle containing 1-4 heteroatoms, 5-7 membered aliphatic heterocyclic C$_1$-C$_6$ alkyl containing 1-4 heteroatoms, or 5-7 membered aromatic heterocyclic C$_1$-C$_6$ alkyl containing 1-4 heteroatoms,
wherein hydrogen on 5-7 membered aliphatic heterocycle containing 1-4 heteroatoms or the 5-7 membered aromatic heterocycle containing 1-4 heteroatoms is unsubstituted or substituted by one or more substituents selected from nitro, halogen, C$_1$-C$_6$ alkyl, C$_1$-C$_6$ haloalkyl, C$_1$-C$_6$ alkoxy, C$_1$-C$_6$ haloalkoxy, C$_3$-C$_6$ cycloalkyl, C$_3$-C$_6$ cycloalkoxy, C$_2$-C$_6$ alkenyl, C$_2$-C$_6$ alkynyl, phenyl, and halophenyl;
Y$_1$ is selected from C$_1$-C$_6$ alkyl, C$_1$-C$_6$ haloalkyl, C$_3$-C$_6$ cycloalkyl, C$_3$-C$_6$ cycloalkyl C$_1$-C$_6$ alkyl, C$_1$-C$_6$ alkoxy C$_1$-C$_6$ alkyl, phenyl, 5-7 membered aliphatic heterocycle containing 1-4 heteroatoms, 5-7 membered aromatic heterocycle containing 1-4 heteroatoms, 5-7 membered aliphatic heterocyclic C$_1$-C$_6$ alkyl containing 1-4 heteroatoms, and 5-7 membered aromatic heterocyclic C$_1$-C$_6$ alkyl containing 1-4 heteroatoms, wherein hydrogen on the phenyl, the 5-7 membered aliphatic heterocycle containing 1-4 heteroatoms, and the 5-7 membered the aromatic heterocycle containing 1-4 heteroatoms is unsubstituted or substituted by one or more substituents selected from nitro, halogen, C$_1$-C$_6$ alkyl, C$_1$-C$_6$ haloalkyl, C$_1$-C$_6$ alkoxy, C$_1$-C$_6$ haloalkoxy, C$_3$-C$_6$ cycloalkyl, C$_3$-C$_6$ cycloalkoxy, C$_2$-C$_6$ alkenyl, C$_2$-C$_6$ alkynyl, phenyl, and halophenyl;
Z is Z$_1$ or Z$_2$;

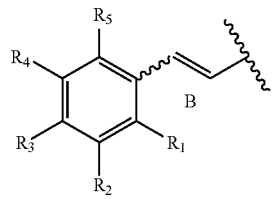

Z$_1$

Z$_2$ is C$_3$-C$_8$ cycloalkenyl that is unsubstituted or having hydrogen on the ring thereof substituted by one or more substituents selected from nitro, halogen, C$_1$-C$_6$ alkyl, C$_1$-C$_6$ haloalkyl, C$_1$-C$_6$ alkoxy, C$_1$-C$_6$ haloalkoxy, C$_1$-C$_6$ alkenyl, and C$_3$-C$_6$ cycloalkyl;
Q is Q$_2$, or Q$_6$ group;

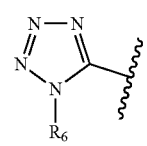

Q$_1$

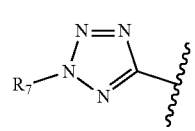

Q$_2$

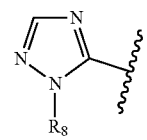

Q$_3$

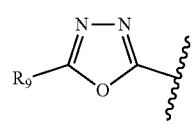

Q$_4$

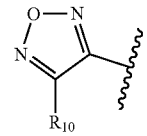

Q$_5$

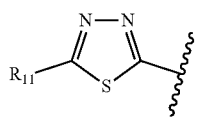

Q$_6$

B represents the carbon-carbon double bond, and the stereoisomer of the compound is a cis-stereoisomer in which hydrogen atoms are on a same side of the carbon-carbon double bond B or a trans-stereoisomer in which hydrogen atoms are on both sides of the carbon-carbon double bond B;
R$_1$ to R$_5$ are independently selected from hydrogen, hydroxyl, cyano, nitro, halogen, phenyl, C$_1$-C$_6$ alkyl, C$_1$-C$_6$ haloalkyl, C$_2$-C$_6$ alkenyl, C$_2$-C$_6$ haloalkenyl, $C_2$-$C_6$ alkynyl, $C_2$-$C_6$ haloalkynyl, $C_1$-$C_6$ alkoxy, $C_1$-$C_6$ haloalkoxy, $C_1$-$C_6$ alkylthio, and benzyloxy, wherein $R_1$ and $R_2$ form a benzene ring, a 5-7 membered aliphatic heterocycle containing 1-4 heteroatoms or a 5-7 membered aromatic heterocycle containing 1-4 heteroatoms together with the carbon atoms on the connected benzene ring;

$R_2$ and $R_3$ form a benzene ring, a 5-7 membered aliphatic heterocycle containing 1-4 heteroatoms or a 5-7 membered aromatic heterocycle containing 1-4 heteroatoms together with the carbon atoms on the connected benzene ring;

$R_7$ is hydrogen, $C_1$-$C_6$ alkyl, $C_1$-$C_6$ haloalkyl, $C_3$-$C_6$ cycloalkyl, $C_3$-$C_6$ cycloalkyl $C_1$-$C_6$ alkyl, $C_2$-$C_6$ alkenyl, $C_2$-$C_6$ alkynyl, or phenyl; and $R_{11}$ is selected from hydrogen, halogen, cyano, nitro, $C_1$-$C_6$ alkylsulfonyl, $C_1$-$C_6$ haloalkylsulfonyl, $C_1$-$C_6$ alkylsulfinyl, $C_1$-$C_6$ haloalkylsulfinyl, $C_1$-$C_6$ alkylthio, $C_1$-$C_6$ haloalkylthio, $C_1$-$C_6$ alkyl, $C_1$-$C_6$ haloalkyl, $C_1$-$C_6$ alkoxy, $C_1$-$C_6$ haloalkoxy, $C_1$-$C_3$ alkoxy $C_1$-$C_3$ alkyl, $C_1$-$C_6$ alkoxy $C_1$-$C_3$ alkoxy, $C_1$-$C_6$ alkoxy $C_1$-$C_3$ alkoxy $C_1$-$C_3$ alkyl, $C_3$-$C_6$ cycloalkyl, $C_3$-$C_6$ cycloalkyl $C_1$-$C_3$ alkyl, $C_3$-$C_6$ cycloalkyl $C_1$-$C_3$ alkoxy, and $C_3$-$C_6$ cycloalkyloxy.

2. The alkene-containing amide compound according to claim 1, the stereoisomer of the compound, and/or the agriculturally acceptable salt thereof, wherein:

$X_1$ and $X_3$ are independently selected from halogen, $C_1$-$C_6$ alkylsulfonyl, $C_1$-$C_6$ alkyl, and $C_1$-$C_6$ haloalkyl;

W is $CX_2$, $X_2$ being $Y_1$ oxy or $Y_1$ oxy $C_1$-$C_6$ alkyl;

$Y_1$ is selected from $C_1$-$C_6$ alkyl, $C_1$-$C_6$ haloalkyl, $C_3$-$C_6$ cycloalkyl, $C_3$-$C_6$ cycloalkyl $C_1$-$C_6$ alkyl, $C_1$-$C_6$ alkoxy $C_1$-$C_6$ alkyl, phenyl, a 5-7 membered aliphatic heterocycle containing 1-4 heteroatoms, a 5-7 membered aromatic heterocycle containing 1-4 heteroatoms, a 5-7 membered aliphatic heterocyclic $C_1$-$C_6$ alkyl containing 1-4 heteroatoms, and a 5-7 membered aromatic heterocyclic $C_1$-$C_6$ alkyl containing 1-4 heteroatoms, wherein the hydrogen on the phenyl, the 5-7 membered aliphatic heterocycle containing 1-4 heteroatoms or the 5-7 membered aromatic heterocycle containing 1-4 heteroatoms is unsubstituted or substituted by one or more substituents selected from nitro, halogen, $C_1$-$C_6$ alkyl, $C_1$-$C_6$ haloalkyl, $C_1$-$C_6$ alkoxy, $C_1$-$C_6$ haloalkoxy, $C_3$-$C_6$ cycloalkyl, and $C_3$-$C_6$ cycloalkoxy;

Z is the stereoisomer of $Z_1$ or $Z_2$;

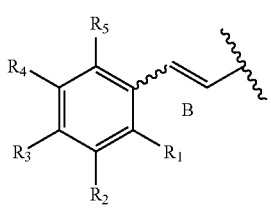

$Z_2$ is $C_3$-$C_8$ cycloalkenyl that is unsubstituted or having hydrogen on the ring thereof substituted by one or more substituents from nitro, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkenyl, and $C_3$-$C_6$ cycloalkyl;

$R_1$ to $R_5$ are independently selected from hydrogen, hydroxyl, cyano, nitro, halogen, phenyl, $C_1$-$C_6$ alkyl, $C_2$-$C_6$ alkenyl, $C_2$-$C_6$ alkynyl, $C_1$-$C_6$ alkoxy, $C_1$-$C_6$ alkylthio, and benzyloxy;

$R_7$ is hydrogen, $C_1$-$C_6$ alkyl, $C_3$-$C_6$ cycloalkyl, $C_2$-$C_6$ alkenyl, $C_2$-$C_6$ alkynyl, or phenyl; and $R_{11}$ is hydrogen, halogen, $C_1$-$C_6$ alkylthio, $C_1$-$C_6$ alkyl, $C_1$-$C_6$ alkoxy, $C_1$-$C_3$ alkoxy $C_1$-$C_3$ alkyl, $C_1$-$C_6$ alkoxy $C_1$-$C_3$ alkoxy, $C_1$-$C_6$ alkoxy $C_1$-$C_3$ alkoxy $C_1$-$C_3$ alkyl, or $C_3$-$C_6$ cycloalkyl.

3. The alkene-containing amide compound according to claim 2, the stereoisomer of the compound, and/or the agriculturally acceptable salt thereof, wherein:

$X_1$ and $X_3$ are independently selected from halogen, $C_1$-$C_3$ alkylsulfonyl, $C_1$-$C_3$ alkyl, and $C_1$-$C_3$ haloalkyl;

W is selected from $CX_2$, $X_2$ being $Y_1$ oxy or $Y_1$ oxy $C_1$-$C_3$ alkyl;

Z is from the stereoisomer of $Z_1$ or $Z_2$;

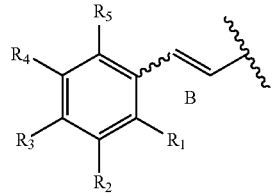

$Z_2$ is $C_5$-$C_6$ cycloalkenyl that is unsubstituted of having hydrogen on the ring thereof substituted by one or more substituents selected from $C_1$-$C_6$ alkyl, $C_1$-$C_6$ alkoxy, and $C_1$-$C_6$ alkenyl;

$R_1$ to $R_5$ are independently selected from hydrogen, hydroxyl, cyano, nitro, halogen, phenyl, $C_1$-$C_6$ alkyl, $C_2$-$C_6$ alkenyl, $C_2$-$C_6$ alkynyl, $C_1$-$C_6$ alkoxy, and benzyloxy, $R_7$ is hydrogen, $C_1$-$C_6$ alkyl, $C_2$-$C_6$ alkenyl, or phenyl; and $R_{11}$ is hydrogen, halogen, $C_1$-$C_6$ alkyl, $C_1$-$C_6$ alkoxy, $C_1$-$C_3$ alkoxy $C_1$-$C_3$ alkyl, $C_1$-$C_6$ alkoxy $C_1$-$C_3$ alkoxy, or $C_3$-$C_6$ cycloalkyl.

4. The alkene-containing amide compound according to claim 3, the stereoisomer of the compound, and/or the agriculturally acceptable salt thereof, wherein:

$X_1$ and $X_3$ are independently selected from halogen, $C_1$-$C_3$ alkylsulfonyl, and $C_1$-$C_3$ alkyl;

Z is the trans-isomer of $Z_1$ or $Z_2$;

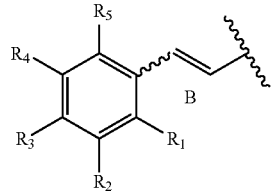

$Z_2$ is $G_1$, $G_2$, $G_3$, or $G_4$;

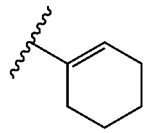

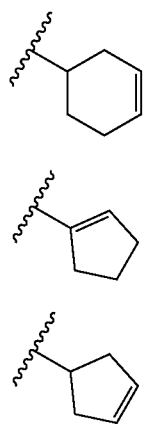

R₁ to R₅ are independently selected from hydrogen, hydroxyl, cyano, nitro, halogen, phenyl, methyl, ethyl, propyl, vinyl, propenyl, ethynyl, propynyl, methoxy, ethoxyl, benzyloxy, trifluoromethyl, and trifluoromethoxy;

R₇ is hydrogen, methyl, or ethyl; and

R₁₁ is hydrogen, chlorine or methyl.

5. A herbicidal composition, comprising an active ingredient and an agriculturally acceptable carrier, wherein the active ingredient is selected from the alkene-containing amide compound of claim 1, the stereoisomer thereof, and the agriculturally acceptable salt thereof, and a weight percentage of the active ingredient in the herbicidal composition is 1-99%.

6. A method for treating weeds, comprising: applying an effective dose of the herbicidal composition of claim 5 to a weed or a growth medium or site of the weed, wherein the weed is one or more selected from zinnia, piemarker, green bristlegrass, barnyard grass, and *Veronica persica*.

7. The method of claim 6, wherein the effective dose is 600 g a.i./hm².

8. An alkene-containing amide compound of formula I, a stereoisomer of the compound, and/or an agriculturally acceptable salt thereof,

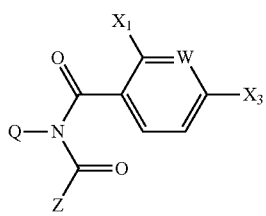

wherein:

$X_1$ and $X_3$ are independently selected from halogen, $C_1$-$C_6$ alkylsulfonyl, $C_1$-$C_6$ alkyl, and C1-$C_6$ haloalkyl;

W is $CX_2$, $X_2$ being hydrogen, $Y_1$ oxy, $Y_1$ oxy $C_1$-$C_6$ alkyl, $Y_1$ sulfonyl $C_1$-$C_6$ alkyl, 5-7 membered aliphatic heterocycle containing 1-4 heteroatoms, 5-7 membered aromatic heterocycle containing 1-4 heteroatoms, 5-7 membered aliphatic heterocyclic $C_1$-$C_6$ alkyl containing 1-4 heteroatoms, or 5-7 membered aromatic heterocyclic $C_1$-$C_6$ alkyl containing 1-4 heteroatoms, wherein hydrogen on 5-7 membered aliphatic heterocycle containing 1-4 heteroatoms or the 5-7 membered aromatic heterocycle containing 1-4 heteroatoms is unsubstituted or substituted by one or more substituents selected from nitro, halogen, $C_1$-$C_6$ alkyl, C1-$C_6$ haloalkyl, $C_1$-$C_6$ alkoxy, $C_1$-$C_6$ haloalkoxy, $C_3$-$C_6$ cycloalkyl, $C_3$-$C_6$ cycloalkoxy, $C_2$-$C_6$ alkenyl, $C_2$-$C_6$ alkynyl, phenyl, and halophenyl;

$Y_1$ is selected from $C_1$-$C_6$ alkyl, $C_1$-$C_6$ haloalkyl, $C_3$-$C_6$ cycloalkyl, $C_3$-$C_6$ cycloalkyl $C_1$-$C_6$ alkyl, $C_1$-$C_6$ alkoxy $C_1$-$C_6$ alkyl, phenyl, 5-7 membered aliphatic heterocycle containing 1-4 heteroatoms, 5-7 membered aromatic heterocycle containing 1-4 heteroatoms, 5-7 membered aliphatic heterocyclic $C_1$-$C_6$ alkyl containing 1-4 heteroatoms, and 5-7 membered aromatic heterocyclic $C_1$-$C_6$ alkyl containing 1-4 heteroatoms, wherein hydrogen on the phenyl, the 5-7 membered aliphatic heterocycle containing 1-4 heteroatoms, and the 5-7 membered the aromatic heterocycle containing 1-4 heteroatoms is unsubstituted or substituted by one or more substituents selected from nitro, halogen, $C_1$-$C_6$ alkyl, $C_1$-$C_6$ haloalkyl, $C_1$-$C_6$ alkoxy, $C_1$-$C_6$ haloalkoxy, $C_3$-$C_6$ cycloalkyl, $C_3$-$C_6$ cycloalkoxy, $C_2$-$C_6$ alkenyl, $C_2$-$C_6$ alkynyl, phenyl, and halophenyl;

Z is $Z_2$, and $Z_2$ is $C_3$-$C_8$ cycloalkenyl that is unsubstituted or having hydrogen on the ring thereof substituted by one or more substituents selected from nitro, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkenyl, and $C_3$-$C_6$ cycloalkyl;

Q is $Q_1$ group:

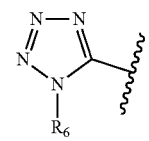

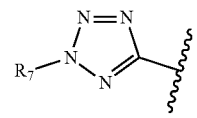

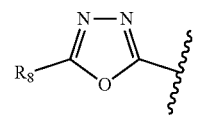

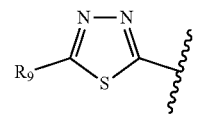

B represents the carbon-carbon double bond, and the stereoisomer of the compound is a cis-stereoisomer in which hydrogen atoms are on a same side of the carbon-carbon double bond B or a trans-stereoisomer in which hydrogen atoms are on both sides of the carbon-carbon double bond B;

R₁ to R₅ are independently selected from hydrogen, hydroxyl, cyano, nitro, halogen, phenyl, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_1$-$C_6$ alkoxy, $C_1$-$C_6$ haloalkoxy, $C_1$-$C_6$ alkylthio, and benzyloxy, wherein R₁ and R₂ form a benzene ring, a 5-7 membered aliphatic heterocycle containing 1-4 heteroatoms or a 5-7 membered aromatic heterocycle containing 1-4 heteroatoms together with the carbon atoms on the connected benzene ring;

$R_2$ and $R_3$ form a benzene ring, a 5-7 membered aliphatic heterocycle containing 1-4 heteroatoms or a 5-7 membered aromatic heterocycle containing 1-4 heteroatoms together with the carbon atoms on the connected benzene ring;

$R_7$ is hydrogen, $C_1$-$C_6$ alkyl, $C_1$-$C_6$ haloalkyl, $C_3$-$C_6$ cycloalkyl, $C_3$-$C_6$ cycloalkyl $C_1$-$C_6$ alkyl, $C_2$-$C_6$ alkenyl, $C_2$-$C_6$ alkynyl, or phenyl; and $R_{11}$ is selected from hydrogen, halogen, cyano, nitro, $C_1$-$C_6$ alkylsulfonyl, $C_1$-$C_6$ haloalkylsulfonyl, $C_1$-$C_6$ alkylsulfinyl, $C_1$-$C_6$ haloalkylsulfinyl, $C_1$-$C_6$ alkylthio, $C_1$-$C_6$ haloalkylthio, $C_1$-$C_6$ alkyl, $C_1$-$C_6$ haloalkyl, $C_1$-$C_6$ alkoxy, $C_1$-$C_6$ haloalkoxy, $C_1$-$C_3$ alkoxy $C_1$-$C_3$ alkyl, $C_1$-$C_6$ alkoxy $C_1$-$C_3$ alkoxy, $C_1$-$C_6$ alkoxy $C_1$-$C_3$ alkoxy $C_1$-$C_3$ alkyl, $C_3$-$C_6$ cycloalkyl, $C_3$-$C_6$ cycloalkyl $C_1$-$C_3$ alkyl, $C_3$-$C_6$ cycloalkyl $C_1$-$C_3$ alkoxy, and $C_3$-$C_6$ cycloalkyloxy.

9. The alkene-containing amide compound of claim 8, the stereoisomer of the compound, and/or the agriculturally acceptable salt thereof, wherein:

$X_1$ and $X_3$ are independently selected from halogen, $C_1$-$C_6$ alkylsulfonyl, $C_1$-$C_6$ alkyl, and $C_1$-$C_6$ haloalkyl;

W is $CX_2$, $X_2$ being $Y_1$ oxy, $Y_1$ oxy $C_1$-$C_6$ alkyl, and $Y_1$ is sulfonyl $C_1$-$C_6$ alkyl or 5-7 membered aliphatic heterocycle containing 1-4 heteroatoms.

\* \* \* \* \*